United States Patent
Kato et al.

(10) Patent No.: US 11,939,279 B2
(45) Date of Patent: *Mar. 26, 2024

(54) COMPOUND, MATERIAL FOR ORGANIC ELECTROLUMINESCENT ELEMENTS, ORGANIC ELECTROLUMINESCENT ELEMENT AND ELECTRONIC DEVICE

(71) Applicant: IDEMITSU KOSAN CO., LTD., Tokyo (JP)

(72) Inventors: Tomoki Kato, Chiba (JP); Taro Yamaki, Ichihara (JP); Masahiro Kawamura, Chiba (JP); Hirokatsu Ito, Ichihara (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 37 days.

This patent is subject to a terminal disclaimer.

(21) Appl. No.: 17/398,172

(22) Filed: Aug. 10, 2021

(65) Prior Publication Data

US 2021/0363096 A1    Nov. 25, 2021

Related U.S. Application Data

(63) Continuation of application No. 15/748,462, filed as application No. PCT/JP2016/072563 on Aug. 1, 2016, now Pat. No. 11,117,857.

(30) Foreign Application Priority Data

Jul. 31, 2015    (JP) .................... 2015-152962

(51) Int. Cl.
*C07C 211/61* (2006.01)
*C09K 11/06* (2006.01)
(Continued)

(52) U.S. Cl.
CPC ............ *C07C 211/61* (2013.01); *C09K 11/06* (2013.01); *H10K 50/11* (2023.02); *H10K 50/156* (2023.02);
(Continued)

(58) Field of Classification Search
None
See application file for complete search history.

(56) References Cited

U.S. PATENT DOCUMENTS 11,117,857 B2 *  9/2021  Kato .................... C07C 211/61
2001/0008711 A1   7/2001  Igarashi
(Continued)

FOREIGN PATENT DOCUMENTS

JP    2001-192652 A    7/2001
JP    2002-249765 A    9/2002
(Continued)

OTHER PUBLICATIONS

International Search Report dated Oct. 18, 2016 in PCT/JP2016/072563 filed Aug. 1, 2016.
(Continued)

*Primary Examiner* — Jay Yang
(74) *Attorney, Agent, or Firm* — Oblon, McClelland, Maier & Neustadt, L.L.P.

(57) ABSTRACT

A compound represented by formula (1) provides a high performance organic electroluminescence device and a novel material for realizing such an organic electroluminescence device:

(Continued)

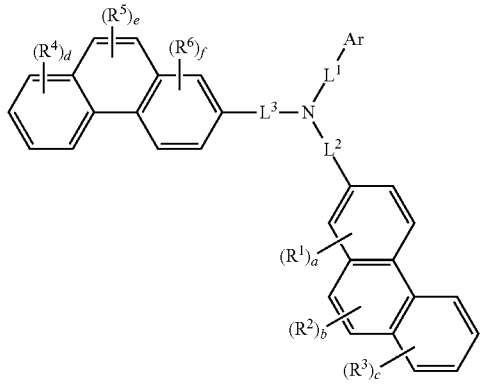

(1)

wherein $R^1$ to $R^6$, a to f, $L^1$ to $L^3$, and Ar are as defined in the description.

15 Claims, 1 Drawing Sheet

(51) Int. Cl.
*H01L 51/00* (2006.01)
*H01L 51/50* (2006.01)
*H10K 50/11* (2023.01)
*H10K 50/15* (2023.01)
*H10K 85/60* (2023.01)
*H10K 50/18* (2023.01)
*H10K 101/10* (2023.01)

(52) U.S. Cl.
CPC ......... *H10K 85/626* (2023.02); *H10K 85/633* (2023.02); *C07C 2603/18* (2017.05); *C07C 2603/26* (2017.05); *C07C 2603/42* (2017.05); *C07C 2603/52* (2017.05); *C07C 2603/54* (2017.05); *C09K 2211/1011* (2013.01); *C09K 2211/1014* (2013.01); *C09K 2211/1088* (2013.01); *H10K 50/15* (2023.02); *H10K 50/18* (2023.02); *H10K 2101/10* (2023.02)

(56) References Cited

U.S. PATENT DOCUMENTS

| | | |
|---|---|---|
| 2002/0094452 A1 | 7/2002 | Ueda et al. |
| 2010/0019657 A1 | 1/2010 | Eum et al. |
| 2014/0091300 A1 | 4/2014 | Pan et al. |
| 2015/0155491 A1 | 6/2015 | Mujica-Fernaud et al. |
| 2016/0043316 A1 | 2/2016 | Takada et al. |
| 2016/0218295 A1 | 7/2016 | Matsuoka |
| 2016/0218296 A1 | 7/2016 | Matsuoka et al. |

FOREIGN PATENT DOCUMENTS

| | | |
|---|---|---|
| JP | 2004-47443 A | 2/2004 |
| JP | 2004231547 | 8/2004 |
| JP | 2006151844 | 6/2006 |
| JP | 2009-215281 A | 9/2009 |
| JP | 2014-511352 A | 5/2014 |
| JP | 2014-517524 A | 7/2014 |
| JP | 2016-40824 A | 3/2016 |
| JP | 2016-136581 A | 7/2016 |
| JP | 2016-136582 A | 7/2016 |
| JP | 2017-10968 A | 1/2017 |
| KR | 10-2012-0100031 A | 9/2012 |
| KR | 10-2013-0040133 A | 4/2013 |
| KR | 10-2016-0019839 A | 2/2016 |
| KR | 10-2016-0052136 A | 5/2016 |
| KR | 10-2016-0087755 A | 7/2016 |
| WO | 2013/055132 A2 | 4/2013 |
| WO | 2016/072690 A1 | 5/2016 |
| WO | WO 2017/022730 A1 | 2/2017 |

OTHER PUBLICATIONS

Combined Chinese Office Action and Search Report dated Apr. 22, 2020 in corresponding Chinese Patent Application No. 201680044714.X (with English Translation of Category of Cited Documents), 9 pages.

Japanese Office Action dated Jul. 28, 2020 in Japanese Patent Application No. 2017-533068 (with unedited computer generated English translation), 12 pages.

Machine English translation of Kawamura (JP 2004-231547). Jan. 6, 2019.

Korean Office Action dated Aug. 17, 2023 in Korean Patent Application No. 10-2018-7002924 (with English translation), 15 pages.

* cited by examiner

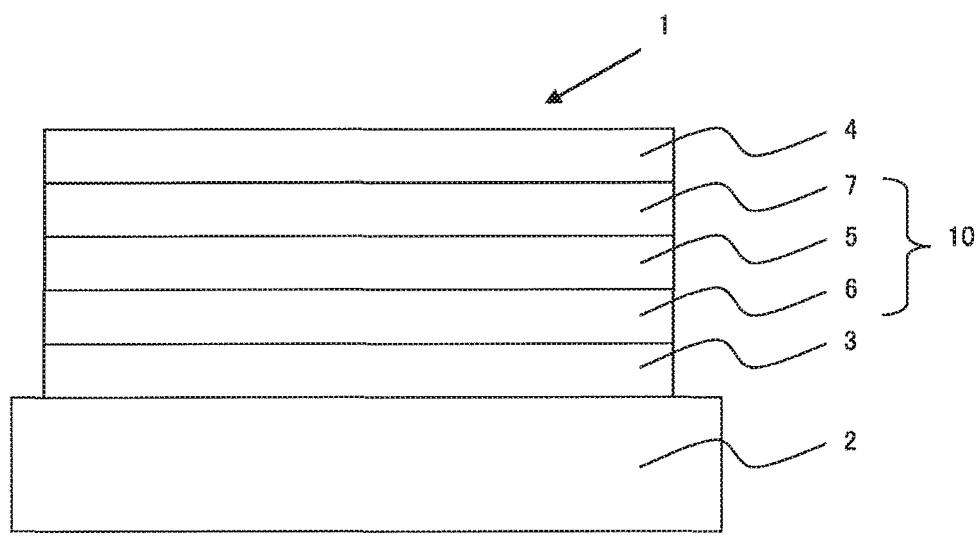

COMPOUND, MATERIAL FOR ORGANIC ELECTROLUMINESCENT ELEMENTS, ORGANIC ELECTROLUMINESCENT ELEMENT AND ELECTRONIC DEVICE

This application is a continuation of U.S. application Ser. No. 15/748,462 filed Jan. 29, 2018, allowed, which is a National Stage of PCT?JP2016/072563 filed Aug. 1, 2016 and claims the benefit of JP 2015-152962 filed Jul. 31, 2015.

TECHNICAL FIELD

The present invention relates to compounds, materials for organic electroluminescence devices, organic electroluminescence devices, and electronic devices.

BACKGROUND ART

An organic electroluminescence device ("organic EL device") generally comprises an anode, a cathode, and an organic thin film layer comprising one or more layers between the anode and the cathode. When a voltage is applied between the electrodes, electrons are injected from the cathode and holes are injected from the anode into a light emitting region. The injected electrons recombine with the injected holes in the light emitting region to form excited states. When the excited state returns to the ground state, the energy is released as light. Therefore, it is important for increasing the efficiency of an organic EL device to develop a compound which transports electrons or holes into a light emitting region efficiently and facilitates the recombination of electrons and holes.

Patent Literature 1 describes a tertiary amine compound, for example, the compounds 1-1, 4-2, and 4-3, wherein a 3-phenanthryl group is bonded to the central nitrogen atom directly or via a linker. Patent Literature 1 describes that these compounds are usable in a hole injecting layer, a hole transporting layer, a light emitting layer, or other layers of organic EL devices. In the working examples, these compounds are used in electron blocking layers (EBL).

Patent Literature 2 describes a tertiary amine compound, for example, the compound of formula 1-3 and the compound of formula 1-4, wherein one 2-phenanthryl group is bonded to the central nitrogen atom via a linker. Patent Literature 2 teaches that these compounds act as a hole injecting material, a hole transporting material, an electron injecting material, an electron transporting material, and a light emitting material. In the working example thereof, the compound of formula 1-3 is used in the hole transporting layer and an electron blocking layer.

However, a new material which further improves the properties of organic EL devices has been still demanded to develop.

CITATION LIST

Patent Literature

Patent Literature 1: US 2015/0155491
Patent Literature 2: JP 2014-511352A

SUMMARY OF INVENTION

Technical Problem

The present invention has been made to solve the above problem and an object thereof is to provide high performance organic EL devices and new materials which realize such organic EL devices.

Solution to Problem

As a result of extensive research for achieving the above object, the inventors have found that, by using a compound represented by formula (1), high performance organic EL devices are obtained.

In an aspect, the invention provides a compound represented by formula (1) (hereinafter also referred to as "compound (1)"):

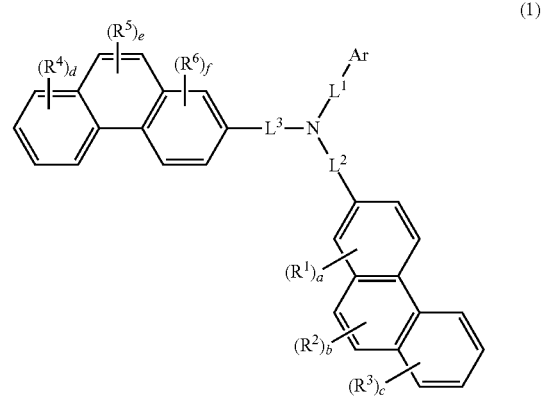

wherein:
each of $R^1$ to $R^6$ is independently an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 50 ring carbon atoms, a halogen atom, or a cyano group;
a is an integer of 0 to 3, b is an integer of 0 to 2, c is an integer of 0 to 4, d is an integer of 0 to 4, e is an integer of 0 to 2, and f is an integer of 0 to 3; each of $(R^1)_0$, $(R^2)_0$, $(R^3)_0$, $(R^4)_0$, $(R^5)_0$, and $(R^6)_0$ respectively means that $R^1$, $R^2$, $R^3$, $R^4$, $R^5$, or $R^6$ is not present; adjacent two groups selected from $R^1$ to $R^3$ are not bonded to each other, thereby failing to form a ring structure; and adjacent two groups selected from $R^4$ to $R^6$ are not bonded to each other, thereby failing to form a ring structure;
each of $L^1$ to $L^3$ is independently a single bond or a substituted or unsubstituted arylene group having 6 to 50 ring carbon atoms;
Ar is a substituted or unsubstituted aryl group having 6 to 50 ring carbon atoms: and
an optional substituent referred to by "substituted or unsubstituted" is at least one selected from the group consisting of an alkyl group having 1 to 20 carbon atoms, a cycloalkyl group having 3 to 50 ring carbon atoms, an aryl group having 6 to 18 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a haloalkyl group having 1 to 20 carbon atoms, a haloalkoxy group having 1 to 20 carbon atoms, a mono-, di-, or tri-substituted silyl group including a substituent selected from an alkyl group having 1 to 20 carbon atoms and an aryl group having 6 to 18 ring carbon atoms, a halogen atom, a cyano group, and a nitro group.

In another aspect, the invention provides a material for organic electroluminescence devices comprising the compound (1).

In still another aspect, the invention provides an organic electroluminescence device comprising a cathode, an anode, and an organic thin film layer disposed between the cathode and the anode, wherein the organic thin film layer comprises one or more layers, the organic thin film layer comprises a light emitting layer, and at least one layer of the organic thin film layer comprises the compound (1).

In still another aspect, the invention provides an electronic device comprising the organic electroluminescence device.

Advantageous Effects of Invention

Organic EL devices produced by using the compound (1) are improved in their performance.

BRIEF DESCRIPTION OF DRAWINGS

FIG. 1 is a schematic view showing the structure of the organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

In the present invention, examples, preferred examples, etc. described with respect to a group may be combined with any of examples, preferred examples, etc. described with respect to other groups. A specific group selected from examples, preferred examples, etc. described with respect to a group may be combined with another specific group selected from examples, preferred examples, etc. described with respect to any of other groups.

The same also applies to the number of atoms, the number of carbon atoms, and other features. In addition, the same also applies to any of the combinations between the groups, the number of atoms, the number of carbon atoms, and other features.

The compound in an aspect of the invention is represented by formula (1):

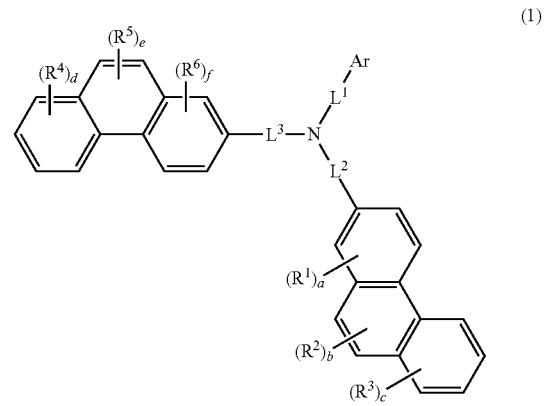

wherein:
  each of $R^1$ to $R^6$ is independently an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 50 ring carbon atoms, a halogen atom, or a cyano group;
  a is an integer of 0 to 3, b is an integer of 0 to 2, c is an integer of 0 to 4, d is an integer of 0 to 4, e is an integer of 0 to 2, and f is an integer of 0 to 3; each of $(R^1)_0$, $(R^2)_0$, $(R^3)_0$, $((R^4)_0$, $(R^5)_0$, and $(R^6)_0$ respectively means that $R^1$, $R^2$, $R^3$, $R^4$, $R^5$, or $R^6$ is not present; adjacent two groups selected from $R^1$ to $R^3$ are not bonded to each other, thereby failing to form a ring structure; and adjacent two groups selected from $R^4$ to $R^6$ are not bonded to each other, thereby failing to form a ring structure;

each of $L^1$ to $L^3$ is independently a single bond or a substituted or unsubstituted arylene group having 6 to 50 ring carbon atoms;

Ar is a substituted or unsubstituted aryl group having 6 to 50 ring carbon atoms; and an optional substituent referred to by "substituted or unsubstituted" is at least one selected from the group consisting of an alkyl group having 1 to 20 carbon atoms, a cycloalkyl group having 3 to 50 ring carbon atoms, an aryl group having 6 to 18 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a haloalkyl group having 1 to 20 carbon atoms, a haloalkoxy group having 1 to 20 carbon atoms, a mono-, di-, or tri substituted silyl group including a substituent selected from an alkyl group having 1 to 20 carbon atoms and an aryl group having 6 to 18 ring carbon atoms, a halogen atom, a cyano group, and a nitro group.

The compound represented by formula (1) provides a high performance organic EL device having a high external quantum efficiency and a long lifetime.

Each of $R^1$ to $R^6$ is independently an alkyl group having 1 to 20, preferably 1 to 5, and more preferably 1 to 4 carbon atoms; a cycloalkyl group having 3 to 50, preferably 3 to 10, more preferably 3 to 6, and still more preferably 5 or 6 ring carbon atoms; a haloalkyl group having 1 to 20, preferably 1 to 5, and more preferably 1 to 4 carbon atoms; an alkoxy group having 1 to 20, preferably 1 to 5, and more preferably 1 to 4 carbon atoms; a haloalkoxy group having 1 to 20, preferably 1 to 5, and more preferably 1 to 4 carbon atoms; an aryl group having 6 to 18, preferably 6 to 12, and more preferably 6 ring carbon atoms; an aryloxy group having 6 to 50, preferably 6 to 24, and more preferably 6 to 12 ring carbon atoms; a halogen atom; or a cyano group.

Preferably, each of $R^1$ to $R^6$ is independently an alkyl group having 1 to 20, preferably 1 to 5, and, more preferably 1 to 4 carbon atoms; an aryl group having 6 to 18, preferably 6 to 12, and more preferably 6 ring carbon atoms; an aryloxy group having 6 to 50, preferably 6 to 24, and more preferably 6 to 12 ring carbon atoms; or a cyano group.

More preferably, each of $R^1$ to $R^6$ is independently an alkyl group having 1 to 20, preferably 1 to 5, and more preferably 1 to 4 carbon atoms or an aryl group having 6 to 18, preferably 6 to 12, and more preferably 6 ring carbon atoms.

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred, a methyl group, an ethyl group, a n-propyl group, an isopropyl group, a n-butyl group, an isobutyl group, a s-butyl group, and a t-butyl group being more preferred, a methyl group and a t-butyl group being still more preferred, and a methyl group being further more preferred.

Examples of the cycloalkyl group having 3 to 50 ring carbon atoms include a cyclopropyl group, a cyclobutyl group, a cyclopentyl group, a cyclohexyl group, and a cycloheptyl group.

The haloalkyl group having 1 to 20 carbon atoms is, for example, a group obtained by replacing at least one, preferably 1 to 7 hydrogen atoms, or all the hydrogen atoms of the alkyl group having 1 to 20 carbon atoms mentioned above with a fluorine atom. Preferred examples thereof include a heptafluoropropyl group (inclusive of isomeric groups), a pentafluoroethyl group, a 2,2,2-trifluoroethyl group, and a trifluoromethyl group, with a pentafluoroethyl group, a 2,2,2-trifluoroethyl group, and a trifluoromethyl group being more preferred, and a trifluoromethyl group being still more preferred.

The alkoxy group having 1 to 20 carbon atoms is represented by —$OR^{11}$, wherein $R^{11}$ is the alkyl group having 1 to 20 carbon atoms mentioned above. The alkoxy group is preferably a t-butoxy group, a propoxy group (inclusive of isomeric groups), an ethoxy group, or a methoxy group, more preferably an ethoxy group or a methoxy group, and still more preferably a methoxy group.

The haloalkoxy group haying 1 to 20 carbon atoms is represented by —$OR^{12}$, wherein $R^{12}$ is the fluoroalkyl group having 1 to 20 carbon atoms mentioned above. The fluoroalkoxy group is preferably a heptafluoropropoxy group (inclusive of isomeric groups), a pentafluoroethoxy group, a 2,2,2-trifluoroethoxy group, or a trifluoromethoxy group, more preferably a pentafluoroethoxy group, a 2,2,2-trifluoroethoxy group, or a trifluoromethoxy group, and still more preferably a trifluoromethoxy group.

The aryl group having 6 to 18 ring carbon atoms is preferably a phenyl group a 1-naphthyl group, a 2-naphthyl group, a biphenylyl group, for example, a 2-, 3-, or 4-biphenylyl group, or a terphenylyl group, for example, a 2-p-terphenylyl group, a 4-p-terphenylyl group, a 2'-m-terphenylyl group, or a 5'-m-terphenylyl group, more preferably a phenyl group, a 1-naphthyl group, a 2-naphthyl group, or a biphenylyl group, for example, a 2-, 3- or 4-biphenylyl group, and more preferably a phenyl group.

The aryloxy group having 6 to 50 ring carbon atoms is represented by —$OR^{13}$, wherein $R^{13}$ is an aryl group having 6 to 50, preferably 6 to 24, and more preferably 6 to 12 ring carbon atoms.

Examples of the aryl group include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group, with a phenyl group, a biphenylyl group, a terphenylyl group, and a naphthyl group being preferred, a phenyl group, a biphenylyl group, and a naphthyl group being more preferred, and a phenyl group being still more preferred.

The halogen atom includes a fluorine atom, a chlorine atom, a bromine atom and an iodine atom, with a fluorine atom being preferred.

a is an integer of 0 to 3, preferably 0 to 2, more preferably 0 or 1, and still more preferably 0. b is an integer of 0 to 2, preferably 0 or 1, and more preferably 0. c is an integer of 0 to 4, preferably 0 to 2, more preferably 0 or 1, and still more preferably 0. d is all integer of 0 to 4, preferably 0 to 2, more preferably 0 or 1, and still more preferably 0. e is an integer of 0 to 2, preferably 0 or 1, and more preferably 0. f is an integer of 0 to 3, preferably 0 to 2, more preferably 0 or 1, and still more preferably 0. In a preferred embodiment, a to f are all 0.

When each of a to f is 0, i.e., each of $(R^1)_0$, $(R^2)_0$, $(R^3)_0$, $(R^4)_0$, $(R^5)_0$, and $(R^6)_0$ means that $R^1$, $R^2$, $R^3$, $R^4$, $R^5$ or $R^6$ is not present, i.e., each benzene ring is not substituted by $R^1$, $R^2$, $R^3$, $R^4$, $R^5$ or $R^6$.

When a, b, c, d, e, or f is an integer of 2 or more, two to three $R^1$'s, two $R^2$'s, two to four $R^3$'s, two to four $R^4$'s, two $R^5$'s, and two to three $R^6$'s may be respectively the same or different. Adjacent two selected from $R^1$ to $R^6$ are not bonded to each other, thereby failing to form a ring structure.

Ar is a substituted or unsubstituted aryl group having 6 to 50, preferably 6 to 25, more preferably 6 to 24, and still more preferably 6 to 18 ring carbon atoms.

The aryl group in the substituted or unsubstituted aryl group having 6 to 50 ring carbon atoms for Ar is, for example, a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a benzofluorenyl group, a 9,9'-spirobifluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group, with a biphenylyl group, a terphenylyl group, a naphthyl group, a phenanthryl group, a triphenylenyl group, a fluorenyl group, a 9,9'-spirobifluorenyl group, and a fluoranthenyl group being preferred, and a biphenylyl group, a terphenylyl group, a 2-phenanthryl group, and a fluorenyl group being more preferred.

Each of $L^1$ to $L^3$ is independently a single bond or a substituted or unsubstituted arylene group having 6 to 50, preferably 6 to 24, and more preferably 6 to 12 ring carbon atoms, preferably a single bond or a substituted or unsubstituted arylene group having 6 to 12 ring carbon atoms, and more preferably a single bond or a phenylene group.

The arylene group of the substituted or unsubstituted arylene group having 6 to 50 ring carbon atoms is selected from the group consisting of divalent groups which are obtained by removing one hydrogen atom from a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a triphenylenyl group, a benzophenanthryl group, a phenalenyl group, a fluorenyl group, a benzofluorenyl group, a 9,9'-spirobifluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group.

In formula (1), the optional substituent referred to by "substituted or unsubstituted" is at least one selected from the group consisting of an alkyl group having 1 to 20, preferably 1 to 5, and more preferably 1 to 4 carbon atoms; a cycloalkyl group having 3 to 50, preferably 3 to 10, more preferably 3 to 6, and still more preferably 5 or 6 ring carbon atoms; an aryl group having 6 to 18, preferably 6 to 12, more preferably 6 to 10, and still more preferably 6 ring carbon atoms; an aralkyl group, having 7 to 30 carbon atoms which includes an aryl group having 6 to 18, preferably 6 to 12, more preferably 6 to 10, and still more preferably 6 ring carbon atoms; an alkoxy group having 1 to 20, preferably 1 to 5, and more preferably 1 to 4 carbon atoms; an aryloxy group having 6 to 18, preferably 6 to 12, more preferably 6 to 10, and still more preferably 6 ring carbon atoms; a haloalkyl group having 1 to 20, preferably 1 to 5, and more preferably 2 to 4 carbon atoms; a haloalkoxy group having 1 to 20, preferably 1 to 5, and more preferably 1 to 4 carbon atoms; a mono-, di-, or tri-substituted silyl group having a substituent selected from an alkyl group having 1 to 20, preferably 1 to 5, and more preferably 1 to 4 carbon atoms and an aryl group having 6 to 18, preferably 6 to 12, more preferably 6 to 10, and still more preferably 6 ring carbon atoms; a halogen atom; a cyano group; and a nitro group.

The details of the alkyl group having 1 to 20 carbon atoms, the cycloalkyl group having 3 to 50 ring carbon atoms, the alkoxy group having 1 to 20 carbon atoms, the haloalkyl group haying 1 to 20 carbon atoms, the haloalkoxy group having 1 to 20 carbon atoms, and the halogen atom, each for the optional substituent, are as described above with respect to $R^1$ to $R^6$.

Examples of the aryl group having 6 to 18 ring carbon atoms for the optional substituent include a phenyl group, a 1-naphthyl group, a 2-naphthyl group, a biphenylyl group, such as a 2-, 3- or 4-biphenylyl group, and a terphenylyl group, such as a 2-p-terphenylyl group, a 4-p-terphenylyl group, a 2'-m-terphenylyl group, and a 5'-m-terphenylyl group.

The details of the aryl group having 6 to 18 ring carbon atoms in the aralkyl group having 7 to 30 carbon atom which includes an aryl group having 6 to 18 ring carbon atoms, mentioned above as the optional substituent, are as described above.

The details of the aryl group in the aryloxy group having 6 to 18 ring carbon atoms for the optional substituent are as described above.

The haloalkyl group in the haloalkyl group having 1 to 20 carbon atoms for the optional substituent is a group obtained by replacing at least one, preferably 1 to 7 hydrogen atoms, or all the hydrogen atoms of the alkyl group having 1 to 20 carbon atoms mentioned above with respect to $R^1$ to $R^6$ with a halogen atom selected from the group consisting of a fluorine atom, a chlorine atom, a bromine atom, and an iodine atom, preferably a fluorine atom. The haloalkyl group is preferably a heptafluoropropyl group (inclusive of isomeric groups), a pentafluoroethyl group, a 2,2,2-trifluoroethyl group, or a trifluoromethyl group, more preferably a pentafluoroethyl group, a 2,2,2-trifluoroethyl group, or a trifluoromethyl group, and still more preferably a trifluoromethyl group.

The haloalkoxy group having 1 to 20 carbon atoms for the optional substituent is represented by —$OR^{14}$, wherein $R^{14}$ is the haloalkyl group having 1 to 20 carbon atoms mentioned above and preferably a fluoroalkyl group having 1 to 20 carbon atoms. The haloalkoxy group is preferably a heptafluoropropoxy group (inclusive of isomeric groups), a pentafluoroethoxy group, a 2,2,2-trifluoroethoxy group, or a trifluoromethoxy group, more preferably a pentafluoroethoxy group, a 2,2,2-trifluoroethoxy group, or a trifluoromethoxy group, and still more preferably a trifluoromethoxy group.

The details of the alkyl group and the aryl group in the mono-, or tri-substituted silyl group including a substituent selected from an alkyl group having 1 to 20 carbon atoms and an aryl group having 6 to 18 ring carbon atoms, mentioned above as the optional substituent, are as described above. Examples thereof include a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.
In a preferred embodiment of the invention, Ar is represented by any of formulae (a) to (m):
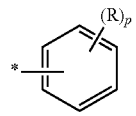
(a)
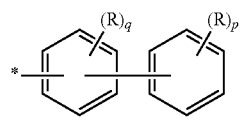
(b)
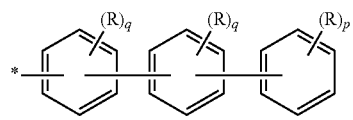
(c)
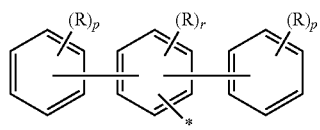
(d)
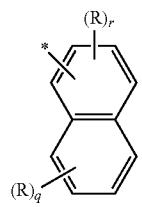
(e)
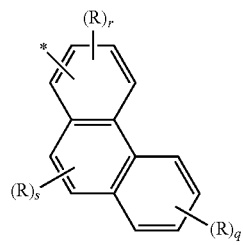
(f)
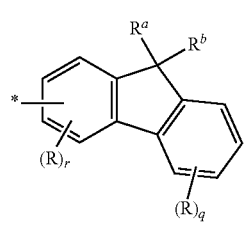
(g)
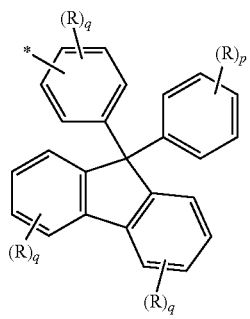
(h)
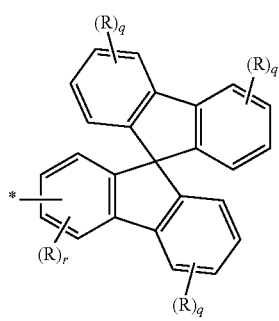
(i)
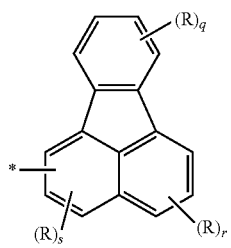
(j)
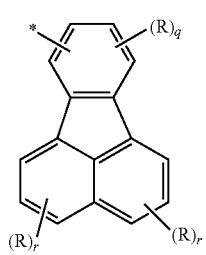
(k)
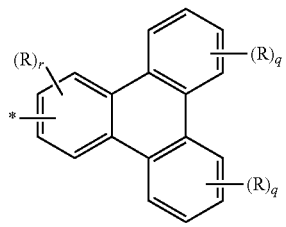
(l)
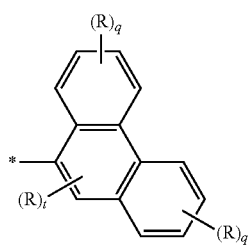
(m)

In formulae (a) to (m), * is a bond to $L^1$ or $L^2$ in formula (1).

In formulae (a) to (m), each R is independently selected from the substituents described above with respect to the optional substituents referred to by "substituted or unsubstituted" in formula (1).

Preferably, each R is independently selected from an alkyl group having 1 to 20 carbon atoms, a cycloalkyl group having 3 to 50 ring carbon atoms, an aryl group having 6 to 18 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group.

More preferably, each R is independently selected from an alkyl group having 1 to 20 carbon atoms and an aryl group having 6 to 18 ring carbon atoms. Still more preferably, each R is independently selected from an aryl group having 6 to 18 ring carbon atoms, with a phenyl group being further more preferred.

In formulae (a) to (m), each p is independently an integer of 0 to 5, preferably 0 to 3, more preferably 0 or 1, and still more preferably 0. Each q is independently an integer of 0 to 4, preferably 0 to 2, more preferably 0 or 1, and still more preferably 0. Each r is independently an integer of 0 to 3, preferably 0 to 2, more preferably 0 or 1, and still more preferably 0. s is an integer of 0 to 2, preferably 0 or 1, and more preferably 0. t is 0 or 1 and preferably 0.

When p, q, r or s is an integer of 2 or more, two to five Rs, two to four Rs, two to three Rs, or two Rs may be the same or different.

In an embodiment of the invention, adjacent two Rs in formulae (a) to (f) and (h) to (m) may be bonded to each other to form a ring structure. In formula (g), two selected from R, $R^a$, and $R^b$ may be bonded to each other to form a ring structure. The ring structure is preferably an aromatic hydrocarbon ring, such as a benzene ring, or an aromatic heterocyclic ring comprising a ring heteroatom, such as a nitrogen atom, an oxygen atom, and a sulfur atom.

In another embodiment of the invention, adjacent two Rs in formulae (a) to (f) and (h) to (m) are not bonded to each other. In still another embodiment of the invention, two selected from R, $R^a$, and $R^b$ in formula (g) are not bonded to each other, thereby failing to form a ring structure.

When any of p to t is 0, $(R)_0$ means that R is not present, i.e., the ring is not substituted by R. In an embodiment of the invention, the group represented by any of formulae (a) to (m) has preferably one or two Rs and more preferably one R. In another embodiment of the invention, the group represented by any of formulae (a) to (m) is preferably not substituted by R, i.e., p to t are preferably all 0.

Each of $R^a$ and $R^b$ of formula (g) is independently an alkyl group having 1 to 20, preferably 1 to 5, and more preferably 1 to 4 carbon atoms; an aryl group having 6 to 18, preferably 6 to 10, and more preferably 6 ring carbon atoms; a haloalkyl group, preferably a fluoroalkyl group, each having 1 to 20, preferably 1 to 5, and more preferably 1 to 4 carbon atoms; an alkoxy group having 1 to 20, preferably 1 to 5, and more preferably 1 to 4 carbon atoms; a haloalkoxy group, preferably a fluoroalkoxy group, each having 1 to 20, preferably 1 to 5, and more preferably 1 to 4 carbon atoms; an aryloxy group having 6 to 18, preferably 6 to 10, and more preferably 6 ring carbon atoms; a halogen atom; or a cyano group.

The details for the groups represented by $R^a$ and $R^b$ are the same as those mentioned above with respect to the optional substituents referred to by "substituted or unsubstituted" of formula (1).

Preferably, each of $R^a$ and $R^b$ is independently selected from an alkyl group having 1 to 20 carbon atoms and an aryl group having 6 to 18 ring carbon atoms and more preferably selected from a methyl group, an ethyl group, and a phenyl group.

Formula (b) is preferably a 2-biphenylyl group, a 3-biphenylyl group, or a 4-biphenylyl group, each being substituted or not substituted by a substituent R.

Formula (c) is preferably a 2-, 3 or 4-p-terphenylyl group, a 2-, 3- or 4-m-terphenylyl group, or a 2-, 3- or 4-o-terphenylyl group, each being substituted or not substituted by a substituent R.

Formula (d) is preferably a 2'-p-terphenylyl group, a 2'-, 4'-, or 5'-m-terphenylyl group, or a 4'-o-terphenylyl group, each being substituted or not substituted by a substituent R.

Formula (e) is preferably a 1-naphthyl group or a 2-naphthyl group, each being substituted or not substituted by a substituent R.

Formula (f) is preferably a 2-phenanthryl group, a 3-phenanthryl group, or a 4-phenanthryl group, more preferably a 2-phenanthryl group or a 4-phenanthryl group, and still more preferably a 2-phenanthryl group, each being substituted or not substituted by a substituent R. The details of R are as described above with respect to $R^1$ to $R^6$.

In formula (g), $R^a$ and $R^b$ are preferably both phenyl groups or both methyl groups, or one of $R^a$ and $R^b$ is a methyl group and the other is a phenyl group. The group represented by formula (g) is bonded to $L^1$ or $L^2$ of formula (1) at any of 1-position to 4-position and preferably at 2-position or 4-position of the fluorene ring.

Formula (h) is preferably a 4-(9-phenylfluorene-9-yl) phenyl group which is substituted or not substituted by a substituent R.

The group represented by formula (i) is bonded to $L^1$ or $L^2$ of formula (1) at any of 1-position to 4-position and preferably at 2-position or 4-position of the fluorene ring.

The group represented by formula (j) is bonded to $L^1$ or $L^2$ of formula (1) preferably at 2-position or 3-position of the fluoranthene ring.

The group represented by formula (k) is bonded to $L^1$ or $L^2$ of formula (1) preferably at 7-position or 8-position of the fluoranthene ring.

The group represented by formula (l) is bonded to $L^1$ or $L^2$ of formula (1) preferably at 2-position of the triphenylene ring.

In a more preferred embodiment of the compound represented by formula (1), Ar is independently represented by formula (b-1), (b-2), (b-3), (c-1), (c-2), (c-3), (d-1), (d-2), (d-3), (e-1), (e-2), (f-1), (f-2), (f-3), (f-4), (g-1), (g-2), (g-3), (h-1), (i-1), (i-2), (j-1), (j-2), (k-1), (k-2), (l-1), or (m).

In these formulae, R, p, q, r, s, t, and * are as described above, and adjacent two Rs are not bonded to each other, thereby failing to form a ring structure.

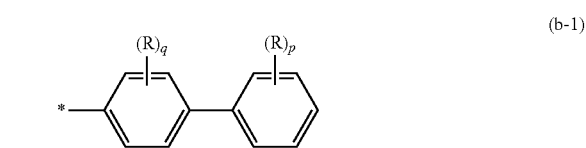

(b-1)

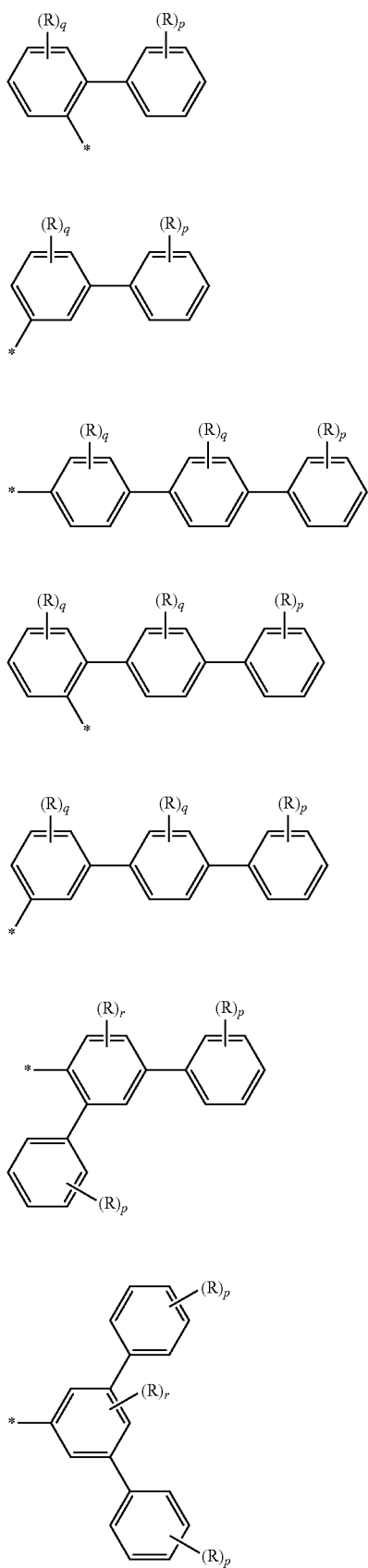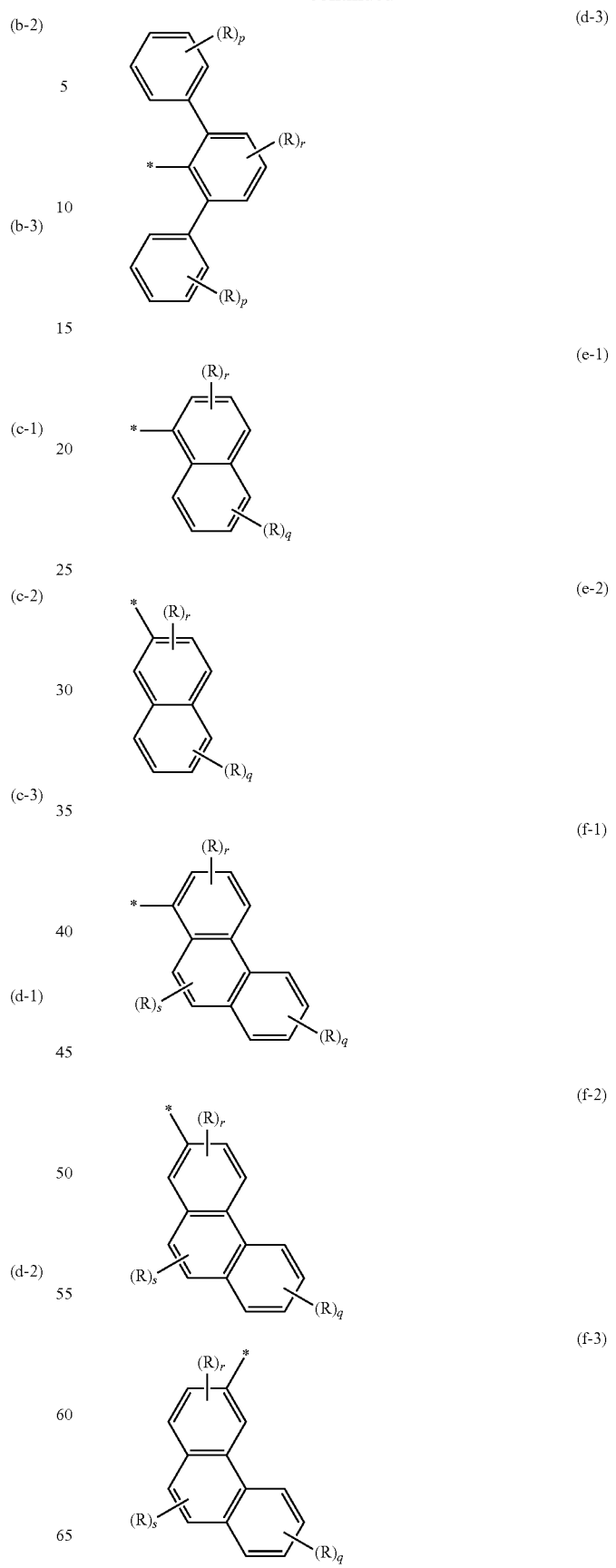

(f-4)
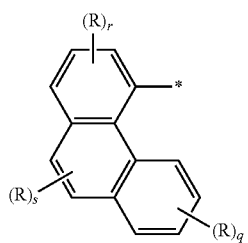
(g-1)
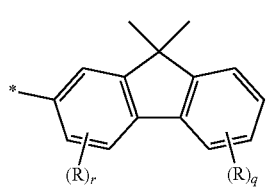
(g-2)
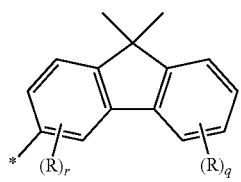
(g-3)
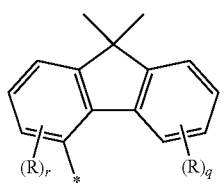
(h-1)
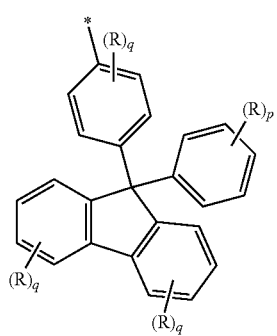
(i-1)
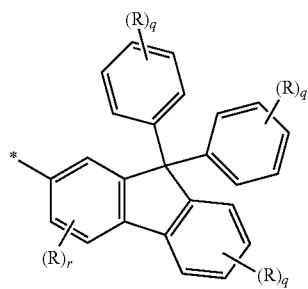
(i-2)
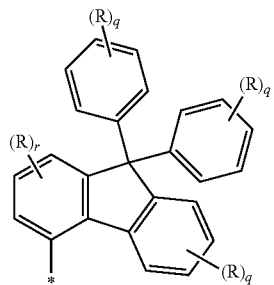
(j-1)
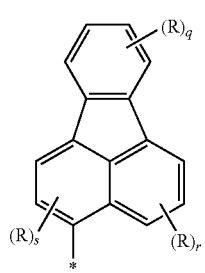
(j-2)
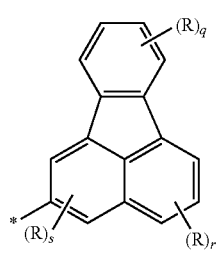
(k-1)
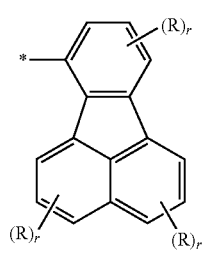

-continued

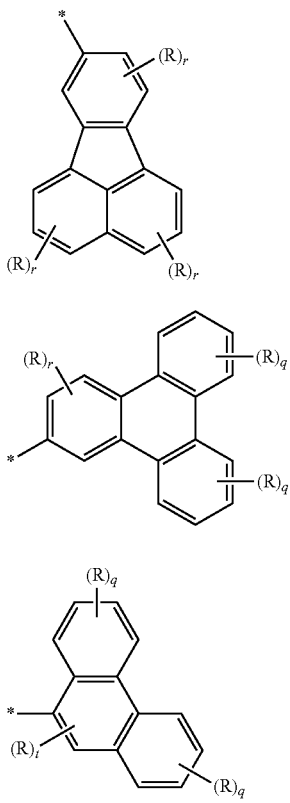

In an embodiment of the invention, each of $L^1$ to $L^3$ may be a single bond or each of $L^1$ to $L^3$ may be a substituted or unsubstituted arylene group having 6 to 50, preferably 6 to 24, and more preferably 6 to 12 ring carbon atoms.

The substituted or unsubstituted arylene group having 6 to 50 ring carbon atoms is preferably represented by formula (ii) or (iii):

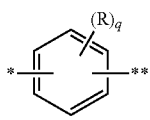

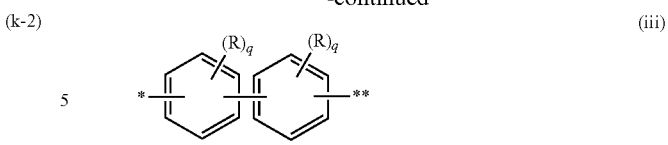

wherein:

R and q are the same as defined with respect to formulae (a) to (m);

when $L^1$ is represented by formula (ii) or (iii), one of * and ** is a bond to Ar in formula (1), and the other is a bond to the nitrogen atom in formula (1);

when $L^2$ is represented by formula (ii) or (iii), one of * and ** is a bond to the 2-phenanthryl group in formula (1), and the other is a bond to the nitrogen atom in formula (1); and when $L^3$ is represented by formula (ii) or (iii), one of * and ** is a bond to the 2-phenanthryl group in formula (1), and the other is a bond to the nitrogen atom in formula (1).

Formulae (ii) and (iii) are preferably represented by the following formulae:

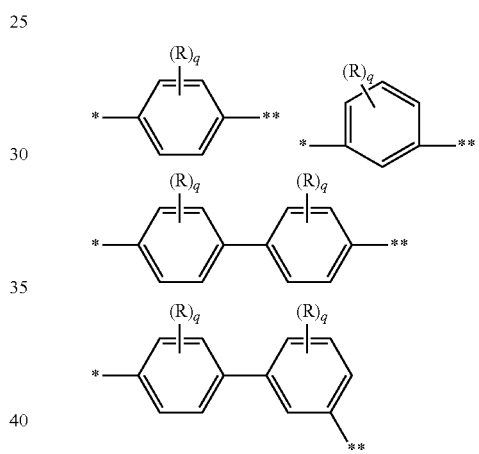

wherein R, q, *, and ** are as described above.

$L^2$ may be a single bond. $L^3$ may be a single bond. $L^2$ and $L^3$ may be both single bonds. $L^1$ to $L^3$ may be all single bonds.

Examples of the compound (1) are shown below, although not limited thereto.

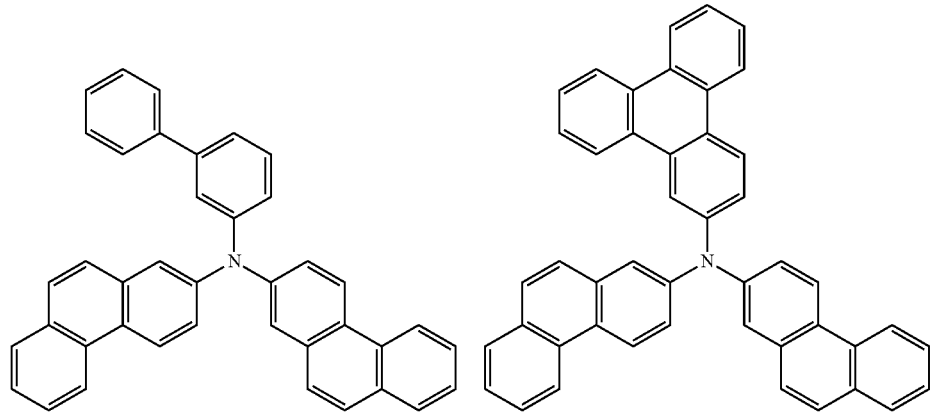

-continued
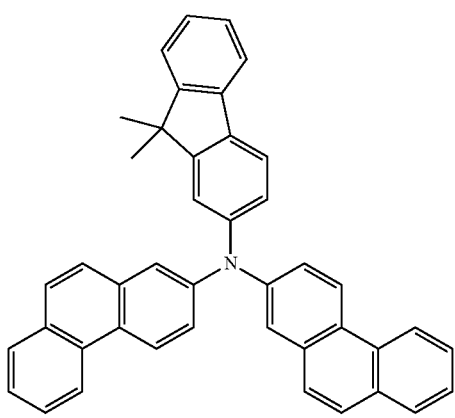
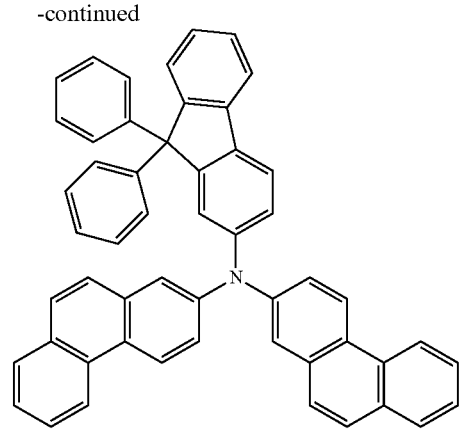
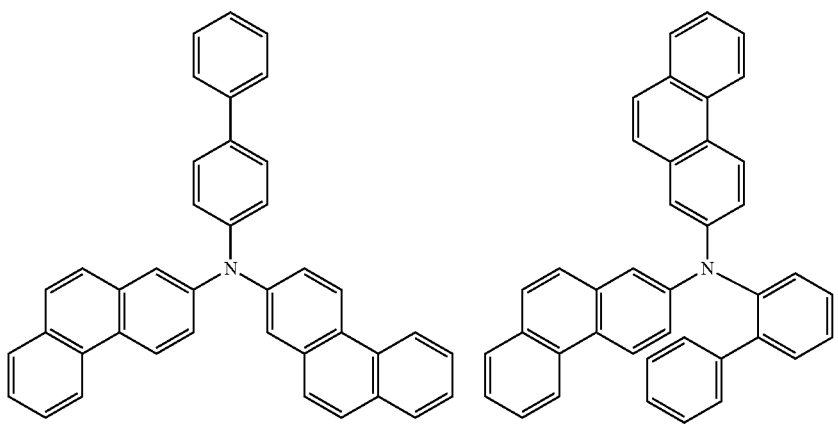
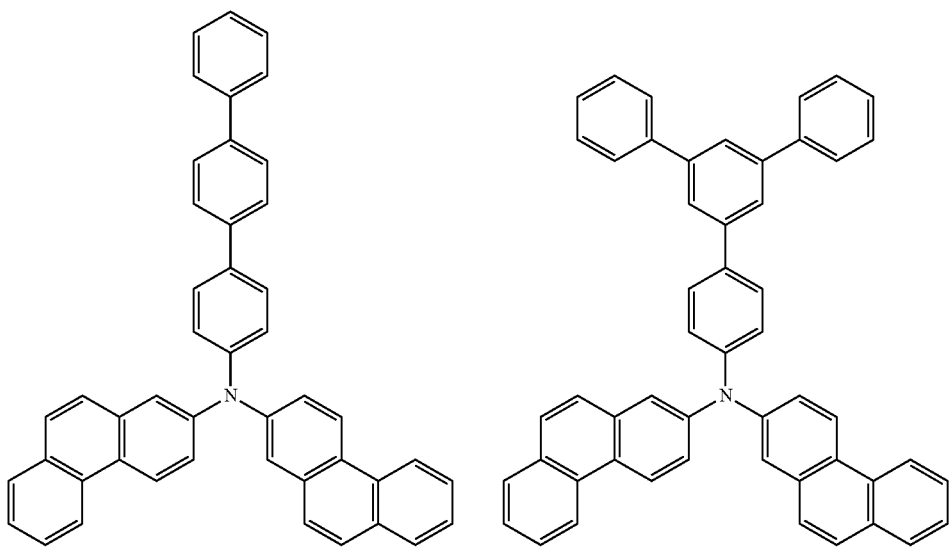

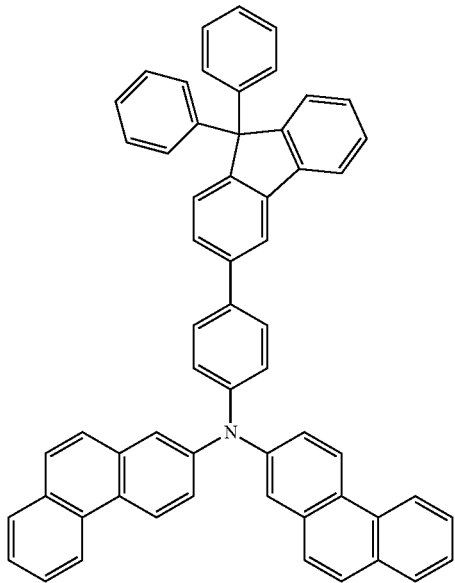
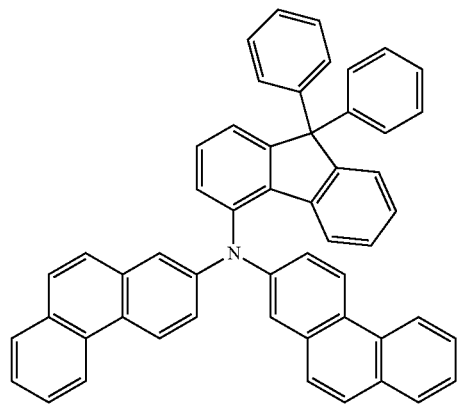
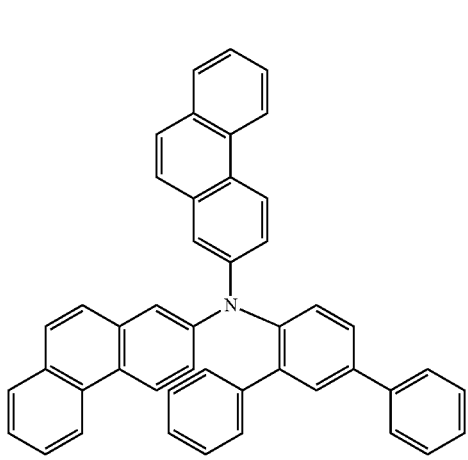
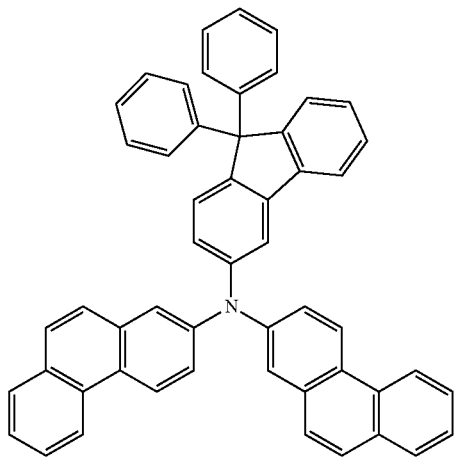
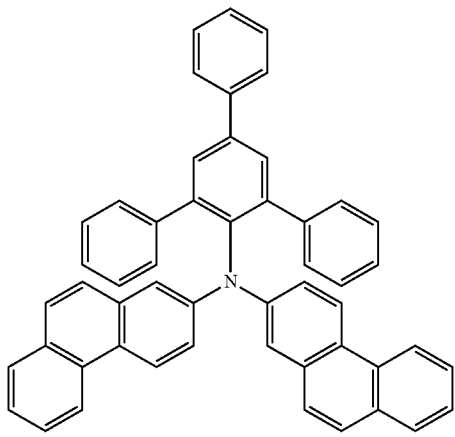
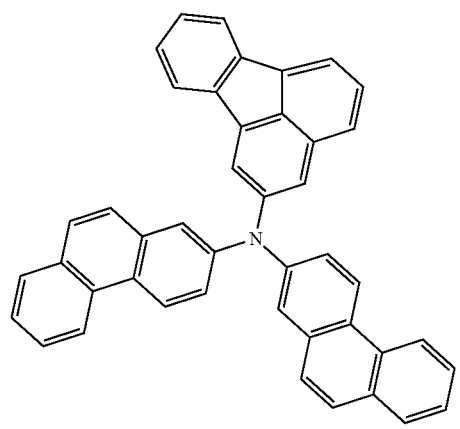

-continued
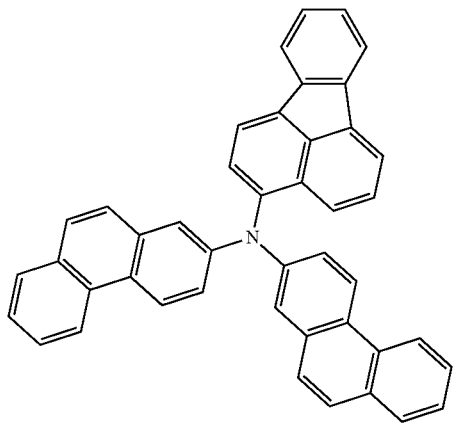
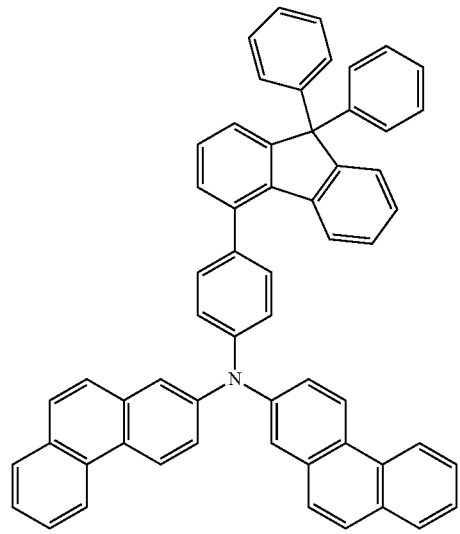
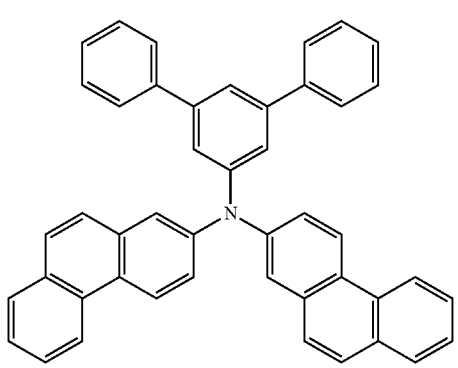
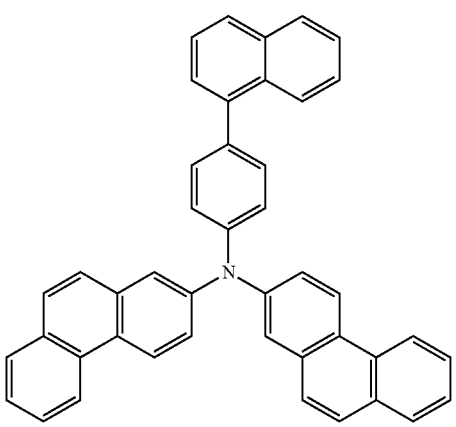
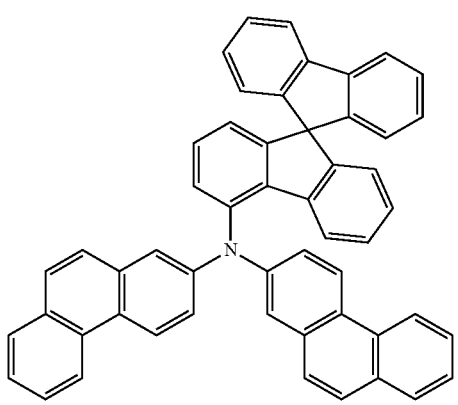
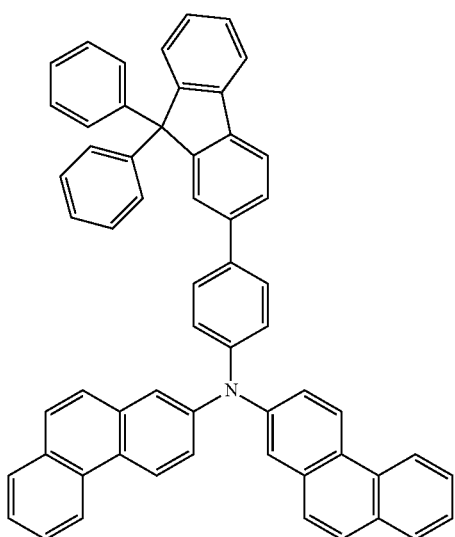

-continued
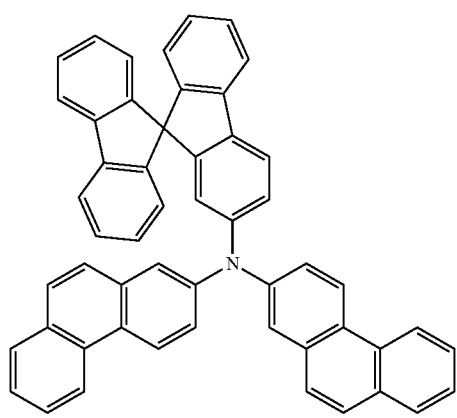
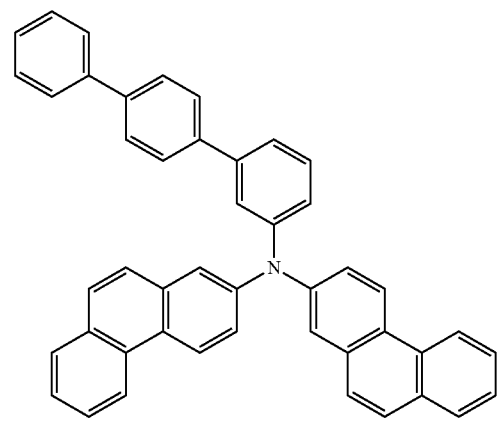
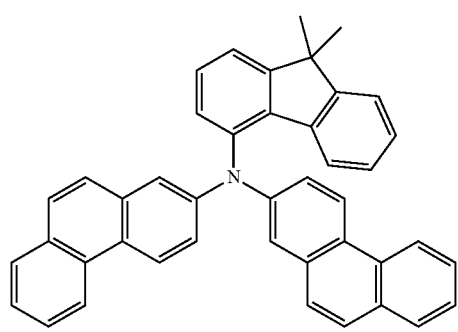
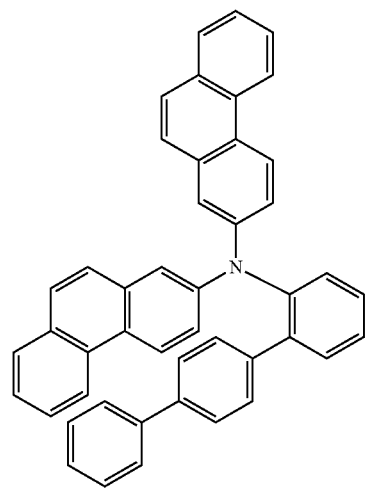
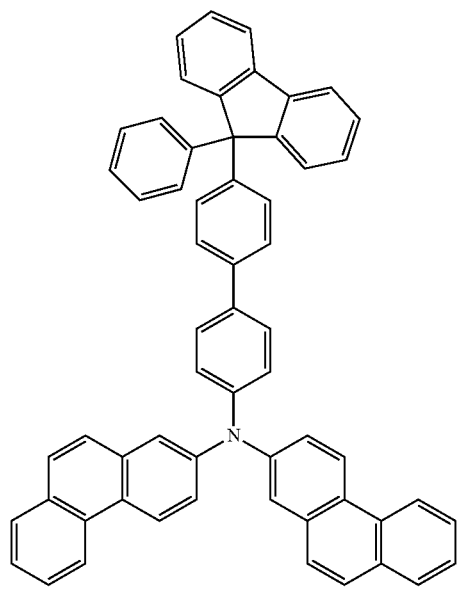
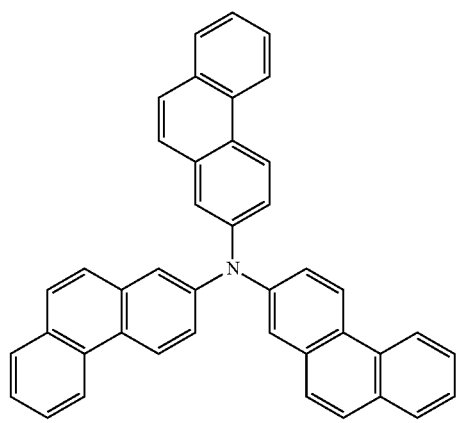

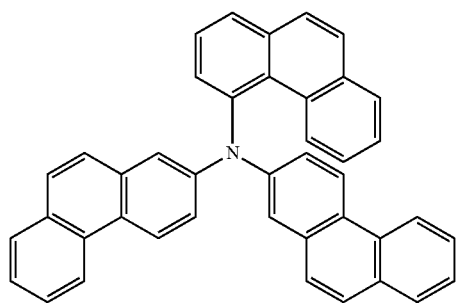
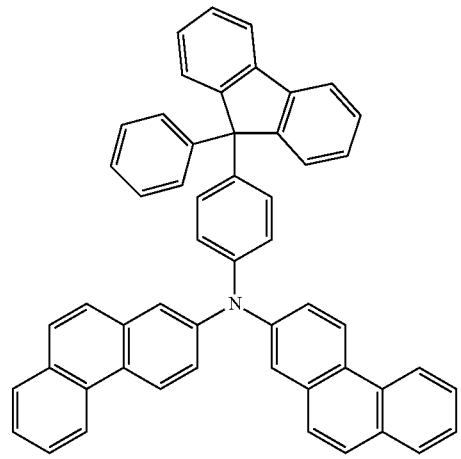
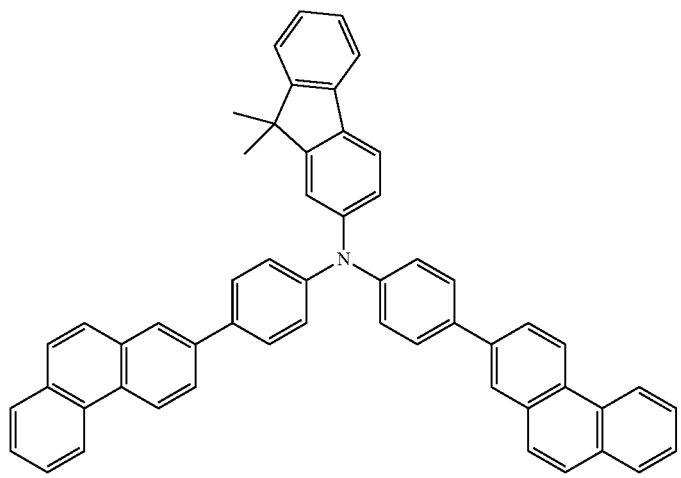
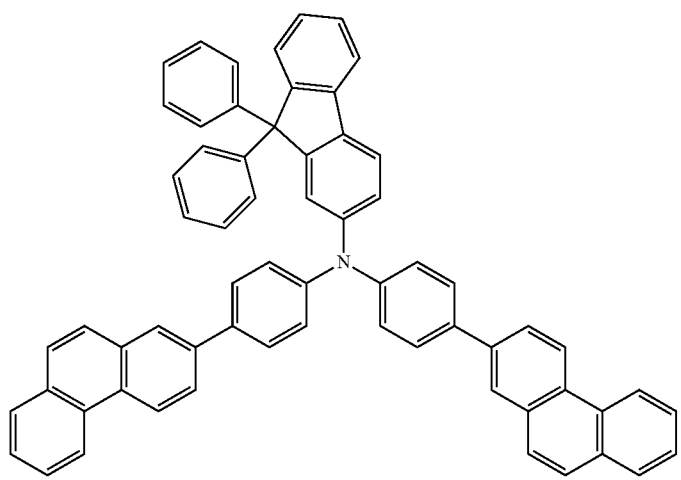

-continued
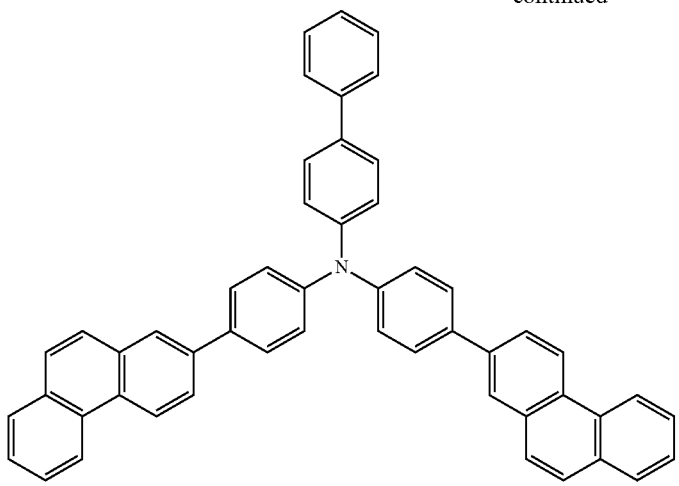
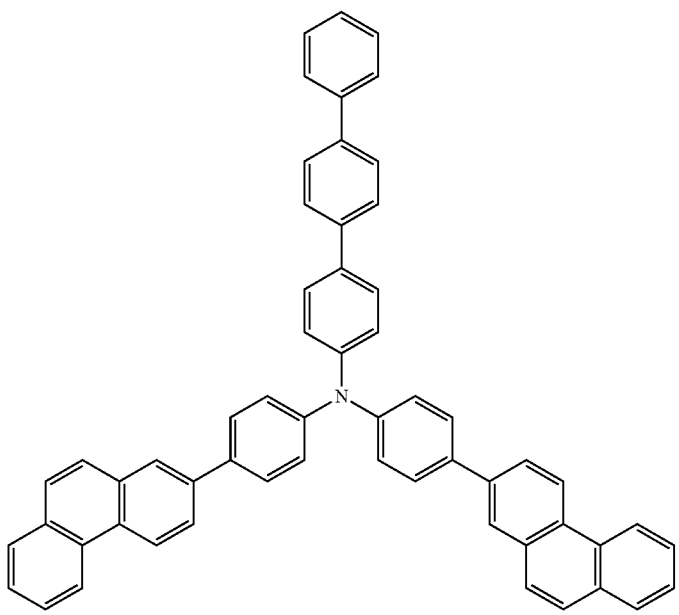
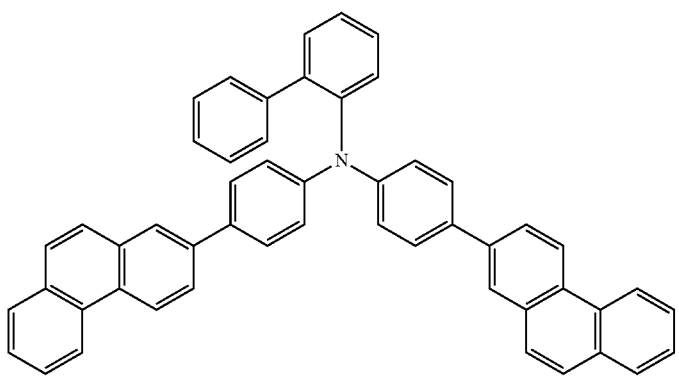

-continued
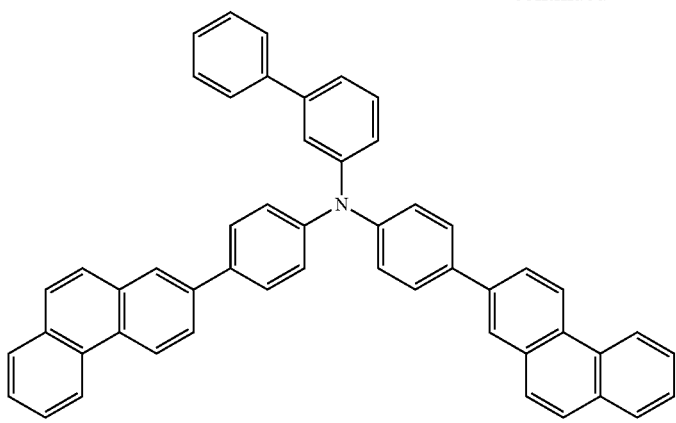
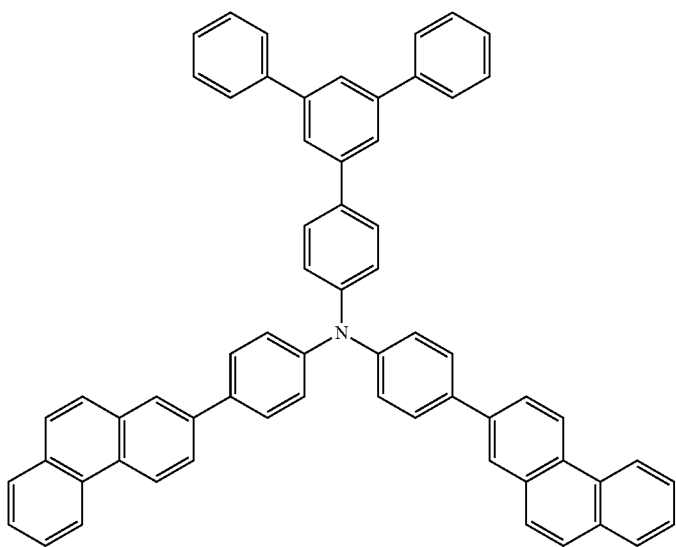
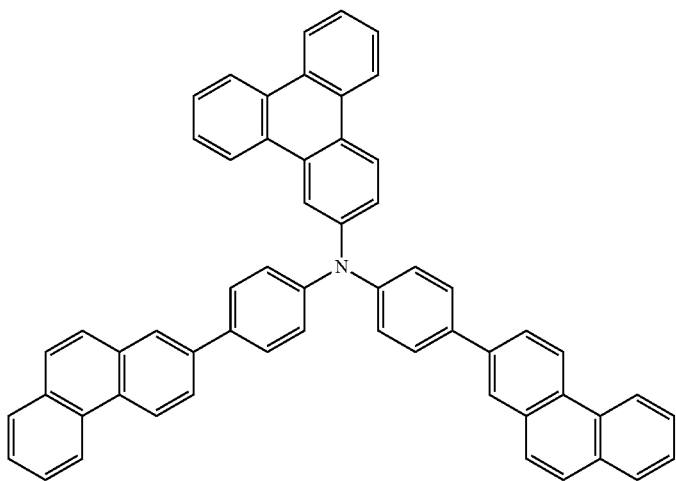

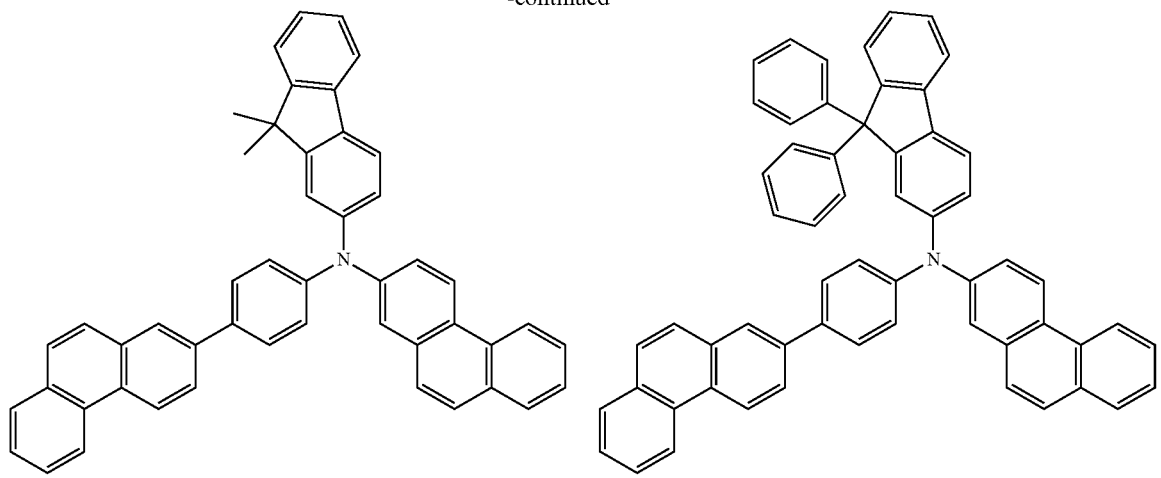
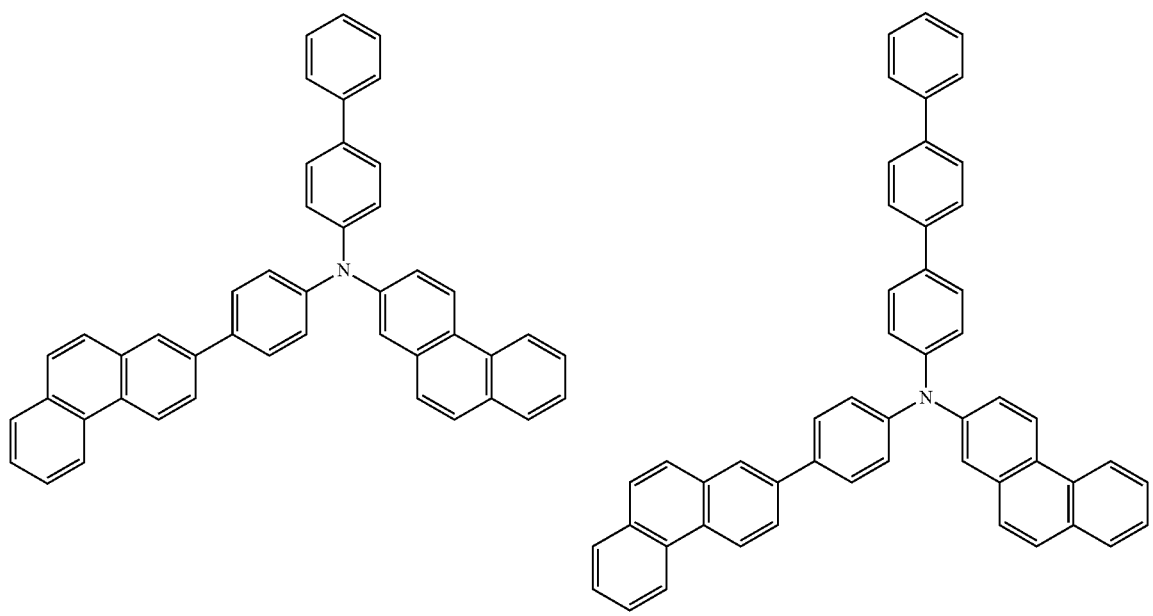
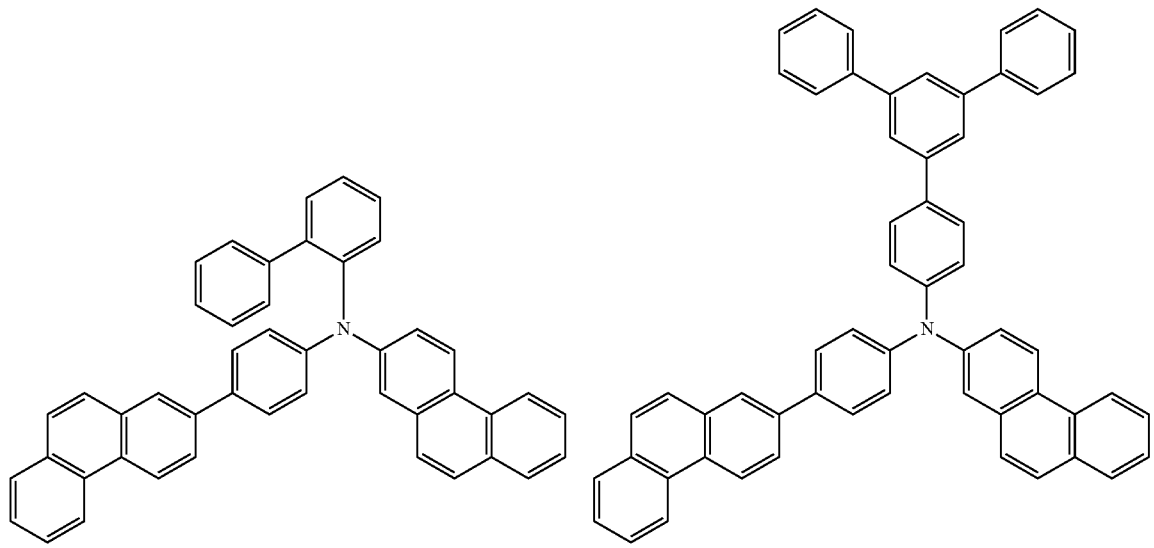

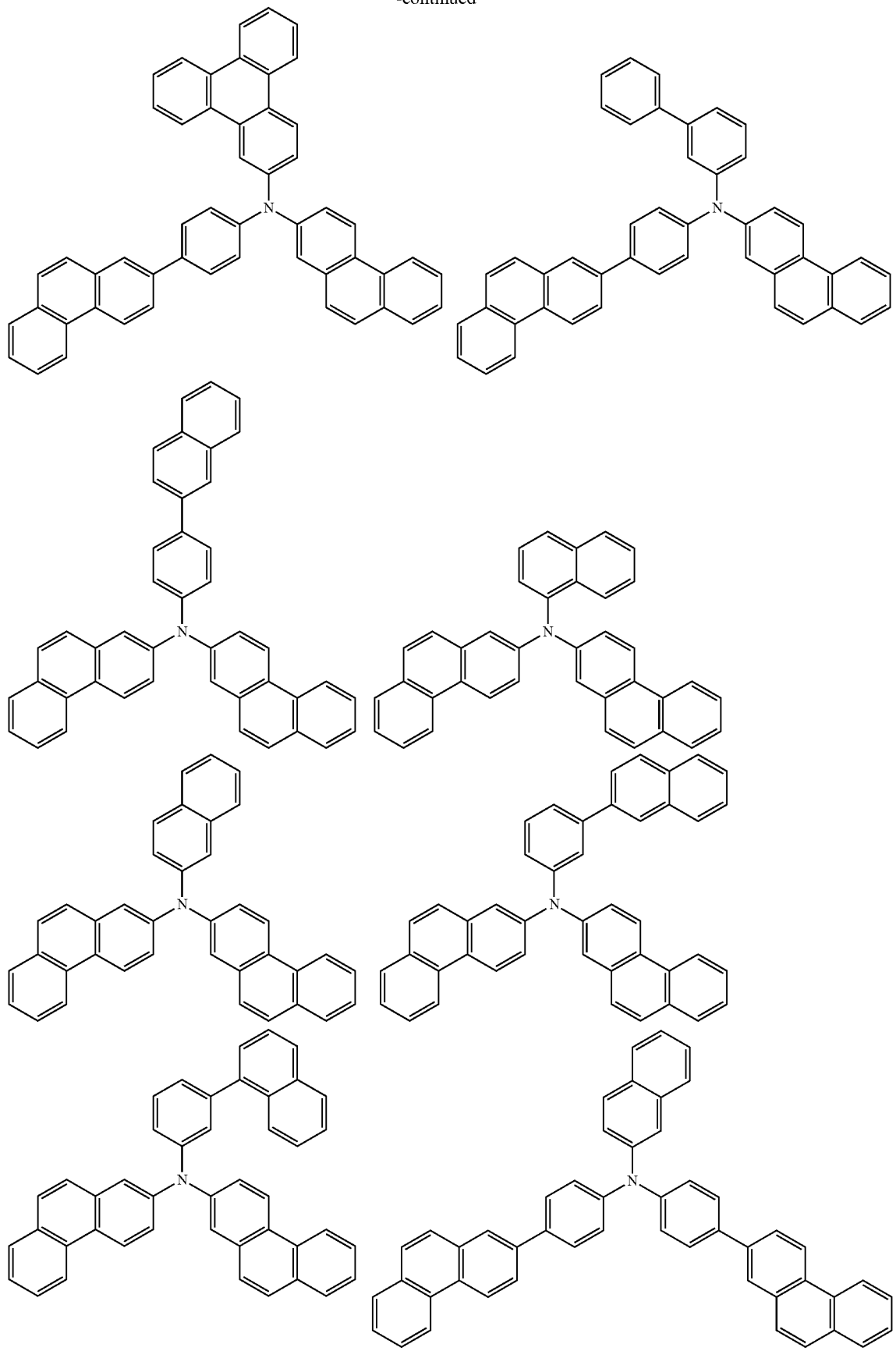

-continued
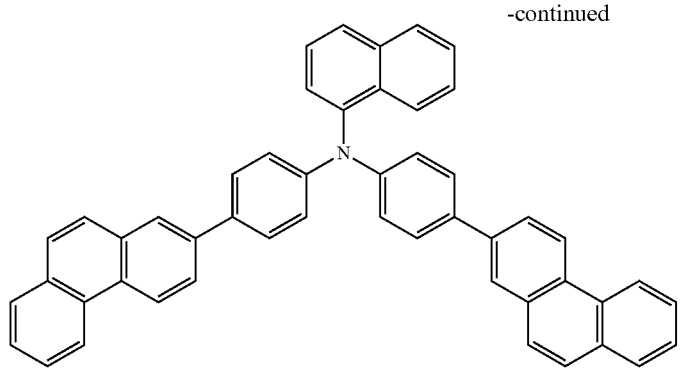
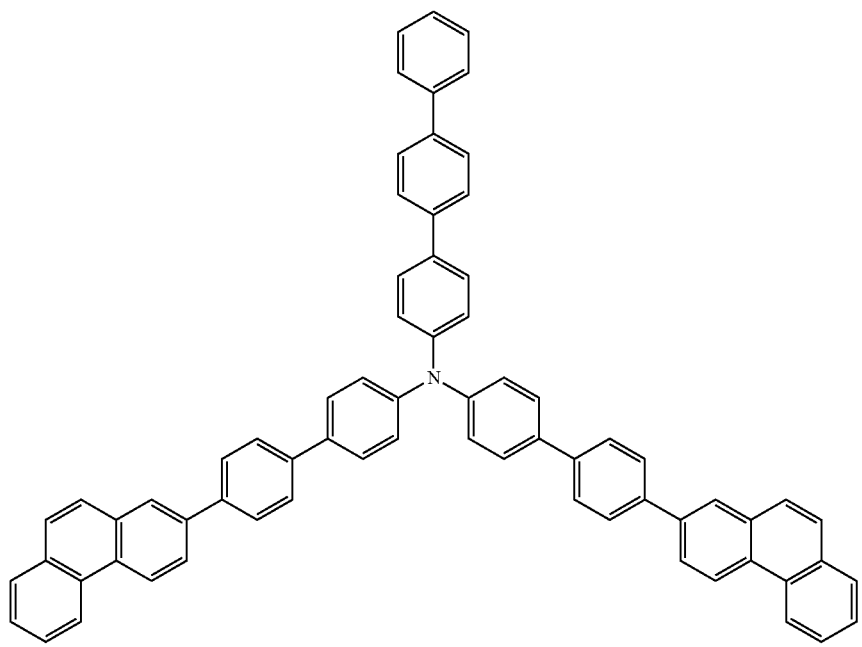
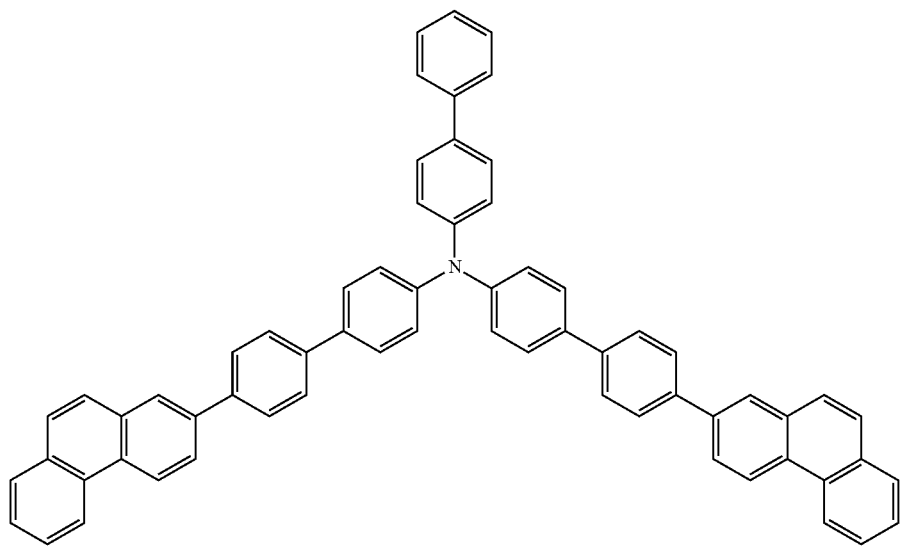

-continued
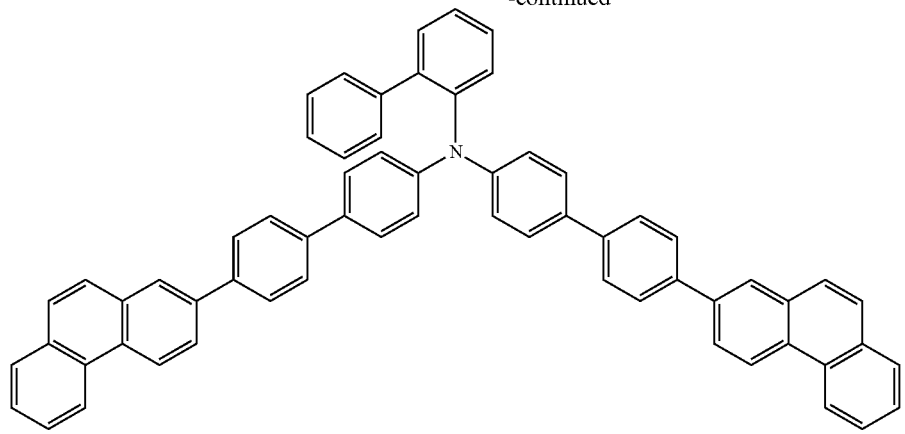
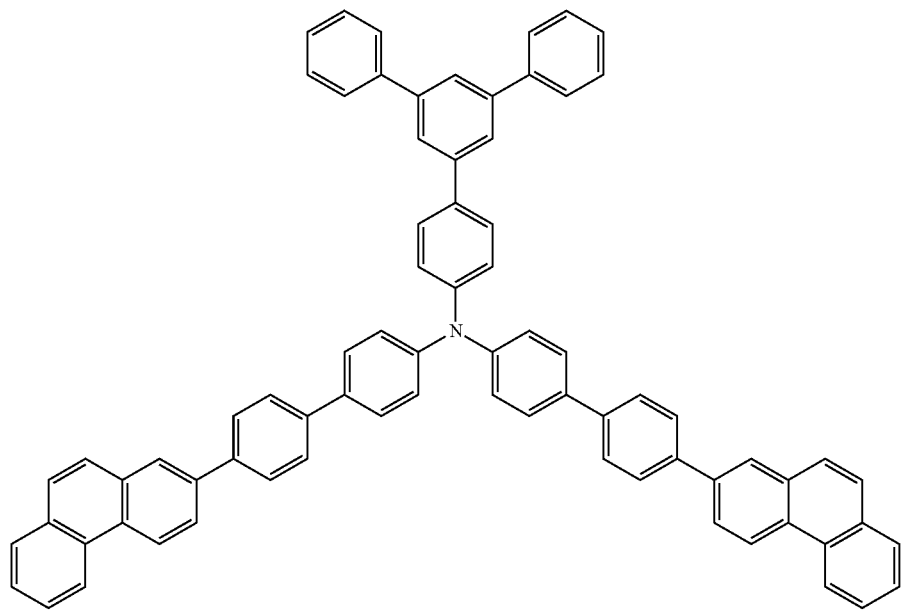
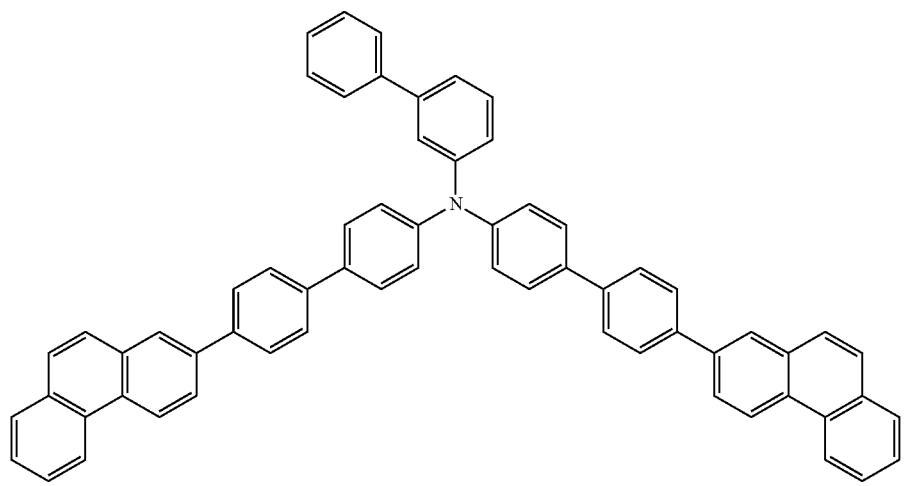

-continued
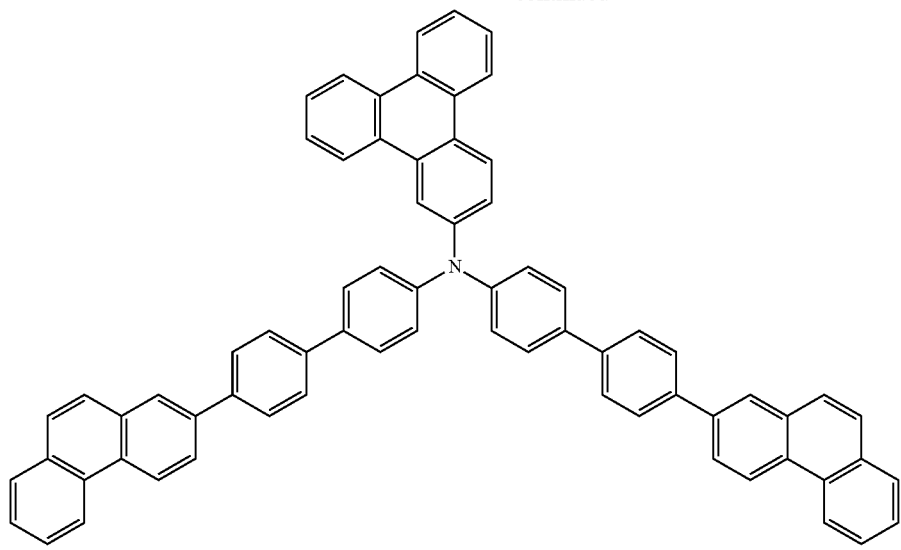
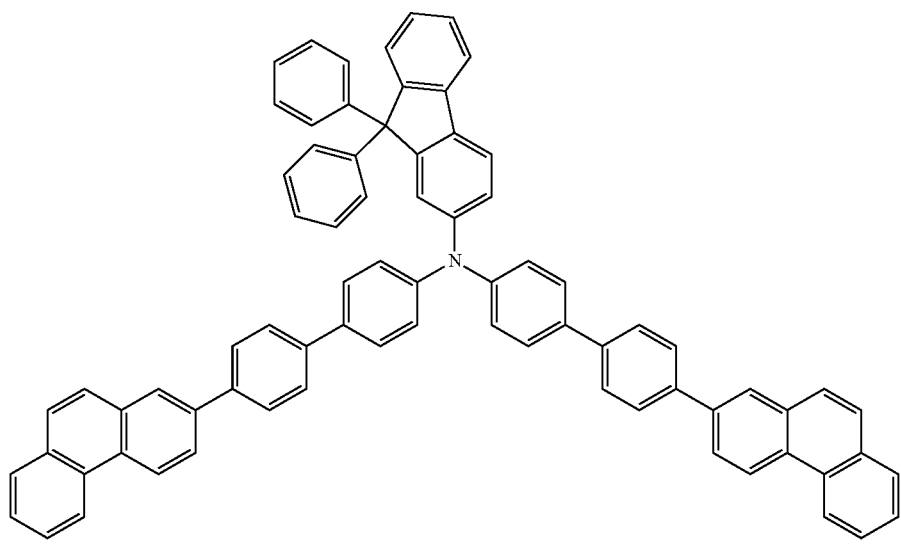
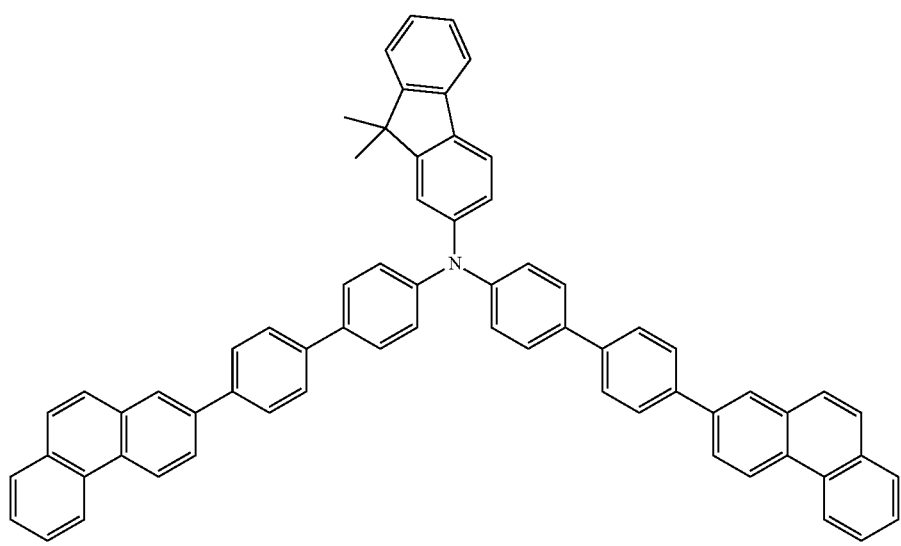

-continued
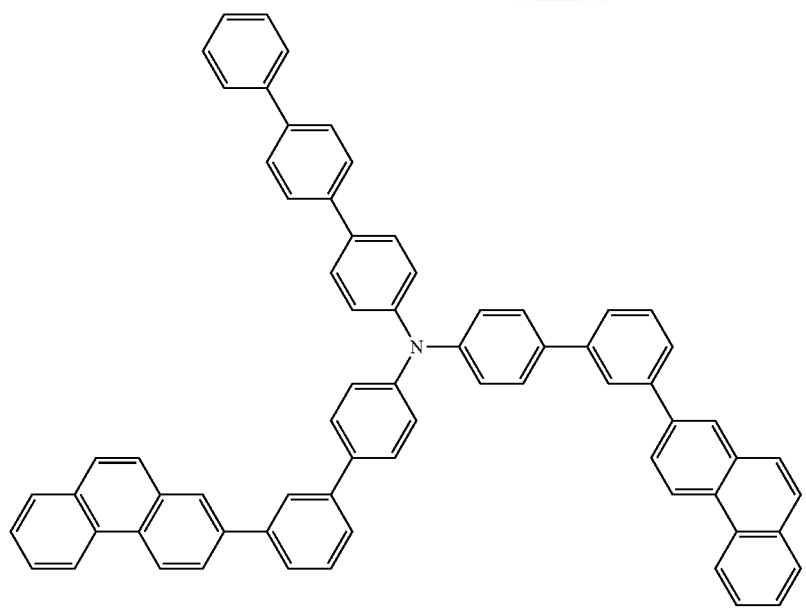
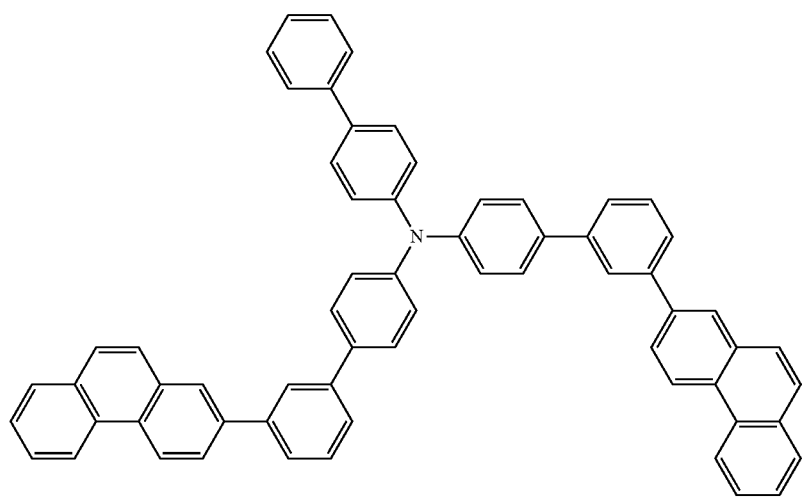
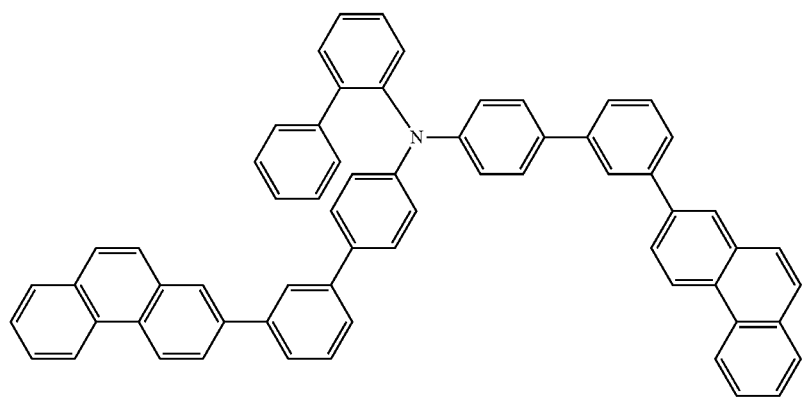

-continued
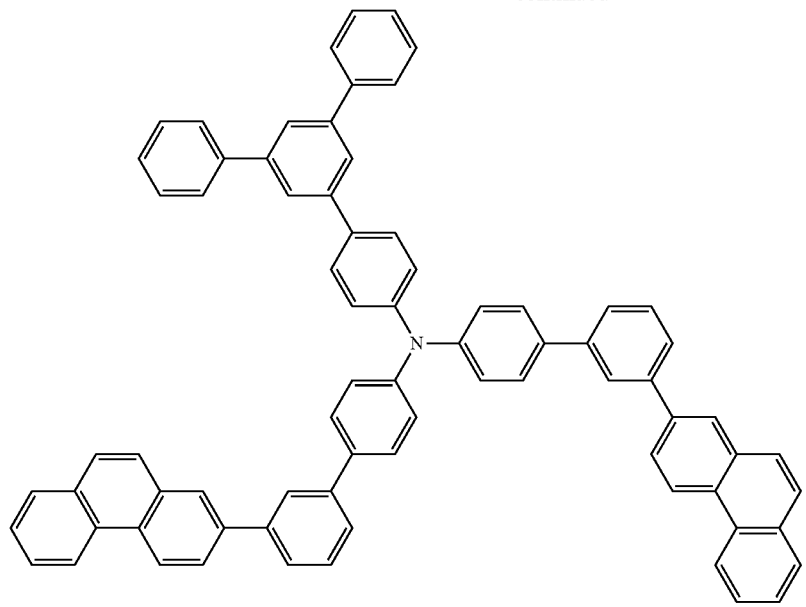
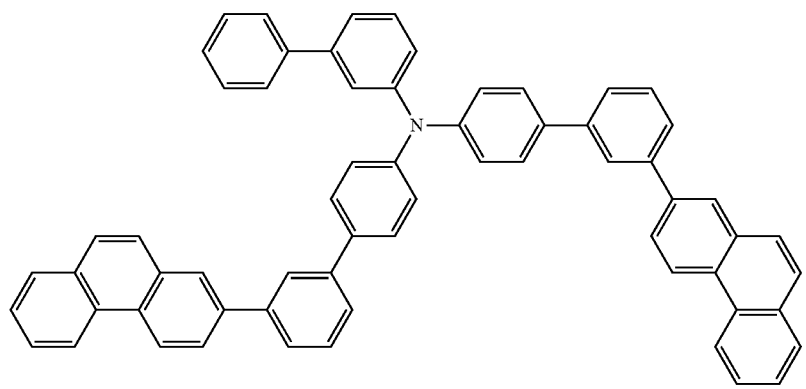
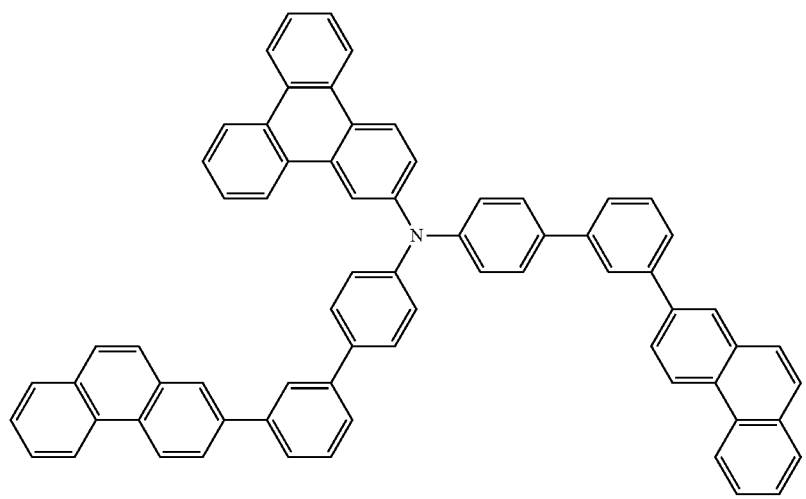

-continued
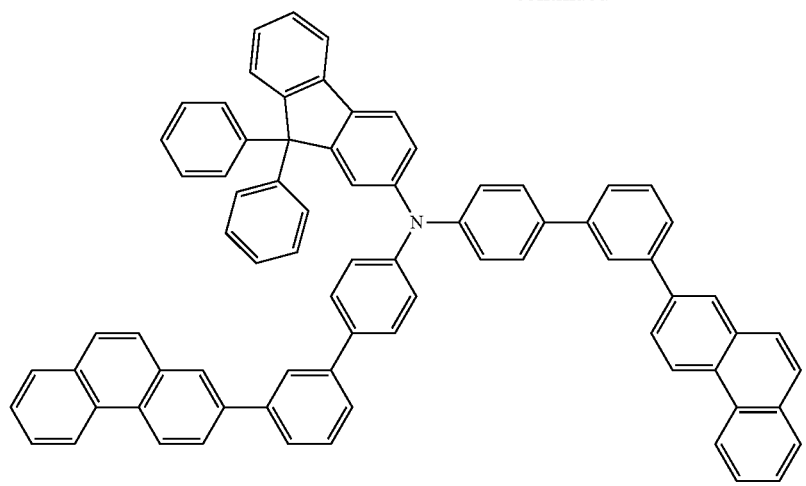
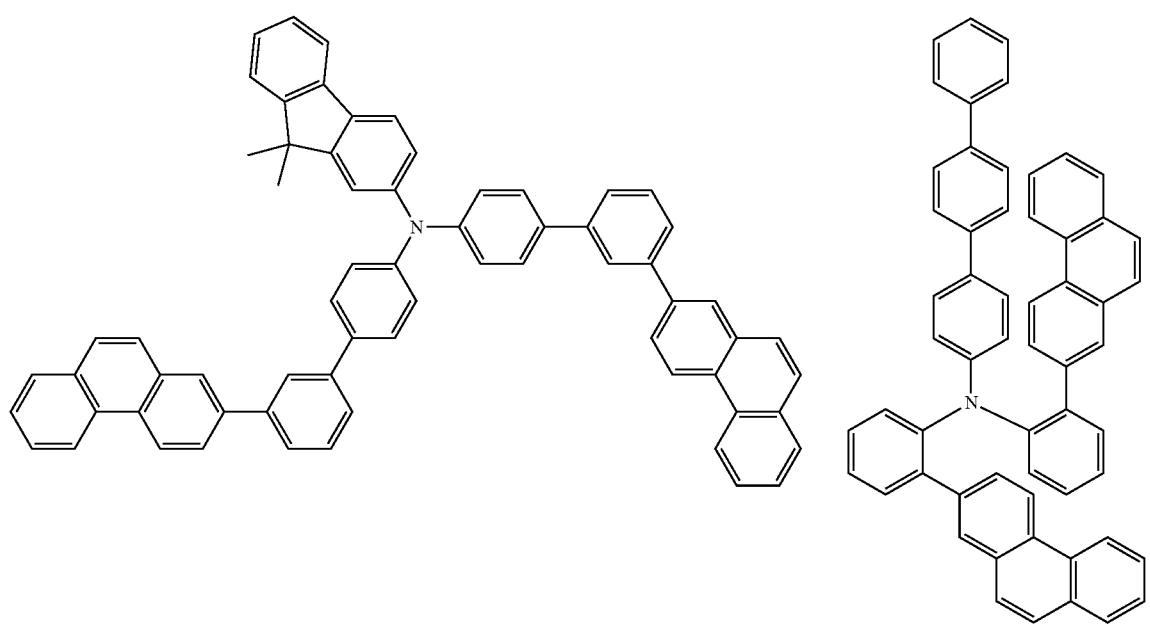
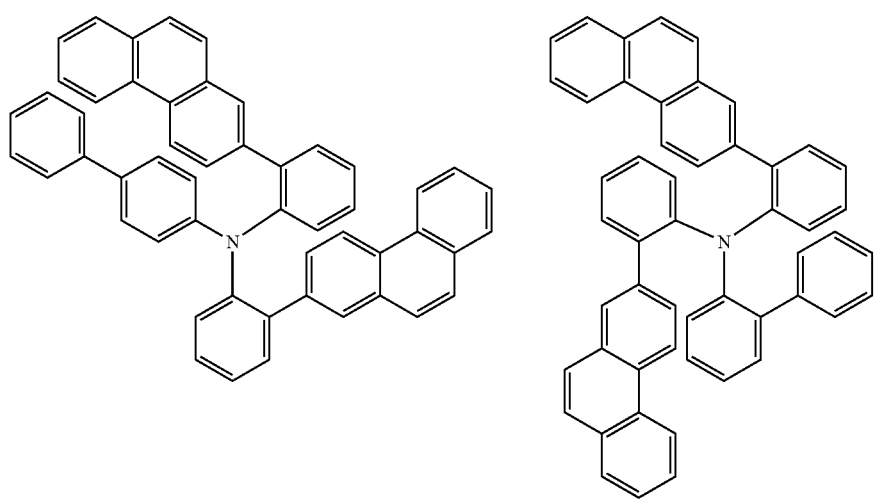

-continued
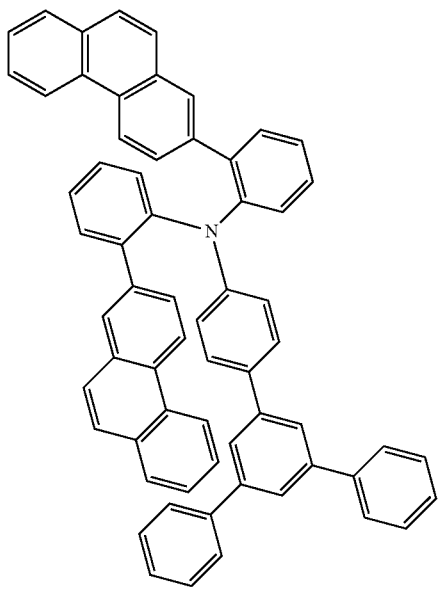 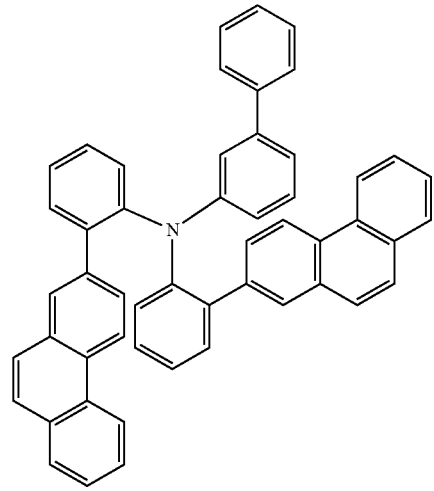
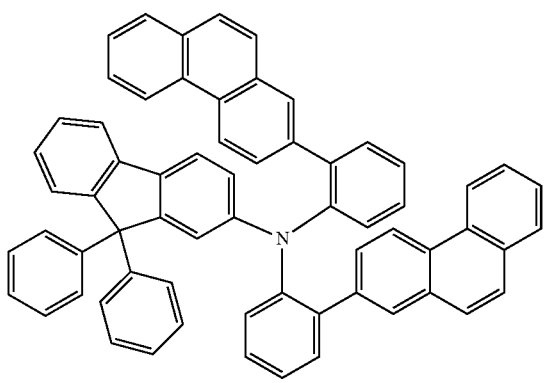 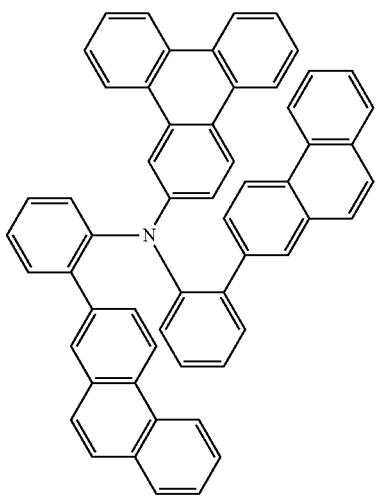
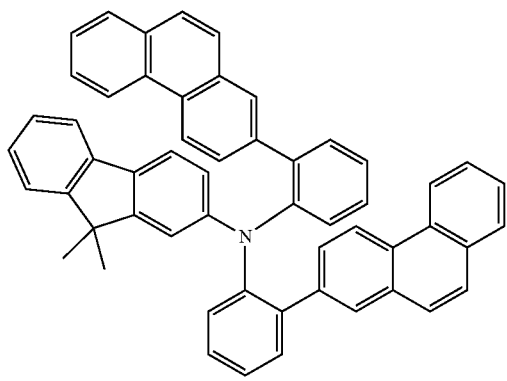

-continued
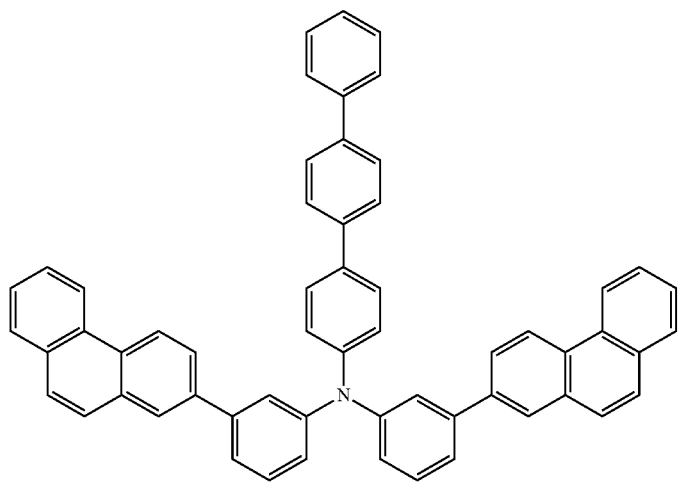
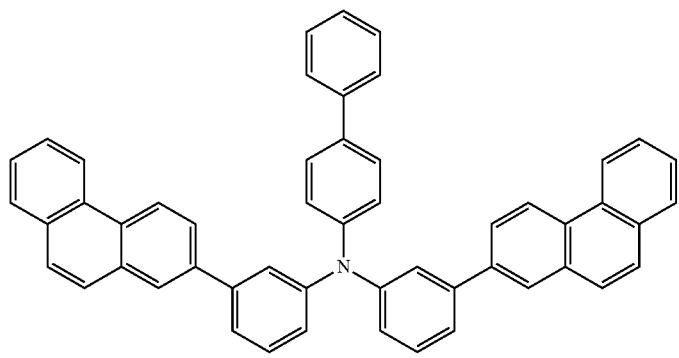
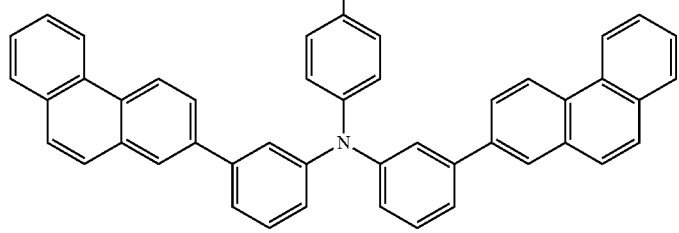
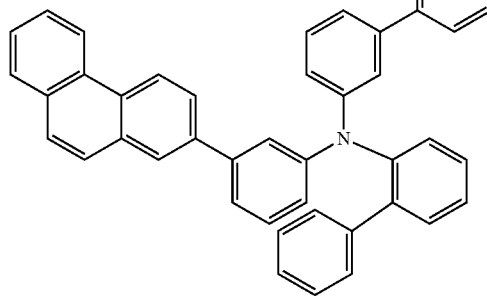

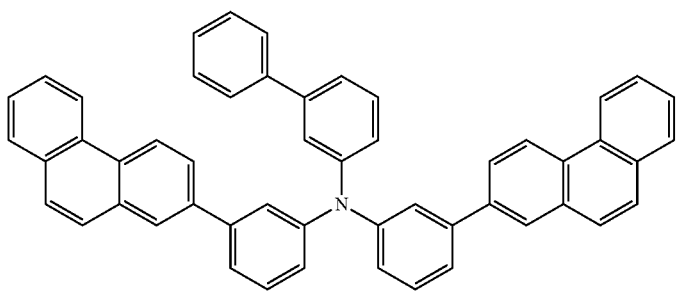
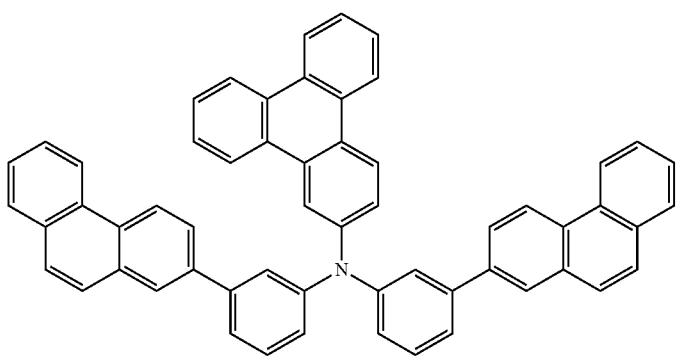
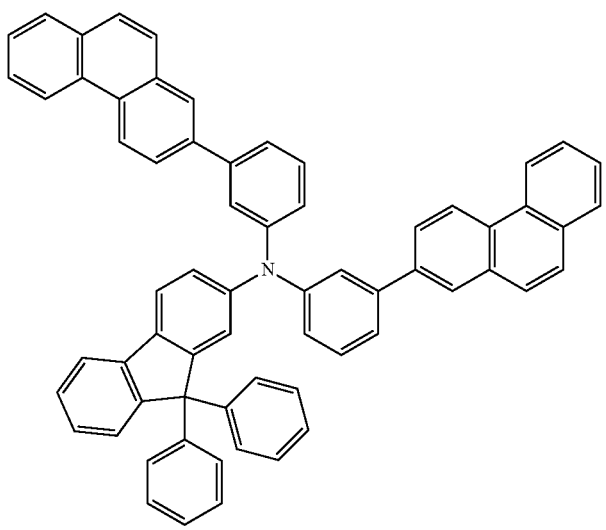
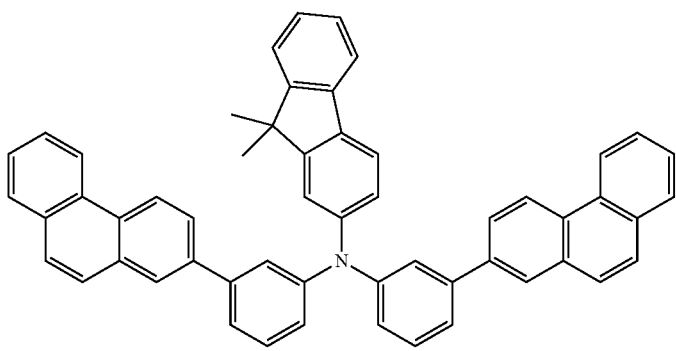

-continued
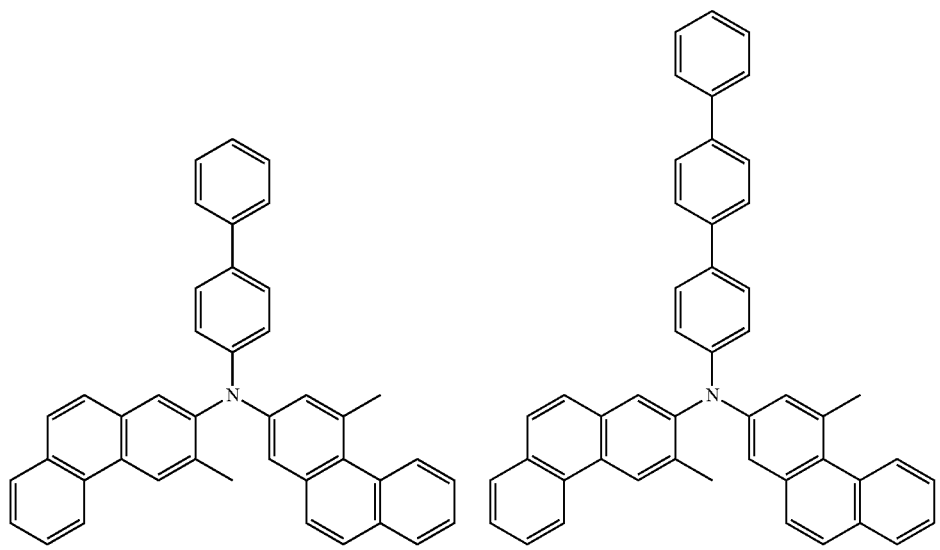
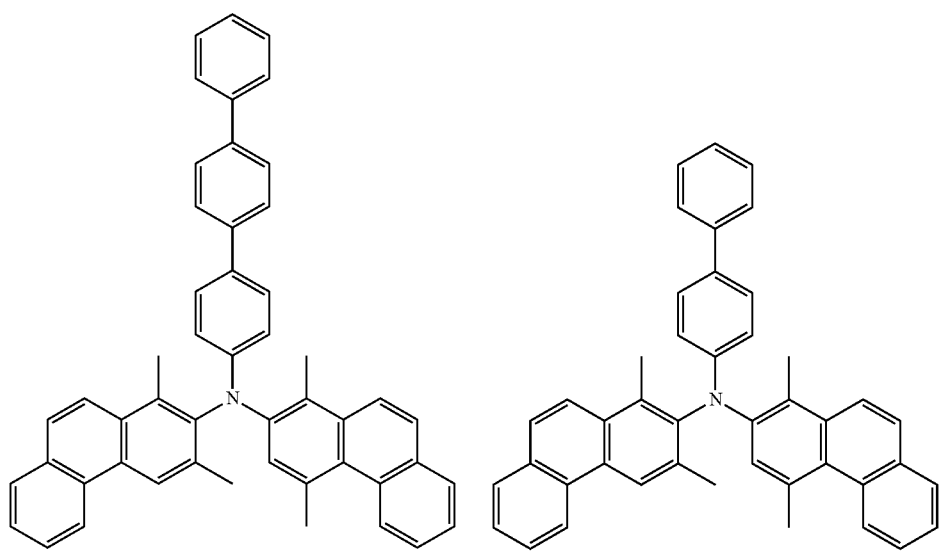
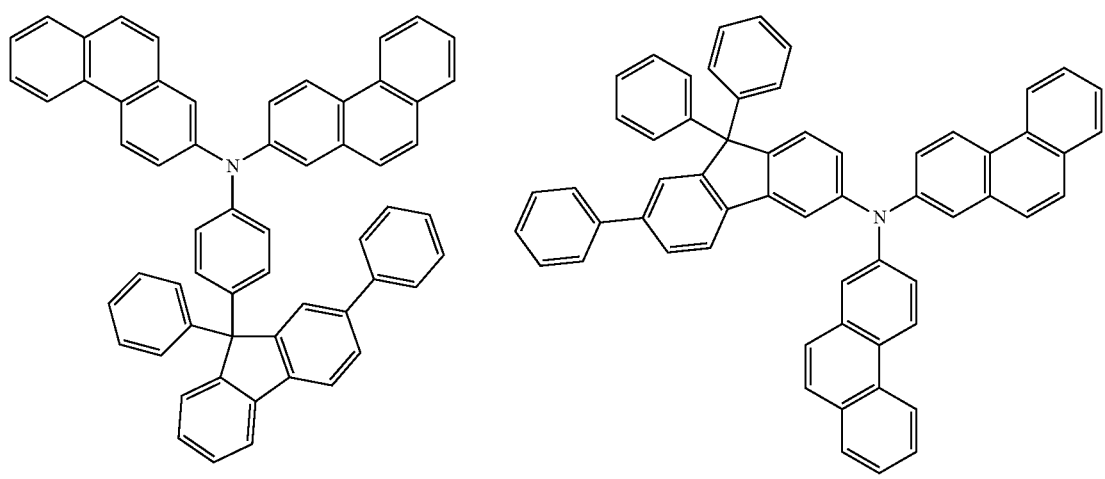

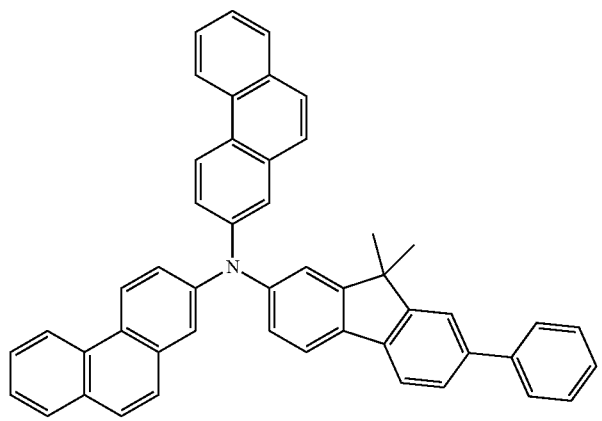
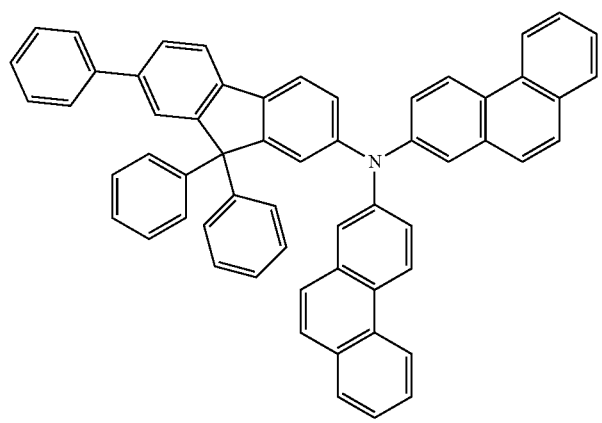
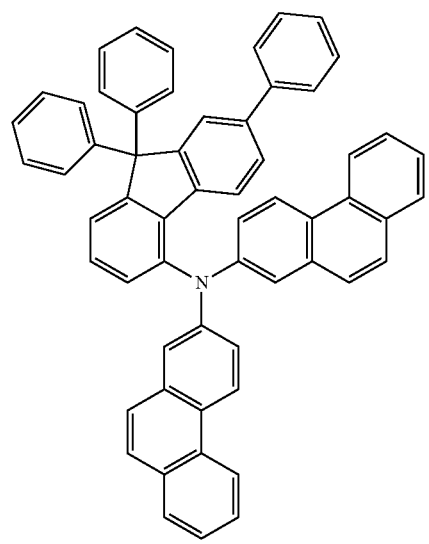
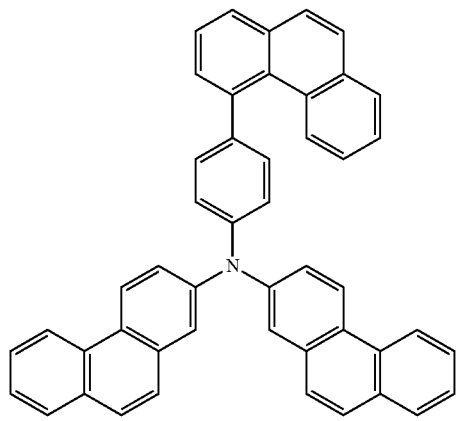
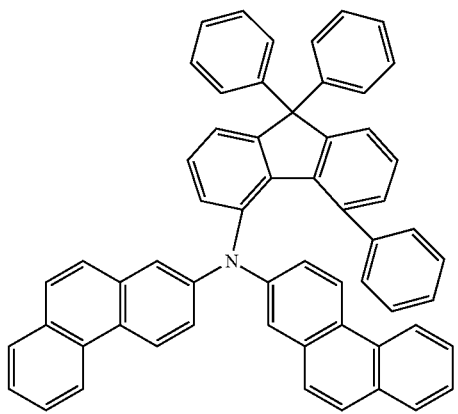

-continued
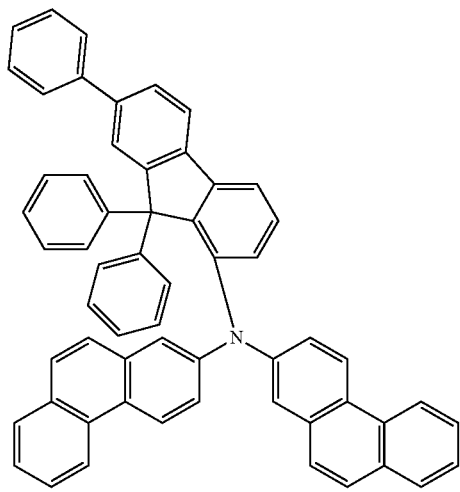
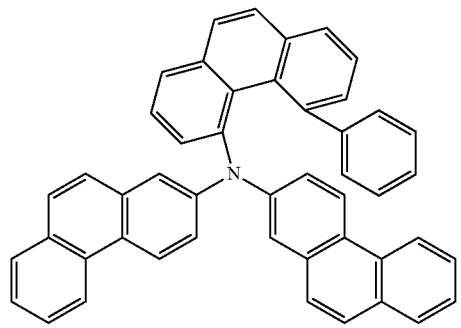
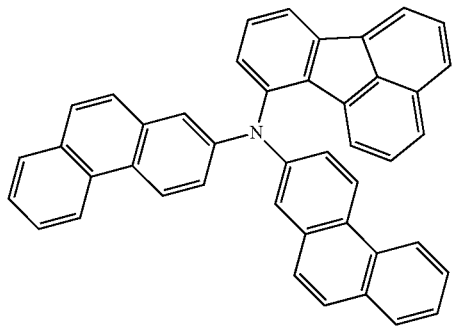
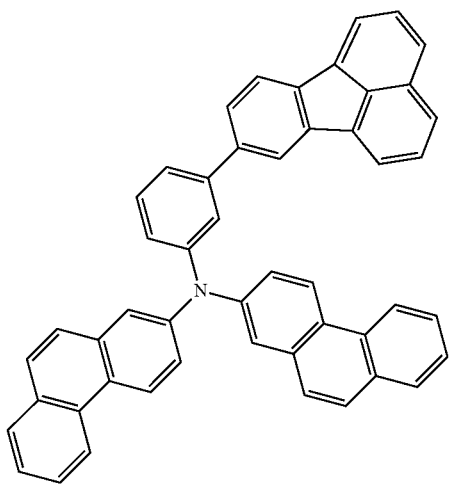
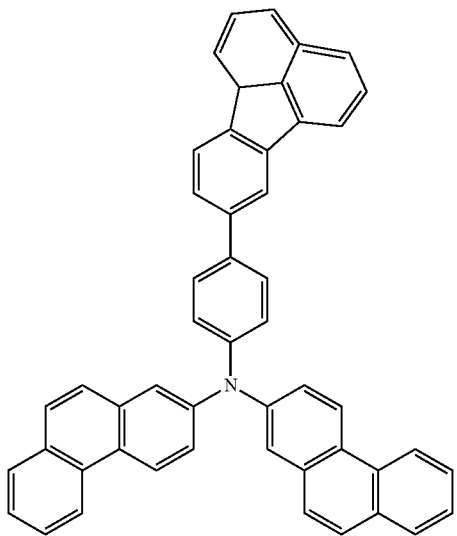
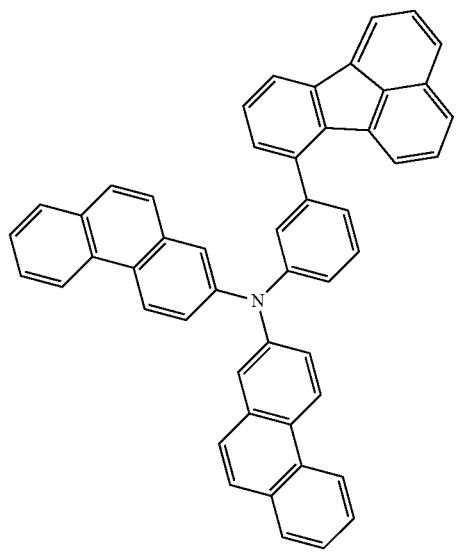

-continued

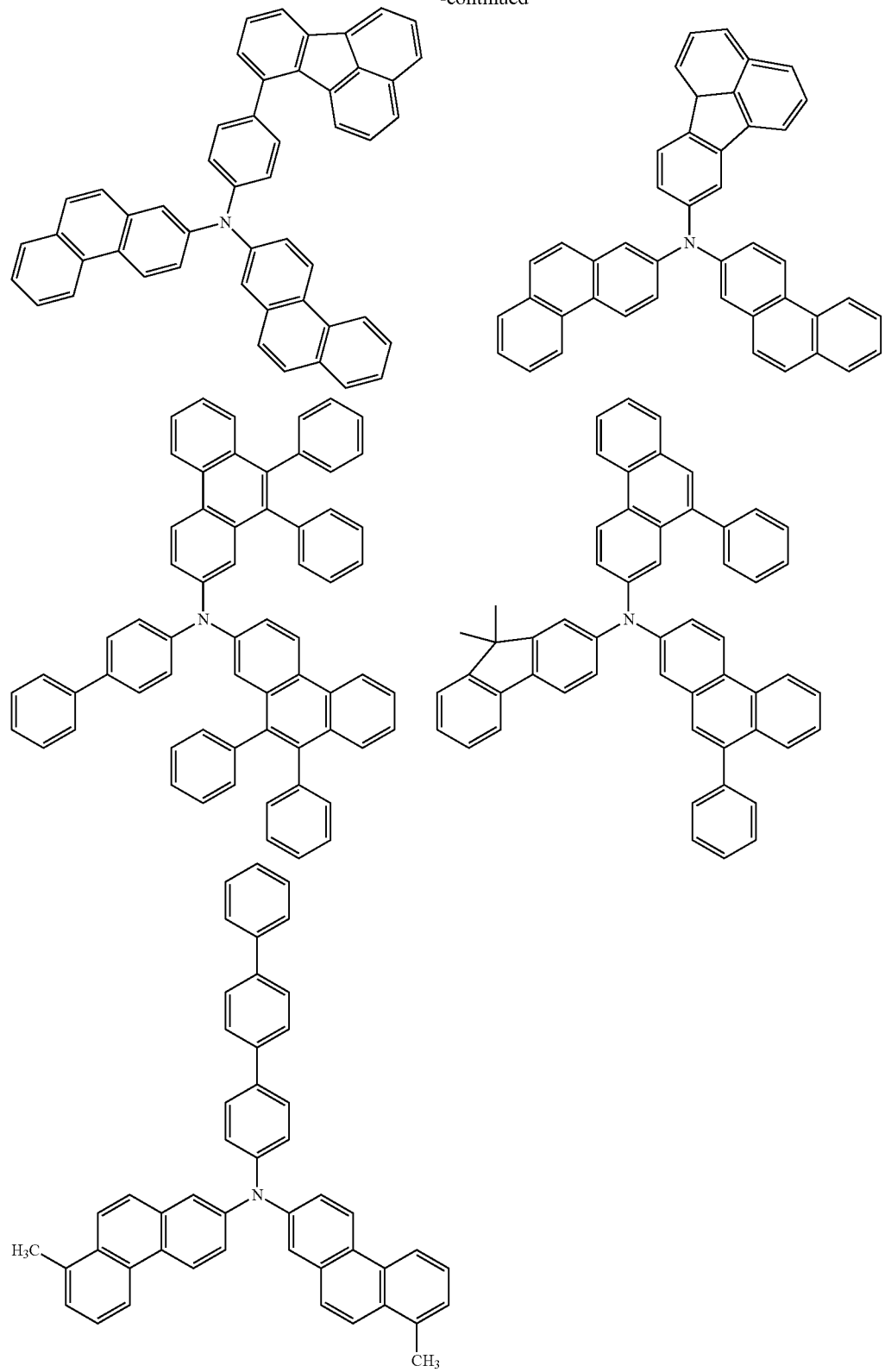

Material for Organic Electroluminescence Devices

The material for organic electroluminescence devices in an aspect of the invention comprises the compound represented by formula (1) ("compound (1)").

The following description related to the compound (1) is equally applicable to any the compounds within formula (1).

The content of the compound (1) in the material for organic electroluminescence devices in an aspect of the invention is, but not particularly limited, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%).

The material for organic EL devices is useful as a material for producing an organic EL device and may be used, for example, in a light emitting layer of a fluorescent emission unit as a host material or a dopant material or in a light emitting layer of a phosphorescent emission unit as a host material. In addition, in either a fluorescent emission unit or a phosphorescent emission unit, the material for organic EL device of the invention is also useful as a material for an anode-side organic thin film layer, for example, a hole transporting layer, a hole injecting layer, and an electron blocking layer, which is formed between an anode and a light emitting layer, and as a material for a cathode-side organic thin film layer, for example, an electron transporting layer, an electron injecting layer, and a hole blocking layer, which is formed between a cathode and a light emitting layer. The anode-side organic thin film layer may be a multilayer comprising two or more layers which may be hole transporting layers. The material for organic EL devices of the invention may be used in any of the two or more hole transporting layers. Thus, the material for organic EL devices of the invention may be used in any of a hole transporting layer closest to a light emitting layer, a hole transporting layer closest to an anode, and a hole transporting layer, between them.

Organic EL Device

The organic EL device in an aspect of the invention will be described below.

The organic EL device comprises an organic thin film layer between a cathode and an anode. The organic thin film layer comprises one or more layers, the organic thin film layer comprises a light emitting layer, and at least one layer of the organic thin film layer comprises the compound (1).

Examples of the organic thin film layer which comprises the compound (1) include an anode-side organic thin film layer formed between an anode and a light emitting layer (hole transporting layer, hole injecting layer, electron blocking layer, exciton blocking layer, etc.), a light emitting layer, a space layer, and a blocking layer, although not limited thereto. The compound (1) is usable in a fluorescent emission unit, for example, as a host material or a dopant material in a light emitting layer, a hole injecting layer material, and a hole transporting layer material. The compound (1) is also usable in a phosphorescent emission unit as a host material in a light emitting layer, a hole injecting layer material and a hole transporting layer material. When the anode-side organic thin film layer comprises two or more hole transporting layers, the compound (1) may be included in any of the hole transporting layers. Namely, the compound (1) may be included in any of the hole transporting layer closest to the light emitting layer, the hole transporting layer closest to the anode, and a hole transporting layer between them.

The organic EL device in an aspect of the invention may be any of a fluorescent or phosphorescent single color emitting device, a white-emitting device of fluorescent-phosphorescent hybrid type, a simple-type emitting device having a single emission unit, and a tandem emitting device having two or more emission units. The "emission unit" referred to herein is the smallest unit for emitting light by the recombination of injected holes and injected electrons, which comprises an organic thin film layer comprising one or more layers, wherein at least one layer is a light emitting layer.

Representative device structures of the simple type organic EL device are shown below:
(1) Anode/Emission Unit/Cathode The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, with the layers in parentheses being optional:

(au) (Hole injecting layer/) Hole transporting layer/Fluorescent emitting layer (/Electron transporting layer);

(bu) (Hole injecting layer/) Hole transporting layer/Phosphorescent emitting layer (/Electron transporting layer);

(cu) (Hole injecting layer/) Hole transporting layer/First fluorescent emitting layer/Second fluorescent emitting layer (/Electron transporting layer);

(du) (Hole injecting layer/) Hole transporting layer/First phosphorescent emitting layer/Second phosphorescent emitting layer (/Electron transporting layer);

(eu) (Hole injecting layer/) Hole transporting layer/Phosphorescent emitting layer/Space layer/Fluorescent emitting layer (/Electron transporting layer);

(fu) (Hole injecting layer/) Hole transporting layer/First phosphorescent emitting layer/Second phosphorescent emitting layer/Space layer/Fluorescent emitting layer (/Electron transporting layer);

(gu) (Hole injecting layer/) Hole transporting layer/First phosphorescent emitting layer/Space layer/Second phosphorescent emitting layer/Space layer/Fluorescent emitting layer (/Electron transporting layer);

(hu) (Hole injecting layer/) Hole transporting layer/Phosphorescent emitting layer/Space layer/First fluorescent emitting layer/Second fluorescent emitting layer (/Electron transporting layer);

(iu) (Hole injecting layer/) Hole transporting layer/Electron blocking layer/Fluorescent emitting layer (/Electron transporting layer);

(ju) (Hole injecting layer/) Hole transporting layer/Electron blocking layer/Phosphorescent emitting layer (/Electron transporting layer);

(ku) (Hole injecting layer/) Hole transporting layer/Exciton blocking layer/Fluorescent emitting layer (/Electron transporting layer);

(lu) (Hole injecting layer/) Hole transporting layer/Exciton blocking layer/Phosphorescent emitting layer (/Electron transporting layer);

(mu) (Hole injecting layer/) First hole transporting layer/Second hole transporting layer/Fluorescent emitting layer (/Electron transporting layer);

(nu) (Hole injecting layer/) First hole transporting layer/Second hole transporting layer/Phosphorescent emitting layer (/Electron transporting layer);

(ou) (Hole injecting layer/) Hole transporting layer/Fluorescent emitting layer/Hole blocking layer (/Electron transporting layer); and (pu) (Hole injecting layer/) Hole transporting layer/Fluorescent emitting layer/Triplet blocking layer (/Electron transporting layer).

The emission color of the fluorescent emitting layer and that of the phosphorescent emitting layer may be different.

For example, the layered structure of the laminated emission unit (fu) may be (Hole injecting layer/) Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode The layered structure of the first emission unit and the second emission unit may be independently selected from, for example, those exemplified above.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. A hole injecting layer or a hole transporting layer 6 (anode-side organic thin film layer) may be disposed between the light emitting layer 5 and the anode 3, and an electron injecting layer or a electron transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10% by mass of zinc oxide, and a film of indium oxide doped with tungsten oxide and zinc oxide is formed by sputtering an indium oxide target doped with 0.5 to 5% by mass of tungsten oxide and 0.1 to 1% by mass of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material). The compound (1) may be used in the hole injecting layer alone or in combination with the following material.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)bipbenyl (DNTPD), 1,3,5-tris[N-(4-diphenylaminophenyl)-N-phenylamino]benzene (DPA3B), 3-[N-(9-phenylcarbazole-3-yl)-N-phenylam- ino]-9-phenylcarbazole (PCzPCA1), ,6-bis[N-(9- phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used in combination with the compound (1):

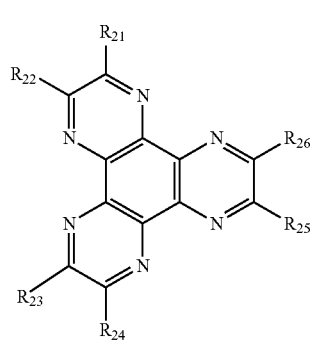

(K)

wherein $R_{21}$ to $R_{26}$ may be the same or different and each of $R_{21}$ to $R_{26}$ is independently a cyano group, —$CONH_2$, a carboxyl group, or —$COOR_{27}$ wherein $R_{27}$ is an alkyl group having 1 to 20 carbon atoms or a cycloalkyl group having 3 to 20 carbon atoms, or $R_{21}$ and $R_{22}$, $R_{23}$ and $R_{24}$, or $R_{25}$ and $R_{26}$ may be bonded to each other to form a group represented by —CO—O—CO—.

$R_{27}$ is a methyl group, an ethyl group, a n-propyl group, an isopropyl group, a n-butyl group, an isobutyl group, a t-butyl group, a cyclopentyl group, or a cyclohexyl group.

Hole Transporting Layer

The hole transporting layer comprises a highly hole transporting material (hole transporting material). The compound (1) may be used in the hole transporting layer alone or in combination with the following material.

Examples of the hole transporting material include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4''-tris(N,N-diphenylamino)triphenylamine (TDATA), 4,4',4''-tris[N-(3-methylphenyl)-N-phenylamino]triphenylamine (MTDATA), and 4,4'-[N-(spino-9,9'-bifluorene-2-yl)-N-phenylamino]biphenyl (BSPB). The above compounds have a hole mobility of $10^{-6}$ $cm^2/Vs$ or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macromolecular compound, such as poly(N-vinylcarbazole) (PVK) and poly(4-vinyltriphenylamine) (PVTPA).

Compounds other than those mentioned above are also usable if their hole transporting ability is higher than their electron transporting ability. The layer comprising a highly hole-transporting material may be a single layer or a laminate of two or more layers each comprising the compound mentioned above. For example, the hole transporting layer may be a two-layered structure of a first hole transporting layer (anode side) and a second hole transporting layer (cathode side). In this case, the compound (1) may be used in either of the first hole transporting layer and the second hole transporting layer. In an embodiment of the invention, the compound (1) is preferably used in the first hole transporting layer. In another embodiment of the invention, the compound (1) is preferably used in the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound which emits light from a singlet excited state, and the phosphorescent emitting material is a compound which emits light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PC-ABPhA), N-(9,10-diphenyl-2-anthryl)-N,N',N''-triphenyl-1,4-phenylenediamine (2DPAPA), N-[9,10-bis(1,1'-biphenyl-2-yl)-2-anthryl]-N,N',N''-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2'] iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) (Ir(ppy)₃), bis(2-phenylpyridinato-N,C2')iridium(III) acetylacetonato (Ir(ppy)₂(acac)), bis(1,2-diphenyl-1H-benzimidazolato)iridium(III) acetylacetonato (Ir(pbi)₂(acac)), and bis(benzo[h]quinolinato)iridium(III) acetylacetonato (Ir(bzq)₂(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)₂(acac)), bis(1-phenylisoquinolinato-N,C2')iridium(III) acetylacetonato (Ir(piq)₂(acac)), (acetylacetonato)bis[2,3-bis(4-fluorophenyl)quinoxalinato]iridium(III) (Ir(Fdpq)₂(acac)), and 2,3,7,8,12,13,17,18-octaethyl-21H-porphyrin platinum(II) (PtOEP).

A rare earth metal complex, such as tris(acetylacetonato)(monophenanthroline)terbium(III) (Tb(acac)₃(Phen)), tris(1,3-diphenyl-1,3-propanedionato)(monophenanthroline)europium(III) (Eu(DBM)₃(Phen)), and tris[1-(2-thenoyl)-3,3,3-trifluoroacetonato](monophenanthroline)europium(III) (Eu(TTA)₃(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). The compound (1) of the invention and other various compounds may be used as the host material. The host material preferably has a lowest unoccupied molecular orbital level (LUMO level) higher than that of the dopant material and a highest occupied molecular orbital level (HOMO level) lower than that of the dopant material.

The host material may include, for example,
(1h) a metal complex, such as an aluminum complex, a beryllium complex, and a zinc complex;
(2h) a heterocyclic compound, such as an oxadiazole derivative, a benzimidazole derivative, and a phenanthroline derivative;
(3h) a fused aromatic compound, such as a carbazole derivative, an anthracene derivative, a phenanthrene derivative, a pyrene derivative, and a chrysene derivative; and
(4h) an aromatic amine compound, such as a triarylamine derivative and a fused aromatic polycyclic amine derivative.

Examples thereof include:
a metal complex, such as tris(8-quinolinolato)aluminum(III) (Alq), tris(4-methyl-8-quinolinolato)aluminum(III) (Almq₃), bis(10-hydroxybenzo[h]quinolinato)beryllium(II) (BeBq₂), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1P), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4"-bis[N-(spiro-9,9'-bifluorene-2-yl)-N-phenylamino]biphenyl (BSPB). The host material may be used alone or in combination of two or more.

Electron Transporting Layer

The electron transporting layer comprises a highly electron-transporting material (electron transporting material). Examples thereof are:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato)aluminum (Almq₃), bis(10-hydroxybenzo[h]quinolinato)beryllium (BeBq₂), bis(2-methyl-8-quinolinato)(4-phenylphenolato)aluminum (III) (BAlq), bis(8-quinolinato)zinc(II) (Znq), bis[2-(2-benzoxazolyl)phenolato]zinc(II) (ZnPBO), and bis[2-(2-benzothiazolyl)phenolato]zinc (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of 10⁻⁶ cm²/Vs or more. Materials other than those mentioned above are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer (exciton blocking layer), may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer. The compound (1) of the invention is also suitable as the material for the electron blocking layer and the triplet blocking layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage to reduce the efficiency.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples and comparative examples. It should be noted that the scope of the invention is not limited to the following examples.

Synthesis Example 1 (Synthesis of Compound H1)

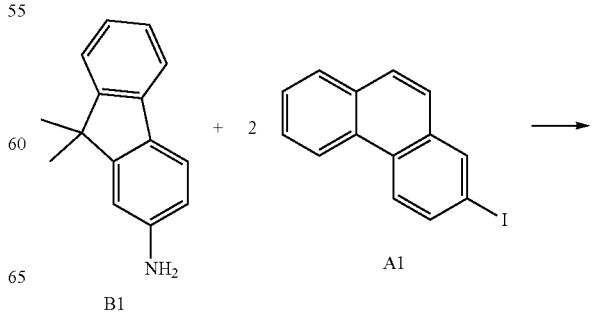

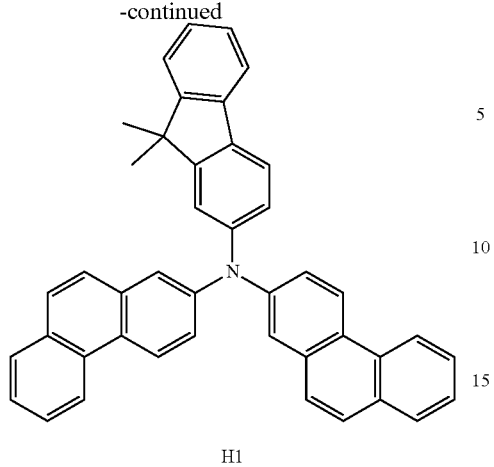

H1

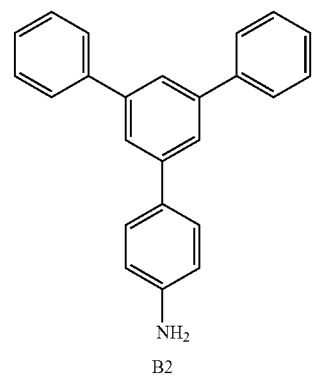

B2

Under argon atmosphere, the compound B1 (2.09 g, 10.0 mmol), the compound A1 synthesized by the method described in WO 2009/116628 (6.69 g, 20.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (3.84 g, 40.0 mmol), and anhydrous xylene (100 mL) were successively mixed, and the resultant mixture was refluxed under heating for 7 h.

After cooling the reaction liquid to room temperature, the insolubles were removed by filtration, and the organic solvent was evaporated off under reduced pressure. The obtained residue was purified by silica gel column chromatography to obtain the compound H1 (3.65 g, 65% yield).

The result of LC-MS (Liquid Chromatography-Mass Spectrometry) analysis of the compound H1 is shown below.

LC-MS: called for C43H31N=561,
found m/z=561 (M+, 100)

Intermediate Synthesis Example 1: Synthesis of Compound B2

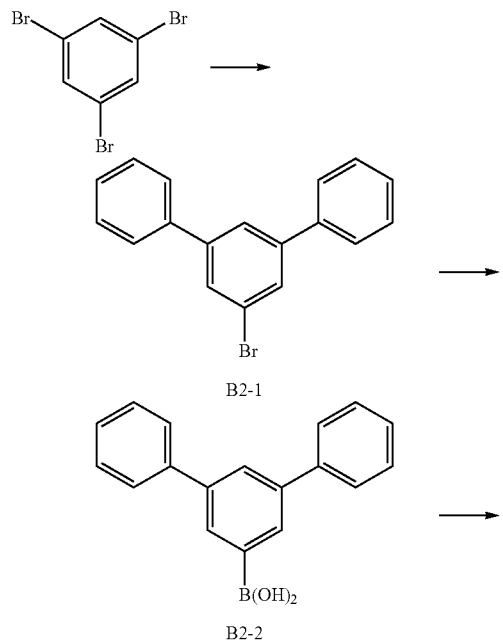

(1-1) Synthesis of Intermediate B2-1

Under argon atmosphere, a mixture of 1,3,5-tribromobenzene (1000 g, 3.18 mol), phenylboronic acid (775 g, 6.35 mol), tetrakis(triphenylphosphine)palladium(0) (147 g, 128 mmol), sodium carbonate (2021 g, 19.1 mol), water (17 L), and DME (17 L) was stirred at 77° C. for 16 h. After cooling to room temperature and adding water, the reaction liquid was extracted with toluene. The toluene layer was concentrated under reduced pressure. The obtained residue was purified by silica gel column chromatography to obtain the compound B2-1 (342 g, 35% yield).

(1-2) Synthesis of Intermediate B2-2

Under argon atmosphere, the intermediate B2-1 (342 g, 1.11 mol) was dissolved in tetrahydrofuran (4.25 L) and cooled to −68° C. After adding a 1.59 M hexane solution of n-butyllithium (850 mL), the mixture was stirred at −68° C. for one hour. After adding triisopropyl borate (624 g, 3.32 mol), the reaction liquid was stirred at room temperature for 16 h. After adding water, the reaction liquid was extracted with toluene, and the toluene layer was concentrated under reduced pressure. The obtained residue was purified by recrystallization to obtain the intermediate B2-2 (1.77 g, 58% yield).

(1-3) Synthesis of Compound B2

Under argon atmosphere, a mixture of the intermediate B2-2 (177 g, 0.65 mol), 4-bromoaniline (117 g, 0.68 mol), tetrakis(triphenylphosphine)palladium(0) (14.9 g, 12.9 mmol), sodium carbonate (205 g, 1.93 mol), water (950 mL), toluene (1800 mL), and ethanol (600 mL) was stirred at 75° C. for 16 h. The reaction liquid was cooled to room temperature, and the organic layer was washed with water and concentrated under reduced pressure. The obtained residue was purified by silica gel column chromatography to obtain the compound B2 (104 g, 51% yield).

Synthesis Example 2 (Synthesis of Compound H2)

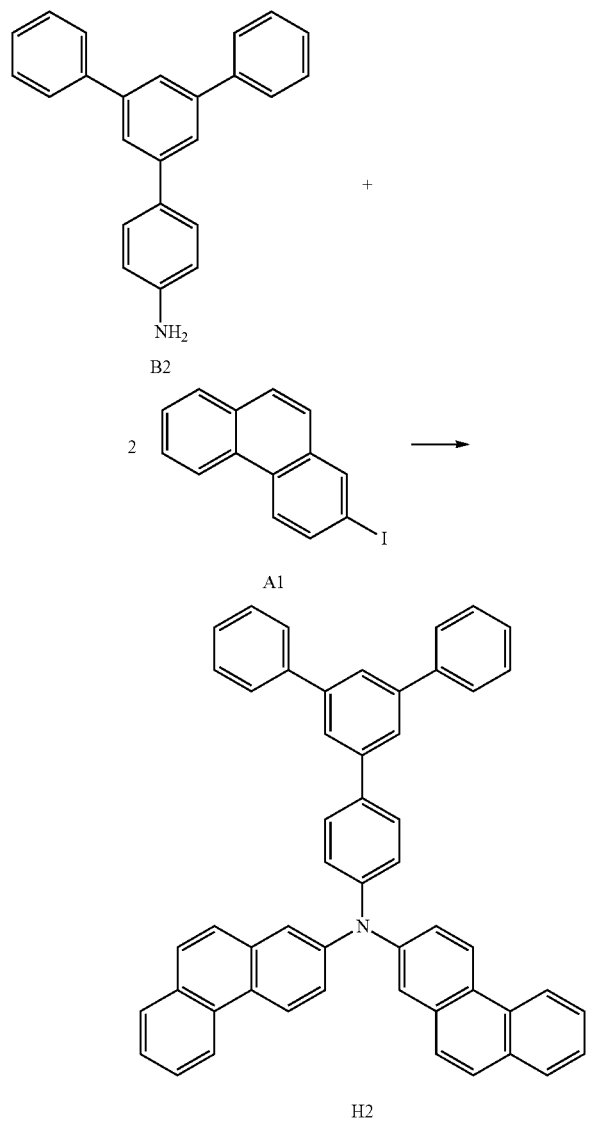

Under argon atmosphere, the compound B2 (3.21 g, 10.0 mmol), the compound A1 synthesized by the method described in WO 2009/116628 (6.69 g, 20.0 mmol), tris(dibenzylideneacetone)dipalladium (195 mg, 0.200 mmol), 2-dicyclohexylphosphino-2',6'-dimethoxybiphenyl (328 mg, 0.800 mmol) sodium t-butoxide (3.84 g, 40.0 mmol), and anhydrous xylene (100 mL) were successively mixed, and the resultant mixture was refluxed under heating for 8 h.

After cooling the reaction liquid to room temperature, the insolubles were removed by filtration, and the organic solvent was evaporated off under reduced pressure. The obtained residue was purified by silica gel column chromatography to obtain the compound H2 (5.39 g, 80% yield).

The result of LC-MS (Liquid Chromatography-Mass Spectrometry) analysis of the compound H2 is shown below.

LC-MS: calcd for C52H35N=673, found m/z=673 (M+, 100)

Intermediate Synthesis Example 2 (Synthesis of Compound A2)

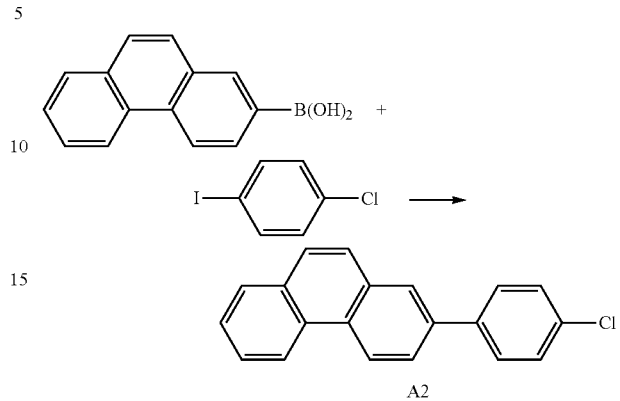

Under argon atmosphere, phenanthrene-2-boronic acid synthesized by the method described in WO 2009/116628 (11.1 g, 50 mmol), 1-chloro-4-iodobenzene (11.9 g, 50 mmol), tetrakis(triphenylphosphine)palladium(0) (1.16 g, 1 mmol), toluene (200 mL), and a 2 M aqueous solution of sodium carbonate (100 mL) were successively mixed, and the resultant mixture was refluxed under heating for 8 h. After cooling to room temperature, the reaction solution was extracted with toluene. The aqueous layer was removed, and the organic layer was successively washed with water and a saturated brine and then dried over magnesium sulfate. After removing the magnesium sulfate by filtration, the organic layer was concentrated. The obtained residue was purified by silica gel column chromatography to obtain the compound A2 (12.9 g, 89% yield).

Synthesis Example 3 (Synthesis of Compound H3)

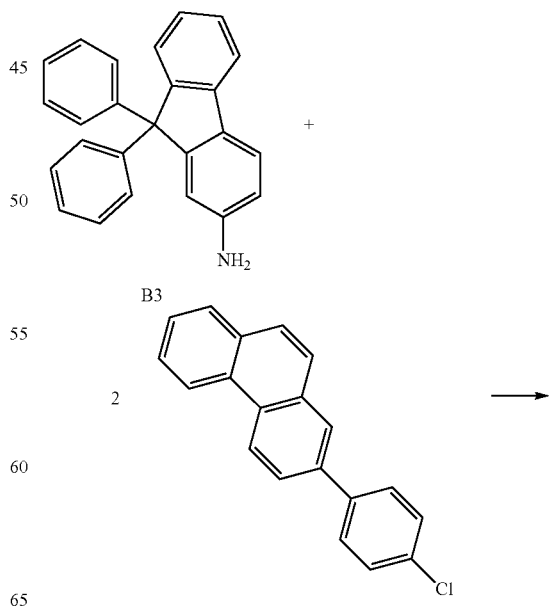

77
-continued

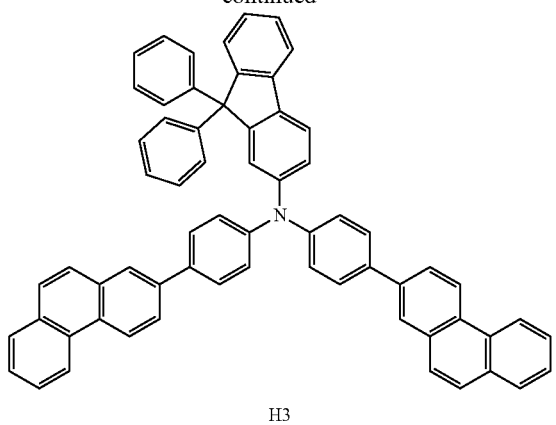

H3

Under argon atmosphere, the compound B3 (3.33 g, 10.0 mmol), the compound A2 (5.96 g, 20.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (3.84 g 40.0 mmol), and anhydrous xylene (100 mL) were successively mixed, and the resultant mixture was refluxed under heating for 8 h.

After cooling the reaction liquid to room temperature, the insolubles were removed by filtration, and the organic solvent was evaporated off under reduced pressure. The obtained residue was purified by silica gel column chromatography to obtain the compound H3 (6.45 g, 77% yield).

The result of LC-MS (Liquid. Chromatography Mass Spectrometry) analysis of the compound H3 is shown below.

LC-MS: calcd for C65H43N=837,
found m/z=837 (M+, 100)

Intermediate Synthesis Example 3 (Synthesis of Compound 3)

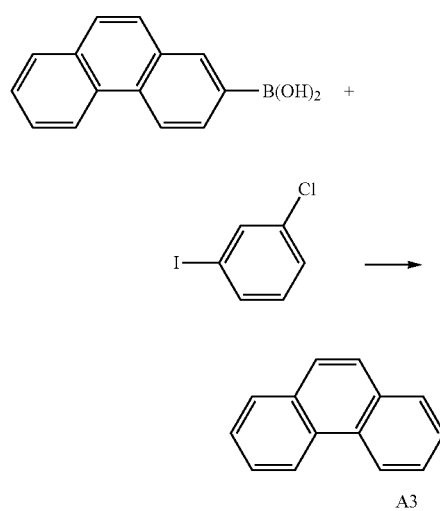

A3

The compound A3 was synthesized in the same manner as in Intermediate Synthesis Example 2 except for using 1-chloro-3-iodobenzene in place of 1-chloro-4-iodobenzene.

78
Synthesis Example 4 (Synthesis of Compound H4)

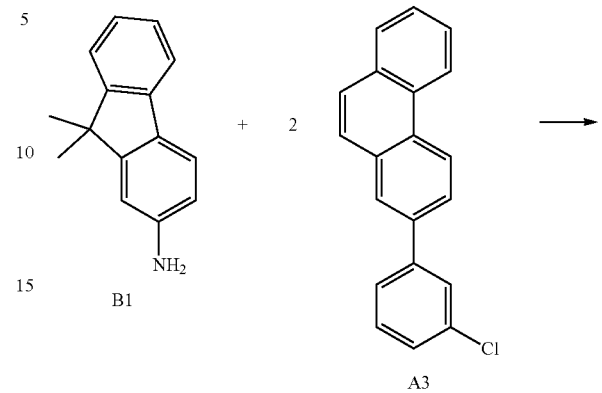

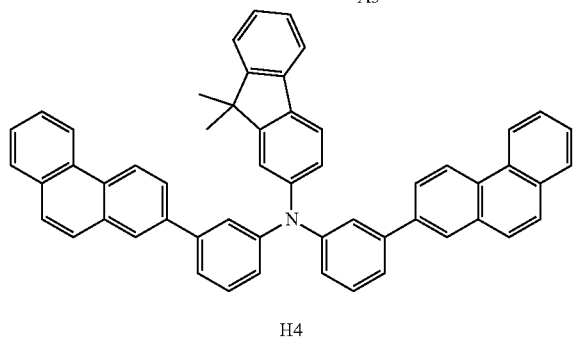

H4

Under argon atmosphere, the compound B1 (2.09 g, 10.0 mmol), the compound A3 (3.96 g, 20.0 mmol), tris(dibenzylideneacetone)dipalladium (195 mg, 0.200 mmol), 2-dicyclohexylphosphino-2',6'-dimethoxybiphenyl (328 mg 0.800 mmol), sodium t-butoxide (3.84 g, 40.0 mmol), and anhydrous xylene (100 mL) were successively mixed, and the resultant mixture was refluxed under heating for 7 h.

After cooling the reaction liquid to room temperature, the insolubles were removed by filtration, and the organic solvent was evaporated off under reduced pressure. The obtained residue was purified by silica gel column chromatography to obtain the compound H4 (3.93 g, 55% yield).

The result of LC-MS (Liquid Chromatography-Mass Spectrometry) analysis of the compound H4 is shown below.
LC-MS: calcd for C55H39N=713,
found m/z=713 (M+, 100)

Synthesis Example 5 (Synthesis of Compound H5)

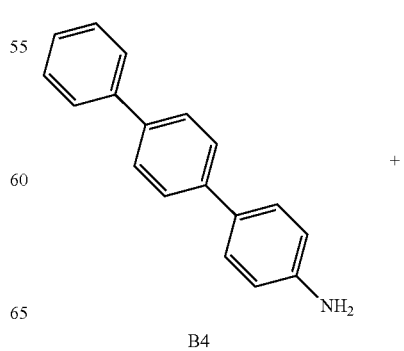

B4

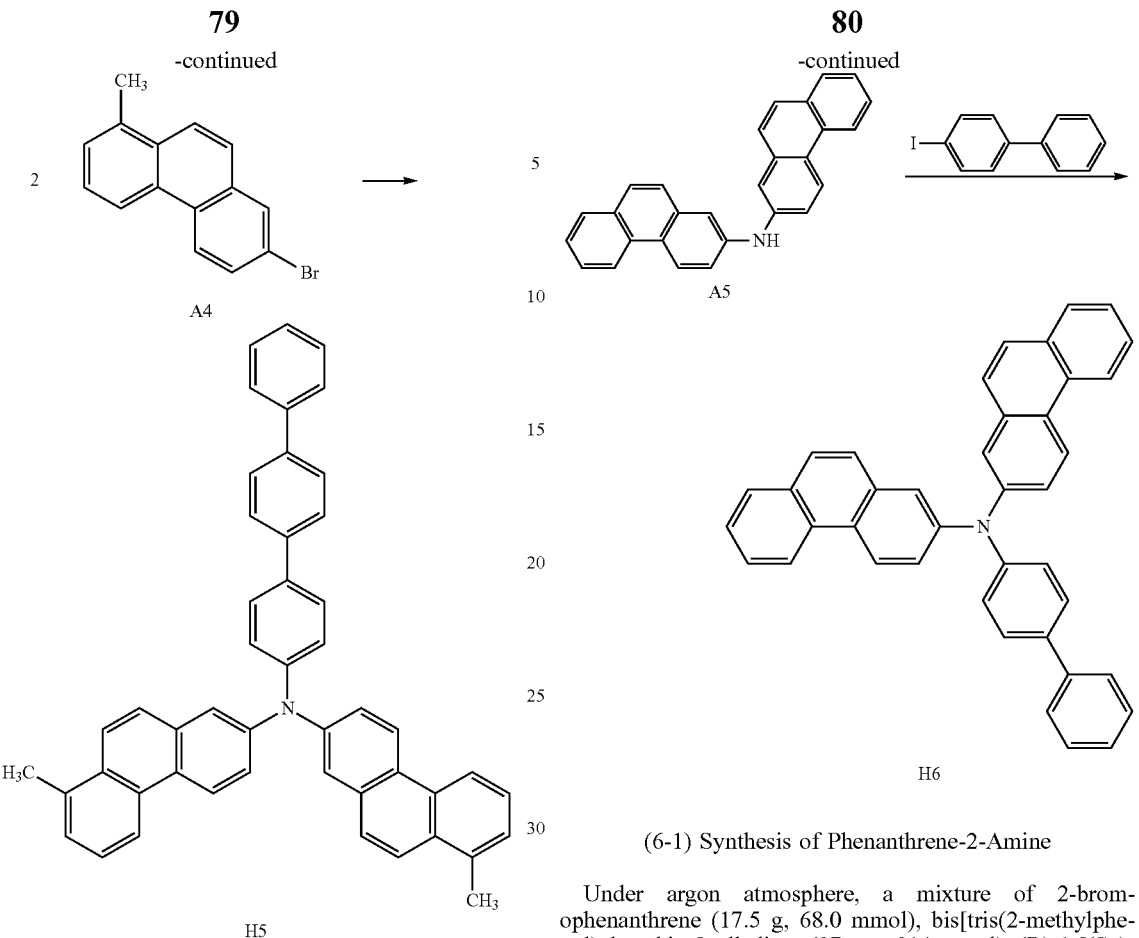

Under argon atmosphere, the compound B4 (2.45 g, 10.0 mmol), the compound A4 (5.42 g, 20.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (3.84 g, 40.0 mmol), and anhydrous xylene (100 mL) were successively mixed, and the resultant mixture was refluxed under heating for 6 h.

After cooling the reaction liquid to room temperature, the insolubles were removed by filtration, and the organic solvent was evaporated off under reduced pressure. The obtained residue was purified by silica gel column chromatography to obtain the compound H5 (3.00 g, 48% yield).

The result of LC-MS (Liquid Chromatography-Mass Spectrometry) analysis of the compound H5 is shown below.
LC-MS: calcd for C48H35N=625,
found m/z=625 (M+, 100)

Synthesis Example 6 (Synthesis of Compound H6)

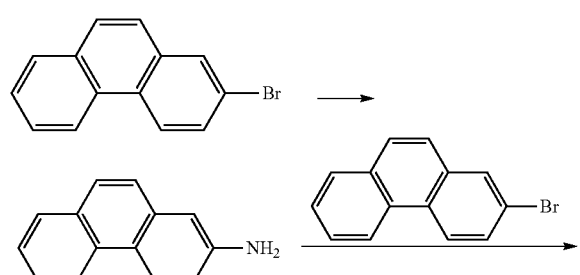

(6-1) Synthesis of Phenanthrene-2-Amine

Under argon atmosphere, a mixture of 2-bromophenanthrene (17.5 g, 68.0 mmol), bis[tris(2-methylphenyl)phosphine]palladium (97 mg, 014 mmol), (R)-1-[(S$_P$)-2-(dicyclohexylphosphino)ferrocenyl]ethyldi-tert-butylphosphine (75 mg, 014 mmol), ammonium sulfate (13.5 g, 102 mmol), sodium t-butoxide (29.4 g, 306 mmol), and dioxane (340 mL) was refluxed under heating for 5 h. After cooling to room temperature and adding water, the reaction liquid was extracted with ethyl acetate. The organic layer was washed with water, dried over magnesium sulfate, and then concentrated. The obtained residue was purified by silica gel column chromatography to obtain phenanthrene-2-amine (9.53 g, 69% yield).

(6-2) Synthesis of Compound A5

Under argon atmosphere, a mixture of phenanthrene-2-amine (9.03 g, 46.7 mmol), 2-bromophenanthiene (12.0 g, 46.7 mmol), tris(dibenzylideneacetone)dipalladium (0) (0.85 g, 0.93 mmol), tri-tert-butylphosphine tetrafluoroborate (1.09 g, 3.74 mmol), sodium t-butoxide (6.29 g, 65.4 mmol), and toluene (250 mL) was refluxed under heating for 7.5 h. After cooling to room temperature, the reaction liquid was concentrated. Methanol was added and the precipitated solid was collected by filtration. The obtained solid was purified by silica gel column chromatography to obtain the compound A5 (12.1 g, 70% yield).

(6-3) Synthesis of Compound H6

Under argon atmosphere, a mixture of the compound A5 (2.70 g, 7.3 mmol), 4-iodobiphenyl (2.05 g, 7.31 mmol), tris(dibenzylideneacetone)dipalladium (0) chloroform adduct (0.16 g, 0.15 mmol), tri-tert-butylphosphine tetrafluoroborate (017 g. 0.58 mmol), sodium t-butoxide (1.40 g, 14.6 mmol), and toluene (37 mL) was refluxed under heating for 3.5 h. After cooling to room temperature, the reaction liquid was concentrated under reduced pressure.

The obtained residue was purified by silica gel column chromatography and recrystallization to obtain the compound H6 (2.11 g, 40% yield).

The structure of the compound H6 was identified by FD-MS analysis.

FD-MS: calcd for C50H33NO=521, found m/z=521

Synthesis Example 7 (Synthesis of Compound H7)

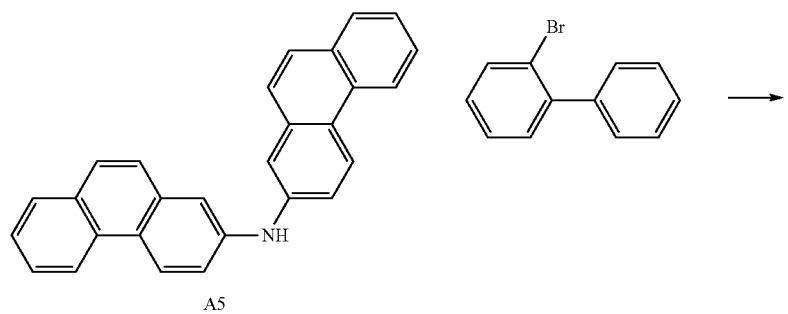

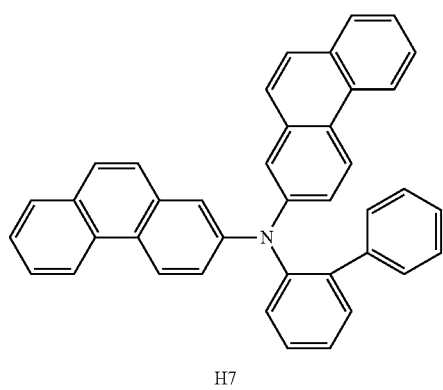

The compound H7 was synthesized in the same manner as in Synthesis Example 6 except for using 2-bromobiphenyl in the step (6-3) in place of 4-iodobiphenyl.

The structure of the compound H7 was identified by FD-MS analysis.

FD-MS: calcd for C50H33NO=521, found m/z=521

Synthesis Example 8 (Synthesis of Compound H8)

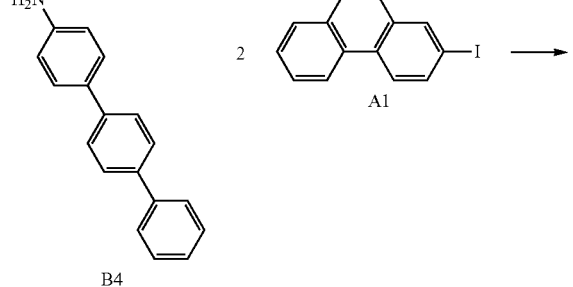

-continued

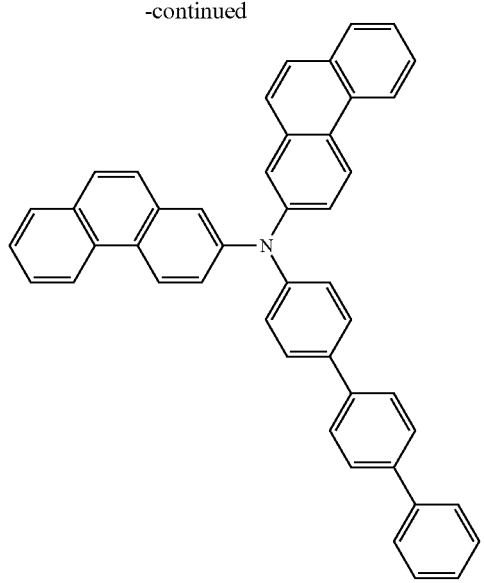

The compound H8 was synthesized in the same manner as in Synthesis Example 2 except for using the compound B4 in place of the compound B2.

The structure of the compound H8 was identified by FD-MS analysis.

FD-MS: calcd for C50H33NO=597,
found m/z=597

Synthesis Example 9 (Synthesis of Compound H9)

(9-1) Synthesis of Compound A6

Under argon atmosphere, a mixture of 2-bromophenanthrene (10.0 g, 38.9 mmol), bispinacolatodiboron (9.8 g, 38.9 mmol), dichloro[1,1'-bis(diphenylphosphino)ferrocene]palladium(II) dichloromethane adduct (0.953 g 1.17 mmol), potassium carbonate (7.63 g, 78 mmol), and dioxane (200 mL) was stirred overnight at 105° C. After adding bispinacolatodiboron (2.02 g. 7.95 mmol) and dichloro[1,1'-bis(diphenylphosphino)ferrocene]palladium (II) dichloromethane adduct (0.953 g, 1.17 mmol), the mixture was stirred at 105° C. for 3 h. The reaction liquid was cooled to room temperature and purified by silica gel column chromatography to obtain the compound A6 (10.4 g, 88% yield).

(9-2) Synthesis of Compound H9

Under argon atmosphere, a mixture of N-(4-biphenylyl)-N,N-bis(4-bromophenyl)amine (5 g, 10.43 mmol), the compound A6 (7.95 g, 26.1 mmol), DME (50 mL), tetrakis (triphenylphosphine)palladium(0) (482 mg, 0.417 mmol), a 2 M aqueous solution of sodium carbonate (15.6 mL, 31.3 mmol) was refluxed overnight under heating. The reaction liquid was cooled to room temperature. The precipitated solid was collected by filtration, dried, and purified by silica gel column chromatography and recrystallization to obtain the compound H9 (2.44 g, 35% yield).

The structure of the compound H9 was identified by FD-MS analysis.

FD-MS: calcd for C50H33NO=673,
found m/z=673

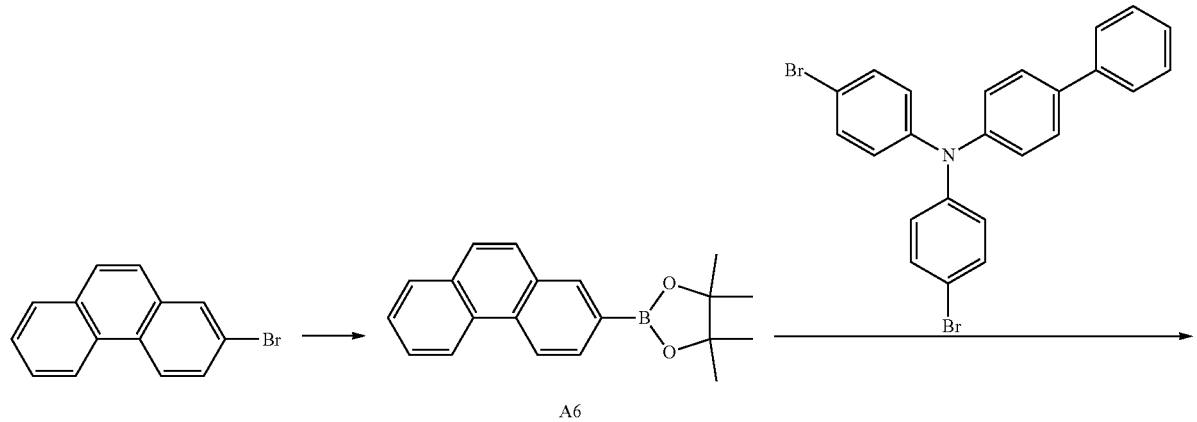

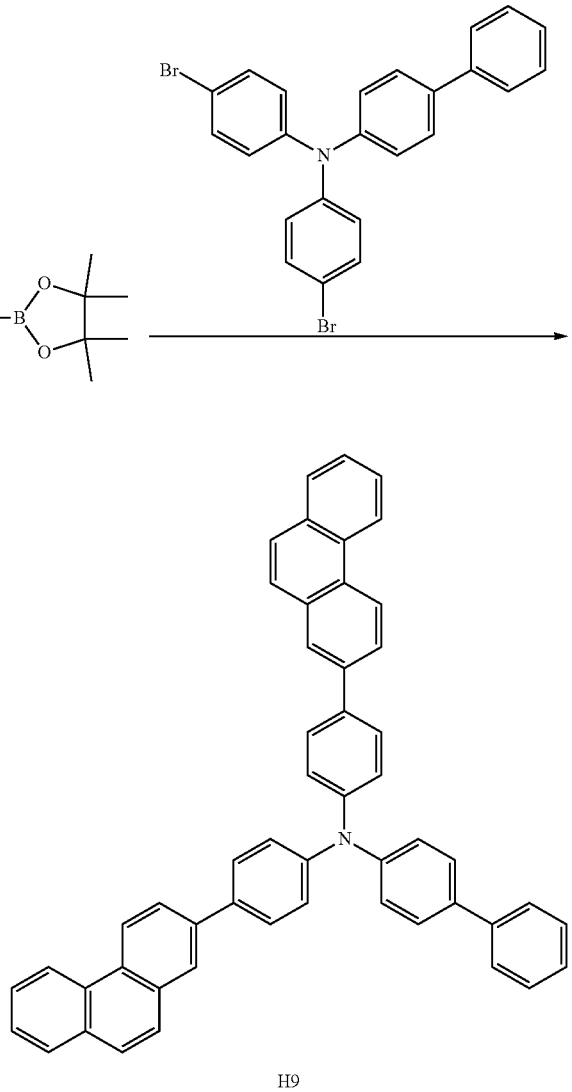

H9

Example 1

Production of Organic EL Device

A glass substrate of 25 mm×75 mm×1.1 mm thick having ITO transparent electrode (product of Geomatec Company) was ultrasonically cleaned in isopropyl alcohol for 5 min and then UV/ozone cleaned for 30 min. The thickness of the ITO transparent electrode was 130 nm.

The cleaned glass substrate having ITO transparent electrode line was mounted to a substrate holder of a vacuum vapor deposition apparatus. First, the compound HI-1 was vapor-deposited so as to cover the ITO transparent electrode line to form an HI-1 film (hole injecting layer) with a thickness of 5 nm.

On the hole injecting layer, the compound HT-1 (first hole transporting material) was vapor-deposited into an HT-1 film with a thickness of 80 nm to form a first hole transporting layer.

On the first hole transporting layer, the compound H1 was vapor-deposited into an HT-2 film with a thickness of 10 nm to form a second hole transporting layer.

On the second hole transporting layer, the compound BH-1 (host material) and the compound BD-1 (dopant material) were vapor co-deposited to form a co-deposited film with a thickness of 25 nm. The concentration of the compound BD-1 was 4.0% by mass. The co-deposited film works as a light emitting layer.

On the light emitting layer, the compound ET-1 was vapor-deposited into an ET-1 film with a thickness of 10 nm to form a first electron transporting layer.

On the first electron transporting layer, the compound ET-2 was vapor-deposited into an ET-2 film with a thickness of 15 nm to form a second electron transporting layer.

On the second electron transporting layer, LiF was vapor-deposited into a LiF film with a thickness of 1 nm to form an electron injecting electrode (cathode).

Then, on the LiF film, metallic Al was vapor-deposited into a metallic Al film with a thickness of 80 nm to form a metallic Al cathode.

Evaluation of Organic EL Device

The organic EL devices thus produced was measured for the external quantum efficiency by applying the voltage so as to give a current density of 10 mA/cm². In addition, the time taken until the luminance was reduced to 80% of the initial luminance (80% luminance lifetime) was measured by driving the device at a current density of 50 mA/cm². The results are shown in Table 1.

Examples 2 to 7 and Comparative Example 1

Each organic EL device was produced in the same manner as in Example 1 except for forming the second hole transporting layer by using each second hole transporting layer material shown in Table 1 in place of the compound H1 and evaluated in the same manner as in Example 1. The results are shown in Table 1.

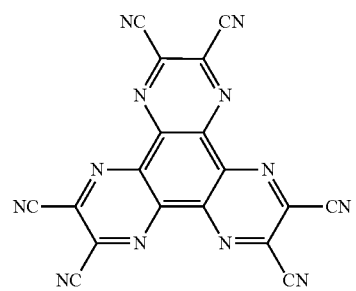

HI-1

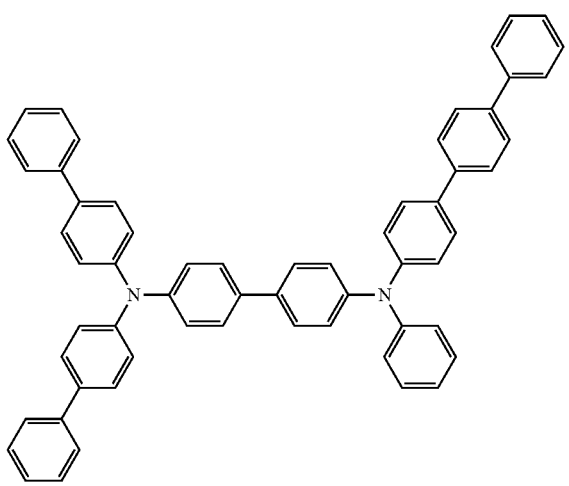

HT-1

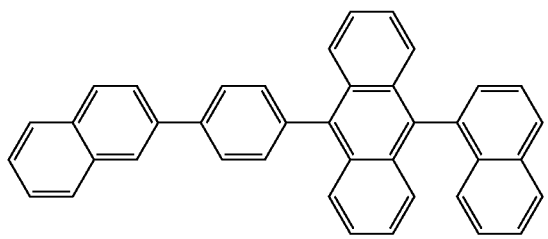

BH-1

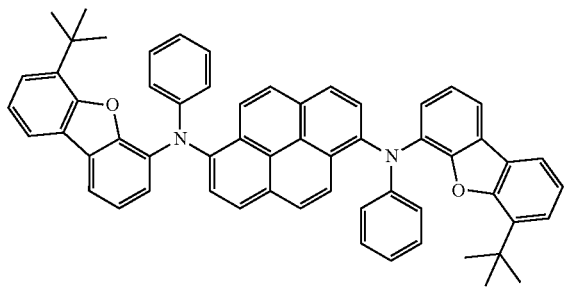

BD-1

-continued

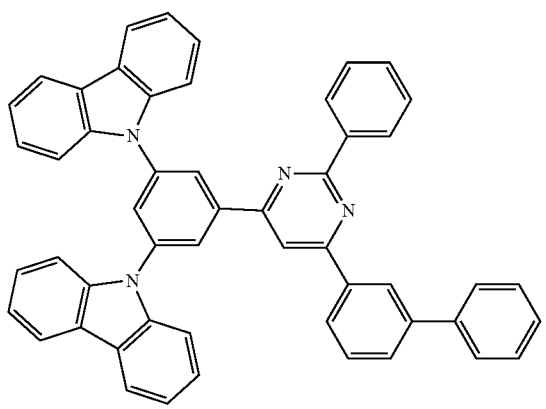

ET-1

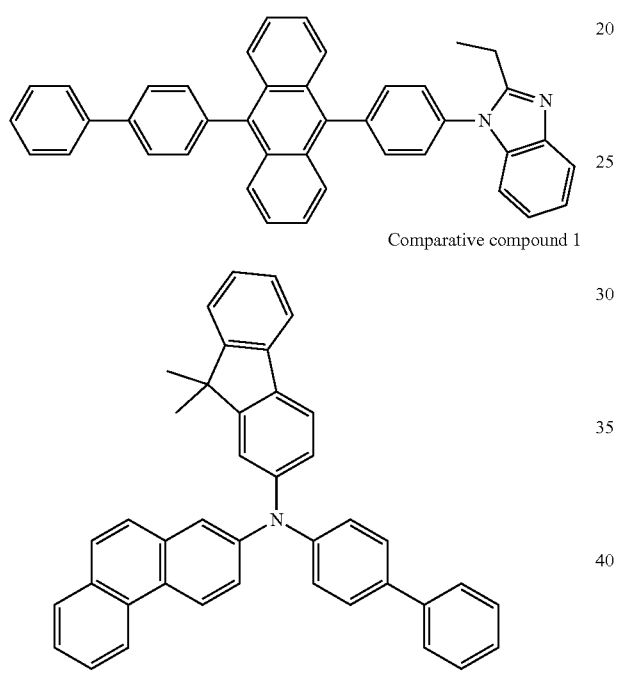

ET-2

Comparative compound 1

TABLE 1

| | Second hole transporting layer material | External quantum efficiency (%) | 80% Luminance lifetime (h) |
|---|---|---|---|
| Example 1 | H1 | 9.2 | 65 |
| Example 2 | H2 | 10.0 | 80 |
| Example 3 | H3 | 9.4 | 240 |
| Example 4 | H6 | 9.2 | 80 |
| Example 5 | H7 | 10.1 | 75 |
| Example 6 | H8 | 9.3 | 140 |
| Example 7 | H9 | 9.5 | 400 |
| Comparative Example 1 | Comparative compound 1 | 8.9 | 50 |

By using the compounds above, the organic EL devices having a high external quantum efficiency and a long 80% luminance lifetime were obtained.

Examples 3 and 7 showed longer 80% luminance lifetime because the compounds H3 and H9 used therein have arylene groups having 6 to 50 ring carbon atoms (phenylene groups) as $L^2$ and $L^3$ of formula (1). The results seem to show that the durability of the compounds was improved by the intervening arylene groups.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

The invention claimed is:
1. A compound represented by formula (1):

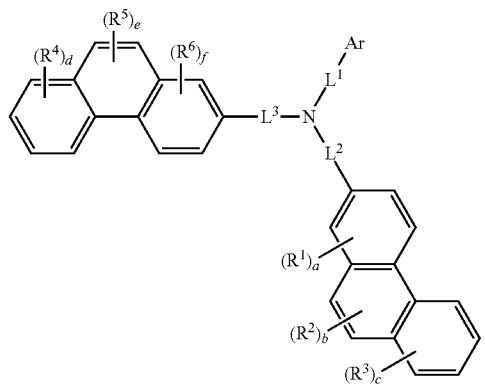

(1)

wherein:
each of $R^1$ to $R^6$ is independently an alkyl group having 1 to 20 carbon atoms or an aryl group having 6 to 18 ring carbon atoms;
a is an integer of 0 or 1, b is an integer of 0 or 1, c is an integer of 0 or 1, d is an integer of 0 or 1, e is an integer of 0 or 1, and f is an integer of 0 or 1; each of $(R^1)_0$, $(R^2)_0$, $(R^3)_0$, $(R^4)_0$, $(R^5)_0$, and $(R^6)_0$ respectively means that $R^1$, $R^2$, R3, $R^4$, $R^5$, or $R^6$ is not present; adjacent two groups selected from $R^1$ to $R^3$ are not bonded to each other, thereby failing to form a ring structure; and adjacent two groups selected from $R^4$ to $R^6$ are not bonded to each other, thereby failing to form a ring structure;
wherein Ar is represented by any of formulae (b-1) to (b-3), to (c-3), (d-1) to (d-3), (e-1) to (e-2), (f-1) to (f-4), and (i-1) to (i-2):

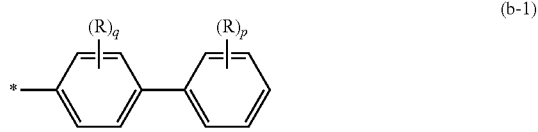

(b-1)

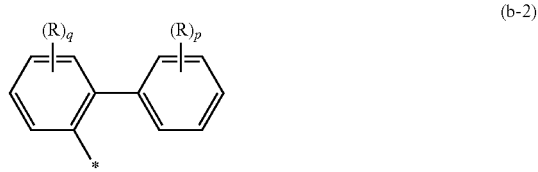

(b-2)

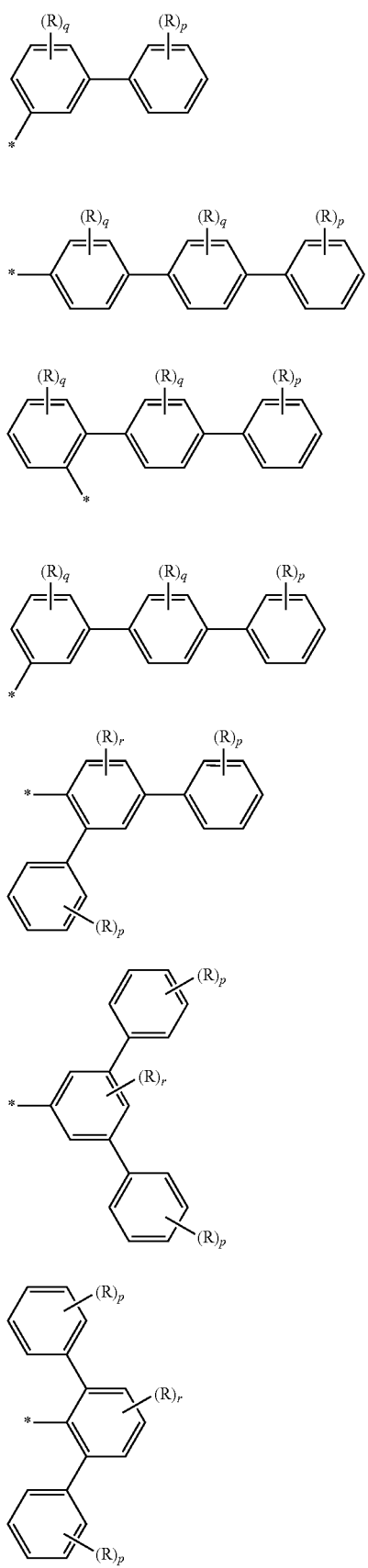
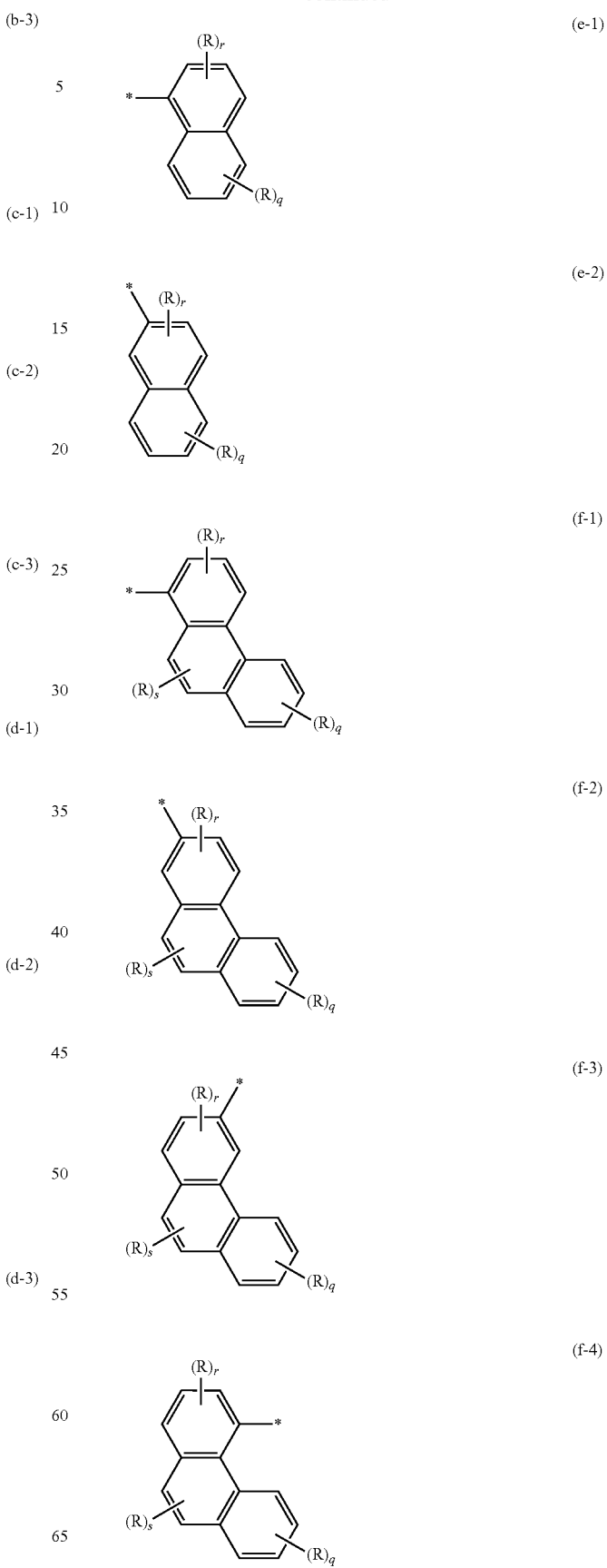

-continued

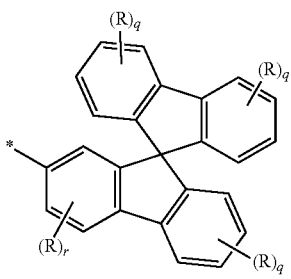
(i-1)

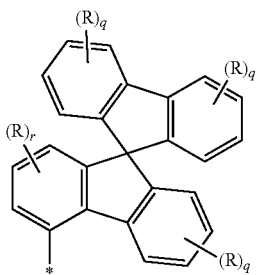
(i-2)

wherein:
* is a bond to $L^1$ in formula (1);
each R is independently an alkyl group having 1 to 20 carbon atoms or an aryl group having 6 to 18 ring carbon atoms, wherein adjacent two Rs in each formula are not bonded to each other and do not form a ring structure;
when Ar is represented by any of formulae (b-1) to (b-3), (c-1) to (c-3), (d-1) to (d-3), and (0-1) to (e-2), each p is independently an integer of 0, each q is independently an integer of 0, each r is independently an integer of 0, and $(R)_0$ means that R is not present;
when Ar is represented by formula (f-1), (f-2), (f-3) or (f-4), each s is an integer of 0 or 1, q is an integer of 0 or 1, r is an integer of 0 or 1, and $(R)_0$ means that R is not present;
when Ar is represented by formula (i-1), or (i-2), each q is independently an integer of 0 or 12 each r is independently an integer of 0 or 1 and $(R)_0$ means that R is not present;
each of $L^1$ to $L^3$ is independently a single bond or an arylene group represented by formula (ii) or (iii):

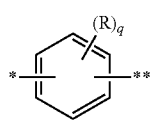
(ii)

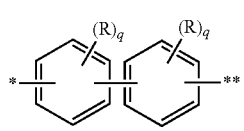
(iii)

wherein:
at least one of $L^2$ and $L^3$ is a single bond;
R is the same as defined with respect to formulae (b-1) to (b-3), (c-1) to (c-3), (d-1) to (d-3), e-1) to (e-2), (f-1) to (f-4), and(i-1) to (i-2);
q is independently an integer of 0;

when $L^1$ is represented by formula (ii) or (iii), one of * and ** is a bond to Ar in formula (1), and the other is a bond to the nitrogen atom in formula (1);
when $L^2$ is represented by formula or (iii), one of * and ** is a bond to the phenanthrene structure in formula (1), and the other is a bond to the nitrogen atom in formula (1); and
when $L^3$ is represented by formula (ii) or (iii), one of * and ** is a bond to the phenanthrene structure in formula (1), and the other is a bond to the nitrogen atom in formula (1).

2. The compound according to claim 1, wherein:
when Ar is represented by any of formulae (b-1) to (b-3) and (c-1) to (c-3), $L^1$ is a single bond;
when Ar is represented by formula (d-1) to (d-3), (e-1) to (e-2), (f-1) to (f-4), or (i-1) to (i-2), $L^1$ is a single bond or formula (ii).

3. The compound according to claim 1, wherein each of $L^2$ and $L^3$ is a single bond.

4. The compound according to claim 1, wherein each of $L^1$ to $L^3$ is a single bond.

5. The compound according to claim 1, wherein the compound is a compound represented by any of the following formulae:

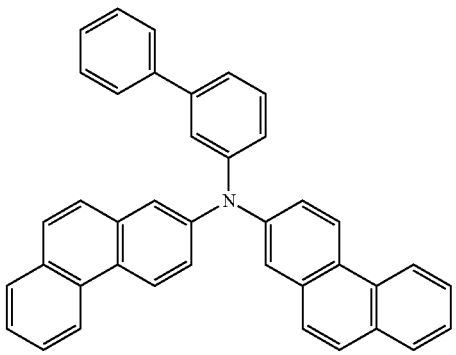

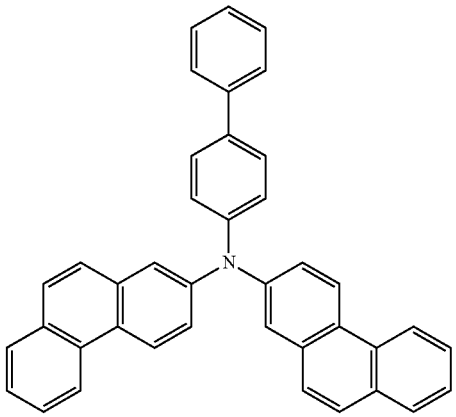

93
-continued
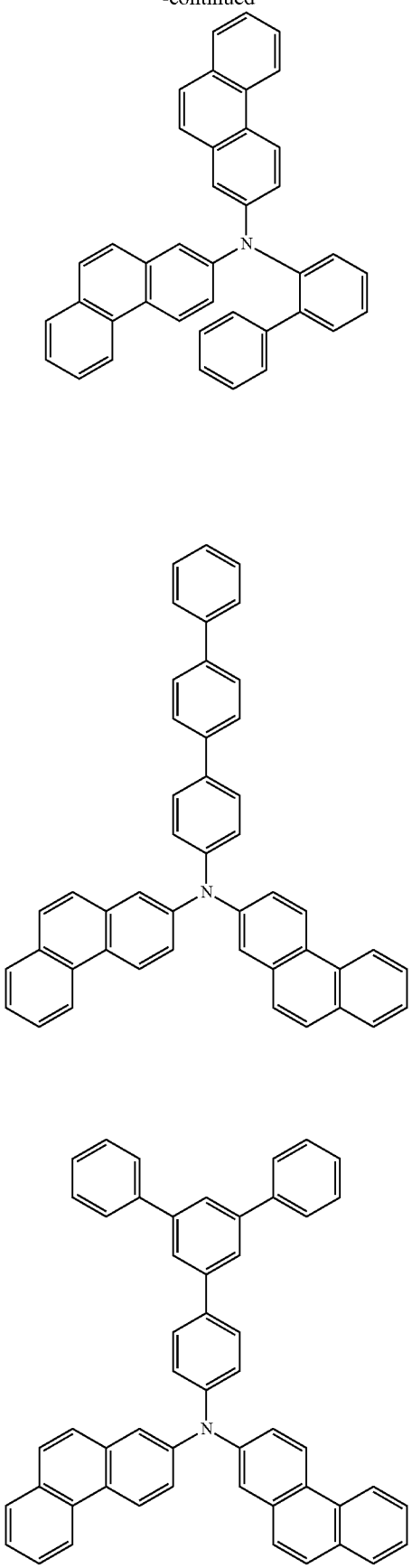
94
-continued
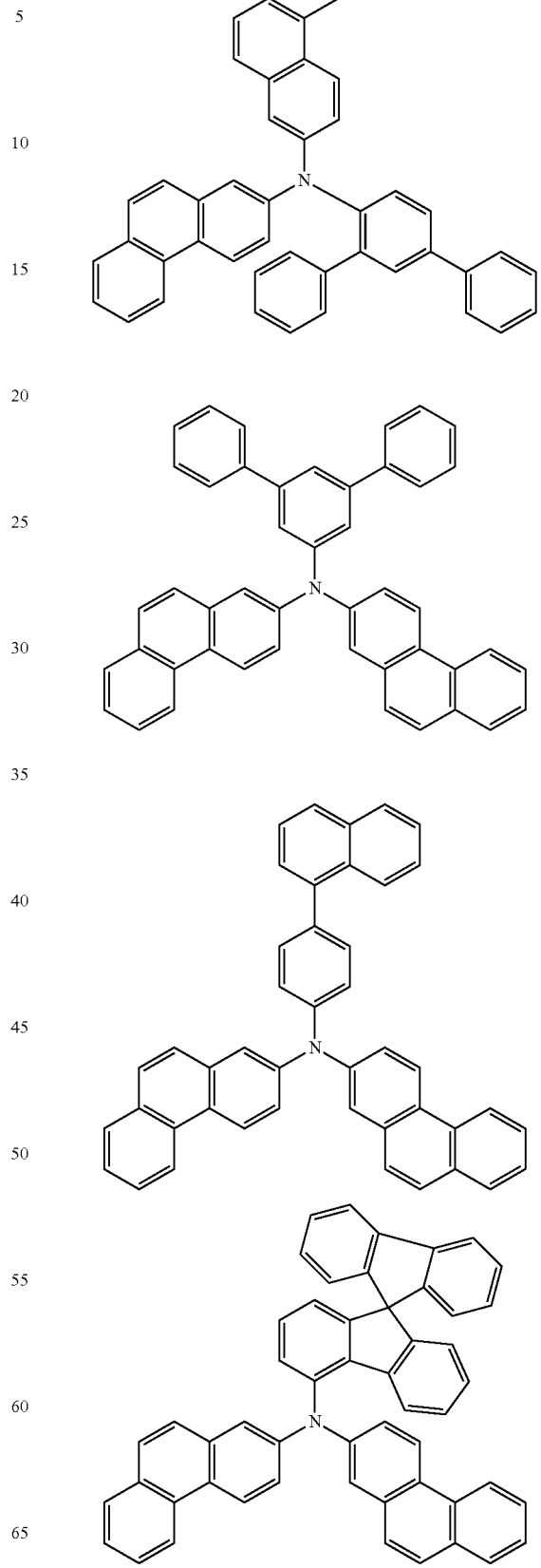

95
-continued
96
-continued
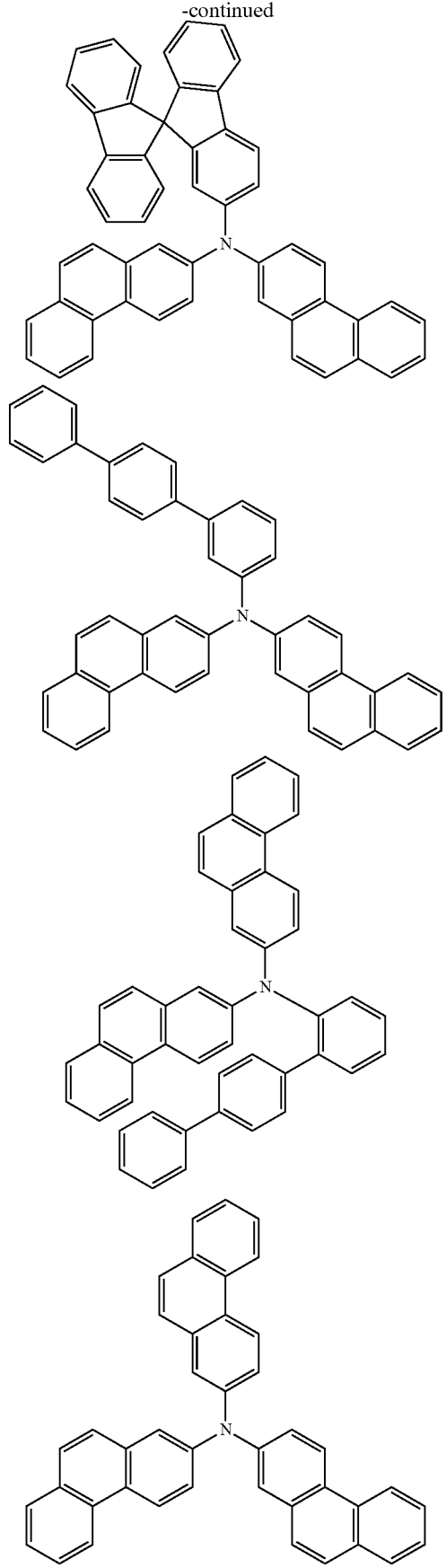
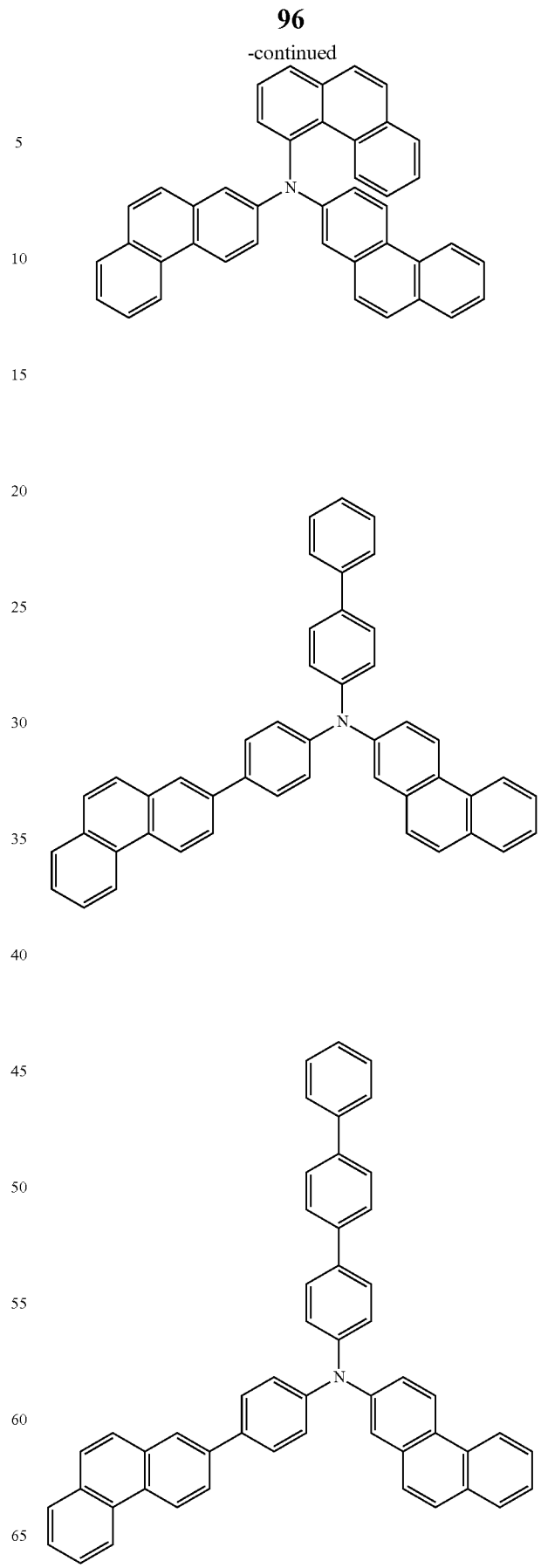

97
-continued
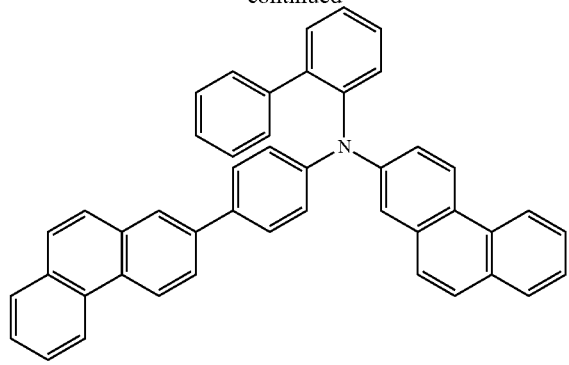
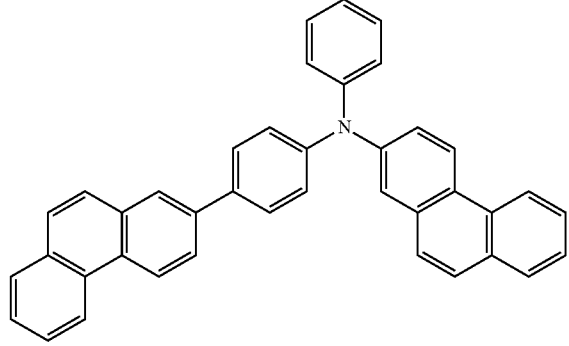
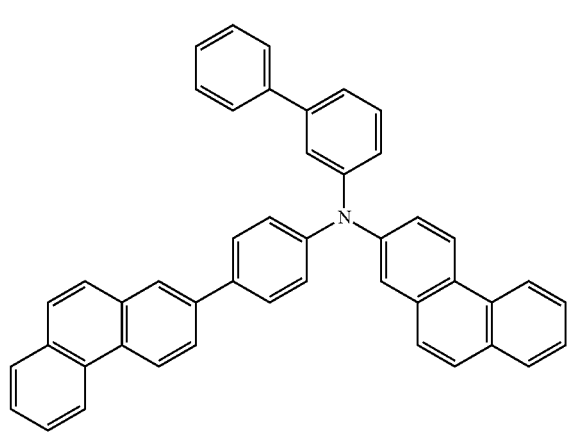
98
-continued
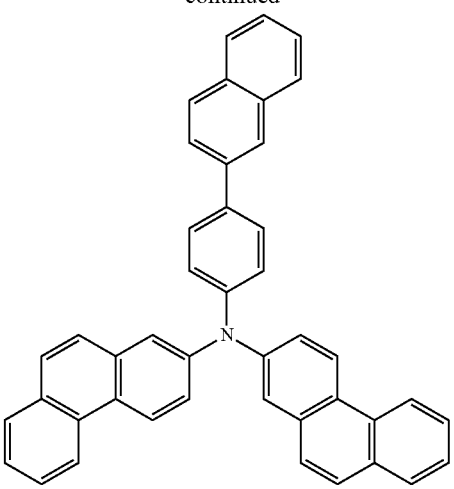
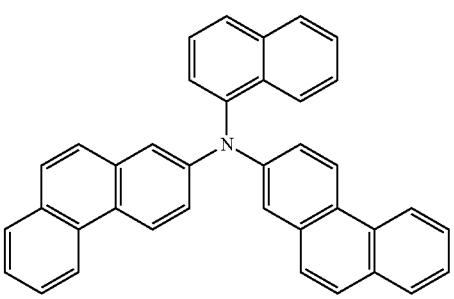
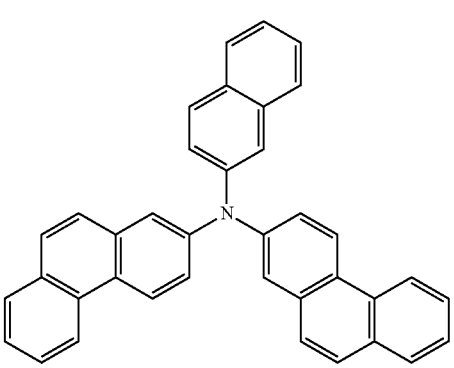
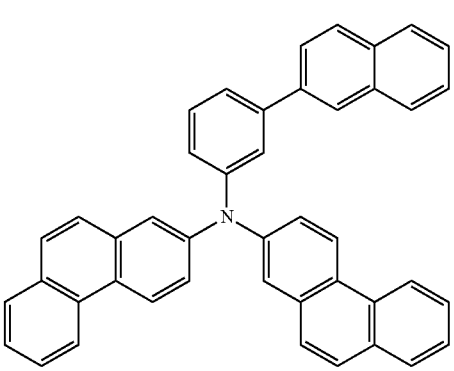

99
-continued

100
-continued

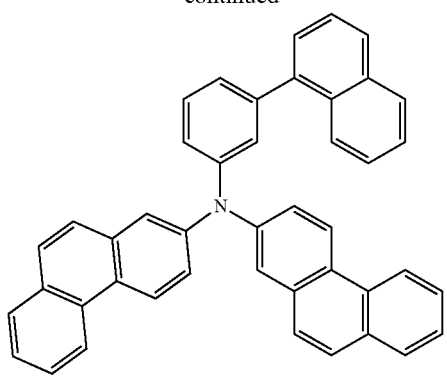

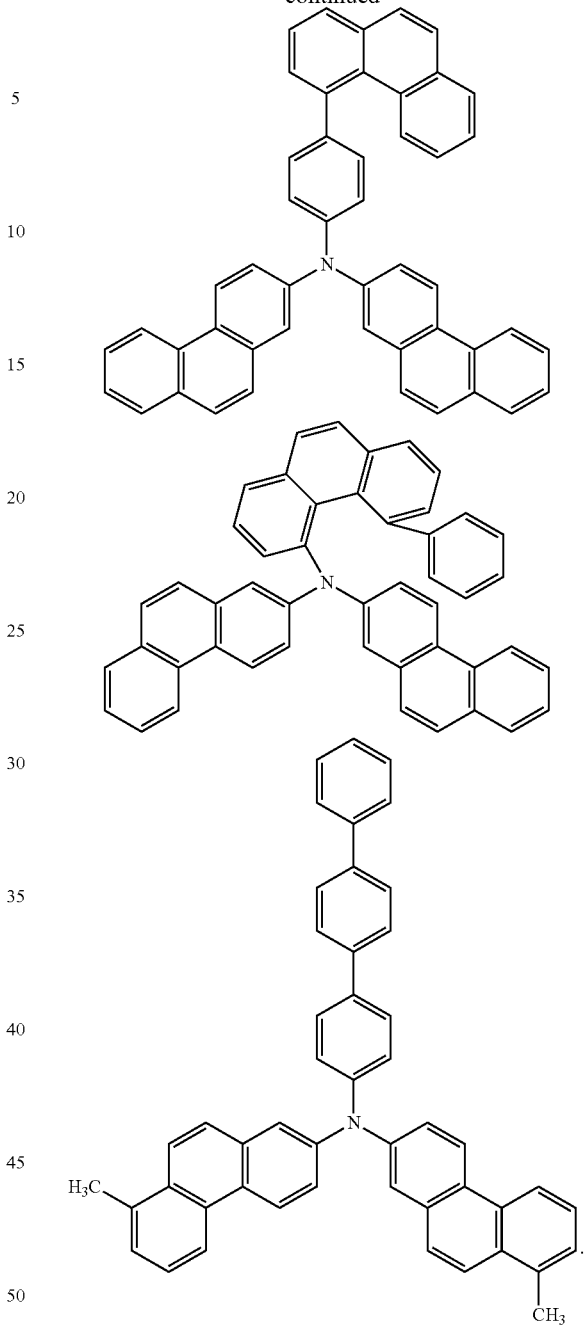

6. A material for organic electroluminescence devices which comprises the compound according to claim 1.

7. An organic electroluminescence device comprising a cathode, an anode, and an organic thin film layer disposed between the cathode and the anode, wherein the organic thin film layer comprises one or more layers, the organic thin film layer comprises a light emitting layer, and at least one layer of the organic thin film layer comprises the compound according to claim 1.

8. The organic electroluminescence device according to claim 7, wherein the organic electroluminescence device cotnprises a hole transporting layer between the anode and the light emitting layer, and the hole transporting layer comprises the compound.

9. The organic electroluminescence device according to claim 7, wherein the organic electroluminescence device comprises an electron blocking layer between the anode and the light emitting layer, and the electron blocking layer comprises the compound.

10. The organic electroluminescence device according to claim 7, wherein the organic electroluminescence device comprises an excitors blocking layer between the anode and the light emitting layer, and the exciton blocking layer comprises the compound.

11. The organic electroluminescence device according to claim 7, wherein the organic electroluminescence device comprises an anode-side organic thin film layer between the anode and the light emitting layer, the anode-side organic thin film layer comprises one or more layers, and at least one layer of the anode-side organic thin film layer comprises the compound.

12. The organic electroluminescence device according to claim 11, wherein the anode-side organic thin film layer comprising two or more layers comprises two or more hole transporting layers, and a hole transporting layer closest to the anode comprises the compound.

13. The organic electroluminescence device according to claim 11, wherein the anode-side organic thin film layer comprising two or more layers comprises two or more hole transporting layers, and a hole transporting layer closest to the light emitting layer comprises the compound.

14. An electronic device comprising the organic electroluminescence device according to claim 7.

15. The compound according to claim 1, wherein the compound is a compound represented by any of the following formulae:

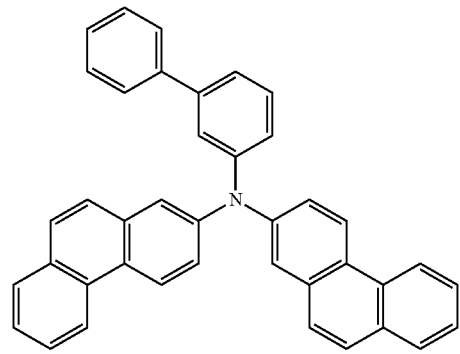

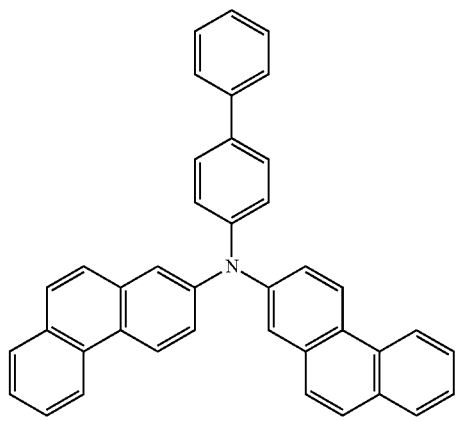

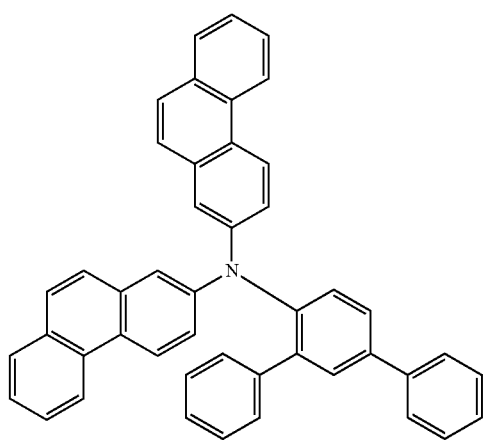

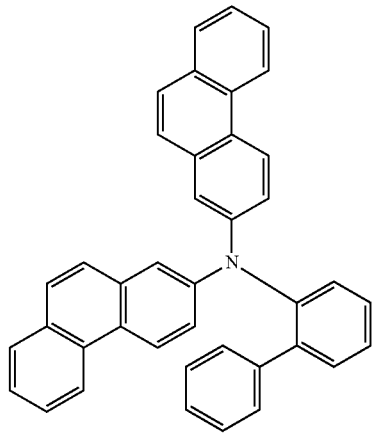

103
-continued
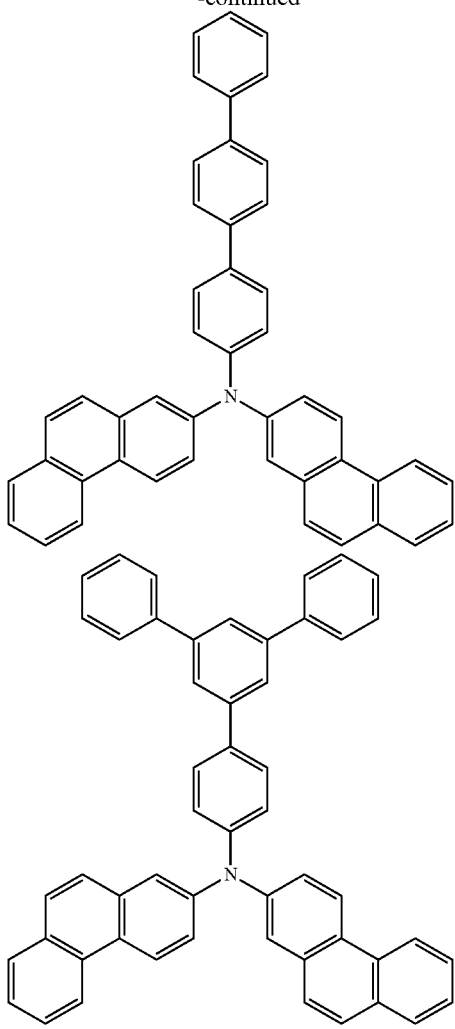
104
-continued
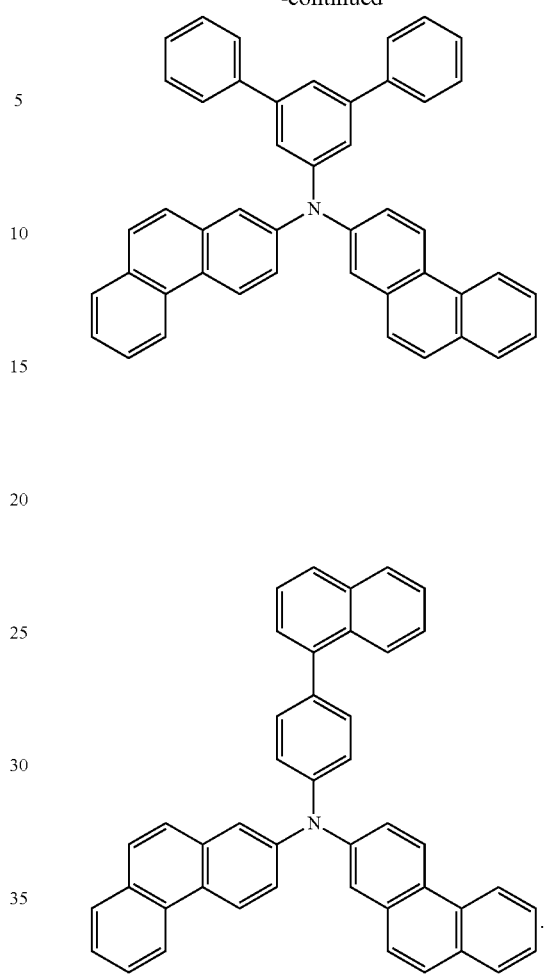
* * * * *